US007759318B1

(12) United States Patent
Perera et al.

(10) Patent No.: US 7,759,318 B1
(45) Date of Patent: Jul. 20, 2010

(54) IDENTIFICATION OF NOVEL PATHWAYS, GENES AND PROMOTER MOTIFS REGULATING ADIPOGENESIS

(75) Inventors: Ranjan Perera, Carlsbad, CA (US); Seongjoon Koo, San Marcos, CA (US); Nicholas M. Dean, Olivenhain, CA (US); Eric G. Marcusson, San Francisco, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 782 days.

(21) Appl. No.: 11/140,437

(22) Filed: May 27, 2005

Related U.S. Application Data

(60) Provisional application No. 60/607,189, filed on Sep. 2, 2004, provisional application No. 60/575,160, filed on May 28, 2004.

(51) Int. Cl.
*A61K 48/00* (2006.01)
(52) U.S. Cl. ............... 514/44; 536/24.5; 536/24.1; 536/24.31
(58) Field of Classification Search .................. None
See application file for complete search history.

(56) References Cited

U.S. PATENT DOCUMENTS

| 5,801,154 | A | * | 9/1998 | Baracchini et al. ............ 514/44 |
| 6,159,734 | A | | 12/2000 | McKay et al. |
| 6,582,908 | B2 | | 6/2003 | Fodor et al. |
| 6,746,868 | B1 | * | 6/2004 | Felgner et al. ............. 435/455 |
| 2001/0053519 | A1 | | 12/2001 | Fodor et al. |
| 2005/0130193 | A1 | * | 6/2005 | Luxon et al. ................. 435/6 |
| 2006/0019256 | A1 | | 1/2006 | Clarke et al. |
| 2006/0115821 | A1 | | 6/2006 | Elnstein et al. |

OTHER PUBLICATIONS

Taylor et al. Antisense oligonucleotides: a systematic high-throughput approach to target validation and gene function determination. DDT, vol. 4, No. 12, Dec. 1999.*

Ashrafi, K. et al., "Genome-wide RNAi analysis of *Caenorhabditis elegans* fat regulatory genes," Nature (2003) 421 (6920):268-272.
Burant, C. F. et al., "Troglitazone Action Is Independent of Adipose Tissue," J. Clin. Invest. (1997) 100 (11):2900-2908.
Hamm, J. K. et al., "Role of PPARgamma in Regulating Adipocyte Differentiation and Insulin-Responsive Glucose Uptake," An. NY Acad. Sci. (1999) 892:134-145.
Jiang, W. G. et al., "Peroxisome proliferator activated receptor-gamma (PPAR-gamma) mediates the action of gamma linolenic acid in breast cancer cells," Prostaglandins, Leukotrienes and Essential Fatty Acids (2000) 62 (2):119-127.
Nikitakis, N. G. et al., "PPAR gamma-mediated antineoplastic effect of NSAID sulindac on human oral squamous carcinoma cells," Int. J. Cancer (2002) 98(6):817-823.
Tong, Q. et al., "Function of GATA Transcription Factors in Preadipocyte-Adipocyte Transition," Science (2000) 290 (5489):134-138.
Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.
New England BioLabs, Inc. Catalogue (1998): 121, 284.
Reynolds et al., Rational siRNA design for RNA interference, Mar. 2004, Nature Biotechnology, vol. 22, pp. 326-330.
Branch et al., "A good antisense molecule is hard to find," TIBS (1998) 23:45-50.
Crooke et al., "Basic Principles of Antisense Therapeutics" Antisense Research and Application (1998) Chapter 1:1-50.
Sanghvi et al., "Heterocyclic Base Modifications in Nucleic Acids and Their Applications in Antisense Oligonucleotides" Antisense Research and Applications (1993) pp. 273-288.
Taylor et al., "Antisense oligonucleotides: a systemic high-throughput approach to target validation and gene function determination" DDT (1999) 4(12):562-567.

* cited by examiner

*Primary Examiner*—Kimberly Chong

(57) ABSTRACT

The present invention provides compounds, compositions, and methods for identification of motifs within regulatory regions of genes involved in adipogenesis and adipocyte differentiation. Compounds and compositions are provided for modulating expression of nuclear receptor/transcription factor-regulated genes. Methods for modulating the function of PPAR-γ as well as PPAR-γ-regulated gene promoters, and methods of using oligomeric compounds for diagnosis and treatment of diseases such as obesity and diabetes are also provided.

23 Claims, 2 Drawing Sheets

IDENTIFICATION OF NOVEL PATHWAYS, GENES AND PROMOTER MOTIFS REGULATING ADIPOGENESIS

CROSS-REFERENCE TO RELATED APPLICATIONS

This application claims priority to U.S. provisional application Ser. No. 60/575,160 filed May 28, 2004 and to U.S. provisional application Ser. No. 60/607,189 filed Sep. 2, 2004, each of which is incorporated herein by reference in its entirety.

FIELD OF THE INVENTION

The present invention is directed, in part, to compounds, compositions, and methods for identification of regulatory motifs in promoters of genes involved in adipogenesis and adipocyte differentiation. In particular, this invention relates to oligomeric compounds, especially nucleic acid and nucleic acid-like oligomers, which are targeted to a nucleic acid comprising a nuclear receptor/transcription factor that regulates the expression of a family of genes, and thereby modulate the expression of downstream genes in a gene family regulated by the nuclear receptor/transcription factor. In some embodiments pharmaceutical and other compositions comprising the compounds of the invention are also provided. Also provided are data integration processes employing data gleaned from phenotypic assays, microarray expression analyses and in silico methods, leading to the identification of sequence motifs within a family of similarly-regulated genes. Methods of treating or preventing a disease or disorder associated with aberrant adipocyte differentiation, such as obesity and diabetes are also provided. Methods of screening for conserved sequence motifs within a family of similarly-regulated genes, as well as kits and assay devices comprising the compounds or compositions of the invention are also set forth herein.

BACKGROUND OF THE INVENTION

Over the last fifty years, the incidence of obesity and its associated complications such as diabetes and heart disease has increased at alarming rates in developed nations (Kopelman, Nature, 2000, 404, 635-43; Seidell, Br. J. Nutr., 2000, 83, Suppl 1, S5-8; James et al., Obes. Res., 2001, 9, Suppl 4, 228S-233S; and Melanson et al., Cardiol. Rev., 2001, 9, 202-7). The level of obesity in a subject is a function of both adipose cell number and cell volume. The number of mature adipocytes is influenced by both the rate of differentiation of preadipocytes into adipocytes as well as adipocyte death by apoptosis. Obesity is often accompanied by glucose intolerance and insulin resistance in the liver, muscle and adipose tissue which can lead to defects in insulin secretion from pancreatic beta cells and eventually type II diabetes. Obesity is also associated with metabolic syndrome, hyperlypedemia and cardiovascular disease. Thus, the obesity epidemic has a profound effect on public health (Visscher et al., Annu. Rev. Public Health, 2001, 22, 355-75) and there is a great need for more therapeutics for the treatment or prevention of obesity (Van der Ploeg, Curr. Opin. Chem. Biol., 2000, 4, 452-60).

Adipogenesis is a complex process by which undifferentiated precursor cells differentiate, into fat cells. The peroxisome proliferator-activated receptors (PPARs) are members of the nuclear hormone receptor family, the largest family of transcription factors. Three distinct members of the PPAR subfamily have been described: alpha, delta (also called beta, NUC-1 or FAAR) and gamma. All of these PPAR gene family members are activated by naturally occurring fatty acids or fatty acid derivatives. PPARs heterodimerize with the retinoid X receptor (RXR) and regulate transcription of other genes through binding to specific PPAR recognition/response elements (PPREs), which consist of a direct repeat of the nuclear receptor hexameric DNA core recognition motif spaced by one nucleotide. A number of studies have reported that peroxisome proliferator activated receptor-gamma (PPAR-gamma; also known as PPAR-γ) plays a central role in glucose homeostasis and insulin sensitivity as well as adipogenesis. Furthermore, while cell proliferation and differentiation are sometimes considered to be mutually exclusive events, a close relationship has been established between these processes during adipocyte differentiation. One of the first events occurring during the adipogenesis program is re-entry of growth-arrested preadipocytes into the cell cycle following hormonal induction. After several rounds of clonal expansion, cells arrest proliferation again and undergo terminal adipocyte differentiation. PPAR-γ has been implicated in the control of cell proliferation and apoptosis as well as differentiation pathways in various malignancies, suggesting a role for PPAR-γ in carcinogenesis (Fajas et al., J. Mol. Endocrinol., 2001, 27, 1-9).

It has become clear that adipocytes play significant roles in regulating the body's metabolism (Bluher et al., Dev. Cell., 2002, 3, 25-38). The adipocyte, once thought of as a simple energy depot, is now known to be a highly specialized cell type involved in energy homeostatis, metabolic control and even behavior. In vivo, adipocyte differentiation is a complex process accompanied by coordinated changes in cell morphology, hormone sensitivity, gene expression and secretory capacity. Several transcription factors such as PPAR-γ, CCAAT/enhancer binding protein-alpha (CEBPα), and sterol-regulatory element-binding transcription factor 1 (SREBP1) are involved in this process (Spiegelman et al., Cell, 1996, 87, 377-89). Measurable changes occur during the progression of differentiation. These changes include the accumulation of triglycerides as lipid droplets, the secretion of several hormones and autocrine factors (e.g. leptin and adiponectin) and characteristic changes in gene expression including increased expression of PPAR-γ, hormone sensitive lipase (HSL), glucose transporter 4 (Glut4) and adipocyte lipid binding protein 2 (aP2). The process of adipocyte differentiation can be modeled in vitro by incubating pre-adipocytes with insulin, a PPAR-γ agonist, hydrocortisone and a compound that increases intracellular levels of cyclic adenosine monophosphate (cAMP), usually 3-isobutylmethylxanthine (IBMX).

Many experiments have shown that PPAR-γ appears to be an important regulator of adipocyte differentiation (Hamm et al., Ann. N.Y. Acad. Sci., 1999, 892, 134-45; Grimaldi, Prog. Lipid Res., 2001, 40, 269-81). In its role as a nuclear hormone receptor/transcription factor, PPAR-γ pairs with its heterodimeric partner, retinoid X receptor a (RXR-alpha), to form a DNA binding complex that regulates the transcription of adipocyte-specific genes (Kliewer et al., Proc. Natl. Acad. Sci. U.S.A., 1992, 89, 1448-52). PPARs possess the same P-box sequence (the DNA binding motif) of most type II steroid hormone receptors. To date, most PPREs are direct repeats with one intervening nucleotide (DR-1). RXR acts as the preferential binding partner and the PPAR/RXR heterodimer recognizes the PPRE (DiRenzo et al., Mol. Cell. Biol., 1997, 17, 2166-76). The elucidation of PPAR-γ-regulated genes and the pathways downstream of PPAR-γ is of fundamental importance in order to identify drug targets for the treatment of metabolic diseases. Currently, however, only limited information available about PPAR-γ downstream target genes exists.

In recent years, various data analysis techniques such as cluster analysis algorithms, have provided many possibilities to analyze microarray gene expression data that could group genes into co-regulatory clusters (Shannon et al., Pharmacogenomics, 2003, 4, 41-52). Similarly, promoter sequences of each gene in a cluster can be immediately fed to cis-regulatory discovery algorithms to identify motifs that share in functionally related genes (Keles et al., Bioinformatics, 2002, 18, 1167-75). Therefore, motifs that are common to a set of apparently co-expressed genes are plausible candidates for binding sites implicated in PPAR-γ transcriptional regulation. Several genes have already been characterized for the presence of PPAR-γ binding element. Though the PPREs possess the same P-box (TGACCTnTGACCT; SEQ ID NO:5) of type 11 steroid hormone receptors, the actual binding motif may differ compared to the consensus P-box element in PPAR-γ-regulated genes.

Currently, it is known that compounds, including thiazolidinediones, that bind and activate PPAR-γ can improve insulin sensitivity and reduce hyperglycemia and hyperlipidemia in man. Although it is still controversial, these drugs appear to increase insulin sensitivity in the adipose tissue, muscle and liver (Burant et al., J. Clin. Invest., 1997, 100, 2900-8). Thus, PPAR-γ agonists are becoming increasingly important in the fight against type II diabetes, and the market share of these drugs is increasing. However, PPAR-γ agonists have negative side effects; such negative side effects as unwanted weight gain and increased adipose mass confound the situation. Furthermore, the long-term effects of these drugs have yet to be determined.

There remains a long-felt need for compounds which modulate the expression of genes involved in adipogenesis, cell proliferation and/or cell differentiation, including candidate therapeutic agents and compounds useful in the treatment, attenuation or prevention of pathologies such as obesity, hyperlipidemia, atherosclerosis, atherogenesis, diabetes, hypertension, or other metabolic diseases as well as having potential applications in the maintenance of the pluripotent phenotype of stem or precursor cells. The present invention provides compounds and methods useful for modulating gene expression pathways, including methods relying on mechanisms of action such as RNA interference, small non-coding RNAs, dsRNA enzymes, antisense and non-antisense mechanisms. One having skill in the art, once armed with this disclosure will be able, without undue experimentation, to identify oligonucleotide compounds and methods for these uses.

SUMMARY OF THE INVENTION

The present invention is directed to oligomeric compounds, particularly nucleic acid and nucleic acid-like oligomers, which are targeted to a nucleic acid comprising a nuclear receptor/transcription factor that regulates the expression of a family of genes. The compounds modulate the expression levels of the nuclear receptor/transcription factor mRNA target (for example, by transcriptional silencing or translational inhibition), thereby resulting in a change in expression of the downstream genes in the gene family regulated by the nuclear receptor/transcription factor. For example, the present invention provides oligomeric compounds targeted to the nuclear receptor/transcription factor PPAR-γ, which regulates the expression of a family of downstream genes including, for example, hypothetical protein FLJ20920, ALDH9A1, COX10, PLIN, FACL1, Notch3, SLC7A6, EBP, SRP72, Malic Enzyme1 (ME1), Lipoprotein Lipase (LPL), PTD010 protein, Four-and-a-half-LIM-domains 1, hypothetical protein FLJ10079, Lipin 1, ACAD8, AKR1C3, ALDH3A2, ALDH3B1, CD36, HADHA, AKR1C3, CTGF, CYR61, CSPG2 and PRG1. Pharmaceutical and other compositions comprising the compounds of the invention are also provided. Further provided are methods of identifying sequence motifs within a family of similarly-regulated genes using processes that integrates data from phenotypic assays obtained in oligonucleotide knock-down studies, promoter comparisons obtained by computer algorithms, and microarray expression analyses. Methods of treating or preventing a disease or disorder associated with aberrant adipocyte differentiation, such as obesity and diabetes are also provided. Methods of screening for conserved sequence motifs within a family of similarly-regulated genes, as well as kits and assay devices comprising the compounds or compositions of the invention are also set forth herein.

DESCRIPTION OF EMBODIMENTS

Figure 1:
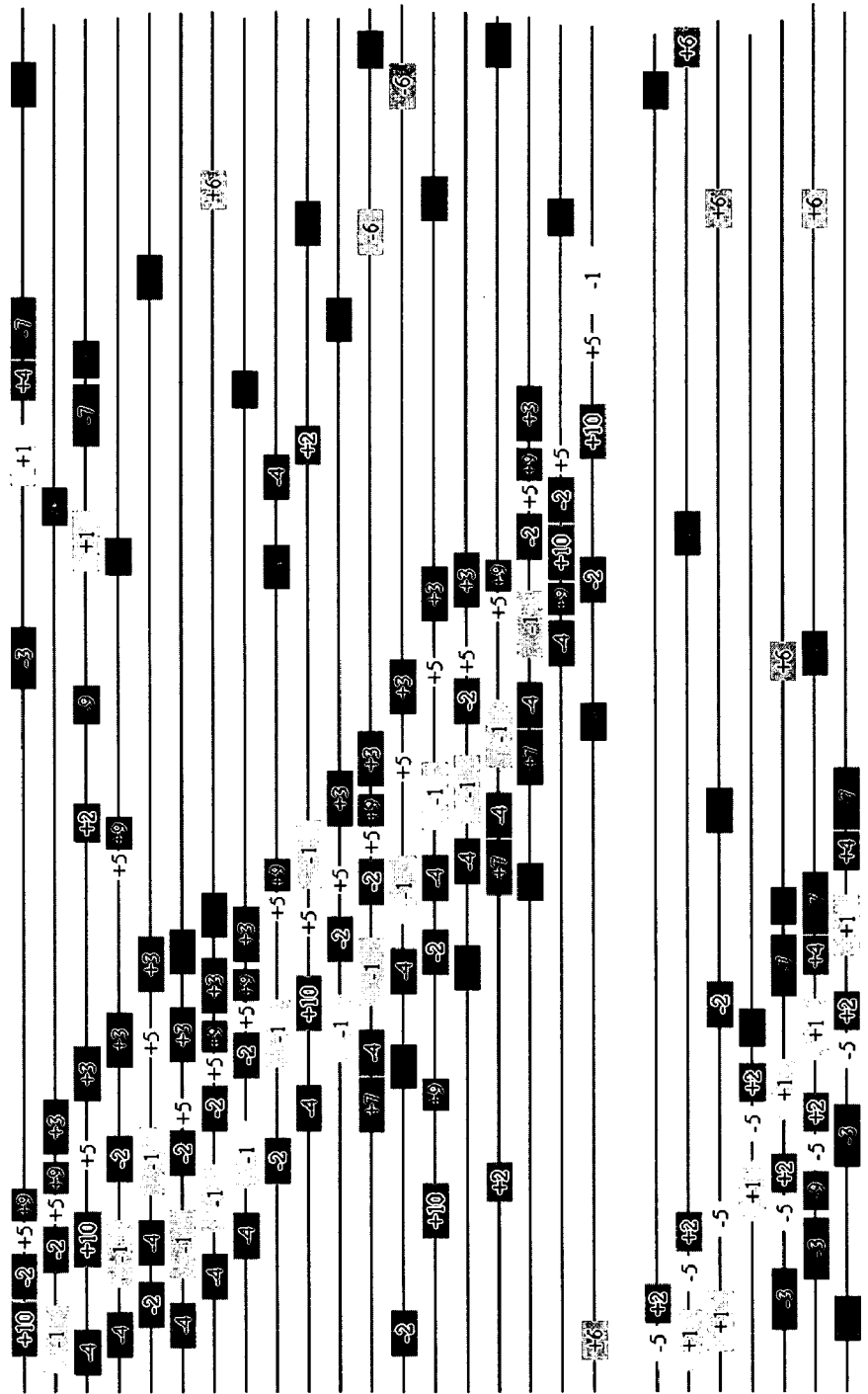
FIG. 1 shows the largest cluster (MEME Cluster #1), which contains 19 genes. The ALDH9A1, COX10, PLIN, FACL1, Notch3, SLC7A6 and EBP genes have been reported to be involved in fatty acid metabolism. The *Drosophila* serpent (SRP) gene homolog SRP72, known to play a role in fat body formation, was discovered in MEME cluster #2 (data not shown). In these clusters, each motif is assigned a number according to its level of sequence similarities. Motifs can be found either in (+) or (−) DNA strands.

The present invention provides, inter alia, oligomeric compounds useful in, for example, the modulation of expression, endogenous levels or the function of PPAR-γregulated genes. More specifically, oligomeric compounds of the invention modulate the expression of the PPAR-γ gene itself and/or PPAR-γ-regulated downstream genes by hybridizing to the PPAR-γ mRNA or a PPAR-γ regulated target promoter, resulting in loss of normal function of the PPAR-γ nuclear hormone receptor or PPAR-γ-regulated gene promoters either by facilitating destruction of genomic DNA sequences encoding PPAR-γ or PPAR-γ-regulated gene promoters through cleavage or sequestration or by sterically occluding the function of the mRNA or promoter through formation of a physical complex.

The present invention provides oligomeric compounds comprising a first region and a second region, wherein at least one of said first or second regions contains a modification, wherein a portion of the oligomeric compound is targeted to a nuclear receptor/transcription factor which regulates the expression of at least one member of a gene family, and wherein the compound inhibits expression of the nuclear receptor/transcription factor thereby resulting in a change in expression of the at least one member of said gene family. The invention further provides a composition comprising the oligomeric compound and a carrier or diluent. In some embodiments, the gene family is the set of PPAR-γ-regulated genes, comprising, in part, the hypothetical protein FLJ20920, ALDH9A1, COX10, PLIN, FACL1, Notch3, SLC7A6, EBP, SRP72, Malic Enzyme 1 (ME 1), Lipoprotein Lipase (LPL), PTD010 protein, Four-and-a-half-LIM-domains 1, hypothetical protein FLJ10079, Lipin 1, ACAD8, AKR1C3, ALDH3A2, ALDH3B1, CD36, HADHA, AKR1C3, CTGF, CYR61, CSPG2 and PRG1 genes.

As used herein, the terms "nuclear receptor/transcription factor," "nuclear hormone receptor," "ligand-activated receptor," or "intracellular receptor" refer to the large family of intracellular proteins which are known to homo- or heterodimerize, in some cases binding to other ligands, and which are involved in binding and transcriptional regulation (activation or repression) of DNA regulatory elements such as promoters or enhancer regions.

As used herein, the terms "DNA regulatory element," "promoter," and "enhancer" refer to genomic DNA sequences physically associated with, but often at distances spanning kilobases of DNA, gene coding sequences, and which may be bound and regulated by proteins, protein complexes, nucleic acids, or ribonucleoprotein particles.

The terms "gene-family" or "similarly-regulated genes" mean a group of genomic DNA sequences which are transcribed coordinately (concurrently or in a temporally coordinated, regulated manner), which may share similar structures, conserved sequences, and/or cellular functions, and which may interact with a common set of proteins or nucleic acids.

"PPAR-γ-regulated genes" means a group of genes which are directly or indirectly regulated by the PPAR-γ nuclear hormone receptor, alone or in conjunction with other proteins, protein complexes, nucleic acids, or ribonucleoprotein complexes. The group of PPAR-γ-regulated genes may include, but is not limited to, the group of genes identified by the experiments described in examples hereinbelow. Examples of genes predicted to be regulated by PPAR-γ include, but are not limited to, the hypothetical protein FLJ20920, ALDH9A1, COX10, PLIN, FACL1, Notch3, SLC7A6, EBP, SRP72, Malic Enzyme1 (ME1), Lipoprotein Lipase (LPL), PTD010 protein, Four-and-a-half-LIM-domains 1, hypothetical protein FLJ10079, Lipin 1, ACAD8, AKR1C3, ALDH3A2, ALDH3B1, CD36, HADHA, AKR1C3, CTGF, CYR61, CSPG2 and PRG1 genes.

In the context of the present invention, the terms "adipogenesis" or "adipocyte differentiation" refer to the regulated processes by which an undifferentiated precursor cell differentiates into a fat cell, and which takes place from the time of birth through adulthood in mammals.

As used herein, the term "target nucleic acid" or "nucleic acid target" is used for convenience to encompass any nucleic acid capable of being targeted including, without limitation, RNA (including microRNAs, stRNAs, small nuclear RNAs, small nucleolar RNAs, small ribosomal RNAs, small hairpin RNAs, endogenous antisense RNAs, guide RNAs, tiny noncoding RNAs, rasiRNAs, small single or double stranded RNAs that are encoded by heterochromatic repeats at centromeres or other chromosomal origin, and any precursors thereof) transcribed from DNA. In some embodiments of this invention, modulation of target nucleic acid expression or function is effected via modulation of an RNA associated with the particular target nucleic acid. This association can be a physical association between the RNA and the particular target nucleic acid such as, but not limited to, in an RNA or ribonucleoprotein complex. This association can also be within the context of a biological pathway, such as but not limited to, the regulation of expression levels of a protein encoding mRNA or its precursor by a small untranslated RNA. As such, the invention provides for modulation of a target nucleic acid where the target nucleic acid is a messenger RNA whose expression is regulated by small untranslated RNAs. The messenger RNA function or processing is disrupted by degradation through an antisense mechanism, including but not limited to, RNA interference, RNase H, as well as other mechanisms wherein double stranded nucleic acid structures are recognized and degraded, cleaved or otherwise rendered inoperable.

The compounds or compositions of the present invention may also interfere with the function of RNA. The functions of RNA to be interfered with can include nuclear events such as replication or transcription as the compounds of the present invention could target or mimic small untranslated RNA components in these cellular processes. Replication and transcription, for example, can be from an endogenous cellular template, a vector, a plasmid construct or otherwise. The functions of RNA to be interfered with can include cytoplasmic events such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA as the compounds of the present invention could target or mimic small untranslated RNA components in these cellular processes.

The present invention provides, inter alia, oligomeric compounds and compositions containing the same wherein the oligomeric compound includes one or more modifications that render the compound capable of supporting modulation of the expression or function of the nucleic acid target by a degradation or cleavage mechanism.

The present invention also provides oligomeric compounds and compositions containing the same wherein the oligomeric compound includes one or more modifications that render the compound capable of blocking or interfering with the expression or function of the nucleic acid target by steric occlusion.

The present invention also provides oligomeric compounds and compositions containing the same wherein the oligomeric compound includes one or more modifications or structural elements or motifs that render the compound capable of mimicking or replacing the nucleic acid target.

In the context of the present invention, the term "oligomeric compounds" refers to polymeric structures which are capable of hybridizing to at least a region of a nucleic acid targetmolecule or compounds which are capable of mimicking nucleic acid targets. This term includes, but is not limited to, oligonucleotides, oligonucleosides, oligonucleotide analogs, oligonucleotide mimetics and combinations of these. Oligomeric compounds are routinely prepared linearly but can be joined or otherwise prepared to be circular and may also include branching. Separate oligomeric compounds can hybridize to form double stranded compounds that can be blunt-ended or may include overhangs. In general, an oligomeric compound comprises a backbone of linked momeric subunits where each linked momeric subunit is directly or indirectly attached to a heterocyclic base moiety. The linkages joining the monomeric subunits, the sugar moieties or sugar surrogates and the heterocyclic base moieties can be independently modified giving rise to a plurality of motifs for the resulting oligomeric compounds including hemimers, gapmers and chimeras.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. In addition, linear compounds may have internal nucleobase complementarity and may therefore fold in a manner as to produce a fully or partially double-stranded structure. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers generally to an oligomer or polymer of ribonucleic acid (RNA) or deoxyribonucleic acid (DNA). This term includes oligonucleotides composed of naturally occurring nucleobases, sugars and covalent internucleoside linkages. The term "oligonucleotide analog" refers to oligonucleotides that have one or more non-naturally occurring portions which function in a similar manner to oligonucleotides. Such non-naturally occurring oligonucleotides are often selected over naturally occurring forms because of desirable properties such as, for example, enhanced cellular uptake, enhanced affinity for other oligonucleotides or nucleic acid targets and increased stability in the presence of nucleases.

In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

In addition to the modifications described above, the nucleosides of the oligomeric compounds of the invention can have a variety of other modifications. For nucleotides that are incorporated into oligonucleotides of the invention, these nucleotides can have sugar portions that correspond to naturally occurring sugars or modified sugars. Representative modified sugars include carbocyclic or acyclic sugars, sugars having substituent groups at one or more of their 2', 3' or 4' positions and sugars having substituents in place of one or more hydrogen atoms of the sugar. Additional nucleosides amenable to the present invention having altered base moieties and or altered sugar moieties are disclosed in U.S. Pat. No. 3,687,808 and PCT application PCT/US89/02323.

Altered base moieties or altered sugar moieties also include other modifications consistent with the spirit of this invention. Such oligonucleotides are best described as being structurally distinguishable from, yet functionally interchangeable with, naturally occurring or synthetic wild type oligonucleotides. All such oligonucleotides are comprehended by this invention so long as they function effectively to mimic the structure or function of a desired RNA or DNA strand. A class of representative base modifications include tricyclic cytosine analog, termed "G clamp" (Lin et al., J. Am. Chem. Soc., 1998, 120, 8531). This analog makes four hydrogen bonds to a complementary guanine (G) within a helix by simultaneously recognizing the Watson-Crick and Hoogsteen faces of the targeted G. This G clamp modification when incorporated into phosphorothioate oligonucleotides, dramatically enhances antisense potencies in cell culture. The oligonucleotides of the invention also can include phenoxazine-substituted bases of the type disclosed by Flanagan et al. (Nat. Biotechnol., 1999, 17, 48-52).

The oligomeric compounds in accordance with this invention can comprise from about 8 to about 80 nucleobases (i.e. from about 8 to about 80 linked nucleosides). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length, or any range therewithin.

In another embodiment, the oligomeric compounds of the invention are 12 or 13 to 50 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length, or any range therewithin.

In another embodiment, the oligomeric compounds of the invention are 15 to 30 nucleobases in length. One having ordinary skill in the art will appreciate that this embodies oligomeric compounds of 15, 16, 17, 18, 19, 20, 21, 22, 23, 24, 25, 26, 27, 28, 29, or 30 nucleobases in length, or any range therewithin.

In another embodiment, the oligomeric compounds of the invention are 17 to 25 nucleobases in length. One having ordinary skill in the art will appreciate that this embodies oligomeric compounds of 17, 18, 19, 20, 21, 22, 23, 24, or 25 nucleobases in length, or any range therewithin.

In another embodiment, the oligomeric compounds of the invention are 18 to 24 nucleobases in length. One having ordinary skill in the art will appreciate that this embodies oligomeric compounds of 18, 19, 20, 21, 22, 23, or 24 nucleobases in length, or any range therewithin.

In some embodiments, the oligomeric compounds of the invention are 10 to 50 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length, or any range therewithin.

In other embodiments, the oligomeric compounds of the invention are 12 to 30 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, or 30 nucleobases in length, or any range therewithin.

In other embodiments, the oligomeric compounds of the invention are 12 to 24 nucleobases in length. One having ordinary skill in the art will appreciate that this embodies oligomeric compounds of 12, 13, 14, 15, 16, 17, 18, 19, 20, 21, 22, 23 or 24 nucleobases in length, or any range therewithin.

The present invention also provides methods of identifying at least one sequence motif within a family of similarly-regulated genes, wherein the oligomeric compound is used to inhibit expression of a target nuclear receptor/transcription factor and thereby modulate expression of at least one member of the gene family, and wherein microarray analysis is used to observe a change in the gene expression profile.

In the context of the present invention, "modulation" and "modulation of expression" mean either an increase (stimulation or up-regulation) or a decrease (inhibition or down-regulation) in the amount or levels of a nucleic acid target or the subsequent increase or decrease of a downstream target of the nucleic acid target e.g., reduction of mRNA levels of a protein coding nucleic acid that is regulated by any nucleic acid target that is amenable to targeting with the compounds of the present invention. Inhibition is a suitable form of modulation and small non-coding RNA or gene regulatory sequences such as promoters or enhancers are suitable nucleic acid targets. In the context of the present invention, "modulation of function" means an alteration in the function of the nucleic acid target or an alteration in the function of any cellular component with which the nucleic acid target has an association.

The present invention also provides a method wherein two or more computer algorithms are used to identify at least one conserved regulatory region in a gene family for which the expression was modulated by treatment with the oligomeric compound. In some embodiments, the computer algorithms may be a MEME algorithm, a HMMER algorithm, or a TFBIND algorithm, or any combination thereof.

As used herein, "microarray analysis" refers to the use of ordered sets of multiple nucleic acids fixed to solid surfaces in for experiments involving incubation with pools of unfixed, nucleic acids, and detection of hybridization reactions, as well as the accompanying analysis and data interpretation using computer software. Microarray analysis can be used to assess the presence or absence of a nucleic acid within a pool of nucleic acid sequences, and can thereby be used to determine, for example, the expression profile of genes under active transcription at a given time point or period.

The term "computer algorithm" means a set of instructions that a computer is to execute before arriving at an end goal of data output. Computer algorithms enable the analysis of sequences by comparing, editing, mapping and/or aligning sequences, often with respect to a query or master sequence (nucleotide or protein), and result in identification and ranking of related sequences from the database of input sequences. Sequence similarity search algorithms, as a non-limiting example, calculate a quantitative measure of similarity for each result compared with a master sequence. An example of a quantitative result is an E-value obtained from the BLAST algorithm (accessible through the Internet at, for example, www(dot)ncbi(dot)nlm(dot)nih(dot)gov/BLAST/); the E-value is the probability that a match between a query sequence and a database sequence occurs due to random chance. Therefore, the lower an E-value the more likely that two sequences are truly related.

Software and computer algorithms used for promoter characterization may include: Gene Regulation (accessible through the Internet at, for example, www(dot)gene-regulation(dot)com); Melina—Motif Elucidator in Nucleotide Sequence Assembly (accessible through the Internet at, for example, Melina(dot)hgc(dot)jp/); MEME—Multiple EM for Motif Elicitation (accessible through the Internet at, for example, meme(dot)sdsc(dot)edu/meme/website/meme(dot)html); TFBIND—Transcription Factor Binding program (accessible through the Internet at, for example, tfbind(dot)ims(dot)u-tokyo(dot)ac(dot)jp/); GenomeVista—(accessible through the Internet at, for example, pipeline(dot)lbl(dot)gov/cgi-bin/GenomeVista); and GeneSpring—(accessible through the Internet at, for example, www(dot)silicongenetics(dot)com/cgi/SiG(dot)cgi/index(dot)smf). "MEME" or "MAST/MEME" refers to a computer algorithm by which conserved motifs in a group of unaligned sequences are identified. MAST is a tool for searching biological sequence databases for sequences that contain one or more of a group of known motifs. A motif is a sequence pattern that occurs repeatedly in a group of related protein or DNA sequences. Motifs are represented as position-dependent scoring matrices that describe the score of each possible letter at each position in the pattern. Individual motifs may not contain gaps. Patterns with variable-length gaps must be split into two or more separate motifs before being submitted as input to MAST. MAST takes as input a file containing the descriptions of one or more motifs and searches a sequence database selected for sequences that match the motifs. The motif file can be the output of the MEME motif discovery tool or any file in the appropriate format. MEME saves these motifs as a set of profiles. MEME was written by Dr. Timothy L. Bailey of the San Diego Supercomputing Center and uses the method of Bailey and Elkan (Bailey et al., Proc. Second Int'l Con. Intelligent Systems Mol. Biol., 1994, 28-36, AAAI Press, Menlo Park, Calif.) to identify and characterize likely motifs within a family of sequences from an input set of sequences. A range of motif widths to target may be specified, as well as the number of unique motifs to search for. MEME uses Bayesian probability to incorporate prior knowledge of the similarities among amino acids into its predictions of likely motifs. The resulting motifs are output as profiles. A profile is a log-odds matrix used to judge how well an unknown sequence segment matches the motif. Sequences that meet the cutoff criteria are selected for more detailed comparisons according to a set of rules described below. Since an objective of the sequence similarity search to find distantly related orthologs and paralogs, it is desirable that the cutoff criteria not be too stringent, or the target of the search may be excluded.

"HMMER" refers to a freely distributable software suite for making and using Hidden Markov Models (HMMs) of biological sequences. HMMs are statistical models of the primary structure consensus of a sequence family. Anders Krogh, David Haussler, and co-workers at UC Santa Cruz introduced a form of HMM which was well-suited to protein and DNA sequence analysis, adopting HMM techniques which have been used for years in speech recognition. HMMER is a freely distributable implementation of profile HMM software for protein sequence analysis, and includes a computer algorithm by which profile hidden Markov models (profile HMMs) can be used to do sensitive database searching using statistical descriptions of a sequence family's consensus.

"TFBIND" refers to a promoter prediction software program for searching transcription factor binding sites (including TATA boxes, GC boxes, CCAAT boxes, transcription start sites (TSS)). This tool uses weight matrix in transcription factor database TRANSFAC.

The invention also provides methods of treating or preventing a disease or disorder associated with aberrant adipocyte differentiation comprising contacting an animal having or predisposed to the disease or disorder with a therapeutically effective amount of the oligomeric compound. This method may further comprise identifying the animal having or predisposed to the disease or disorder prior to treatment or prevention. In some embodiments, the disease or disorder may be a hyperproliferative condition such as cancer, neoplasia, or angiogenesis. In some embodiments, the disease or disorder may be a metabolic disease, such as obesity or diabetes.

The invention also provides a method of screening for a sequence motif within a family of similarly-regulated genes comprising contacting a nucleic acid target with an oligomeric compound, assaying the effects of the oligomeric compound on adipocyte differentiation, assaying the effects of the oligomeric compound on the expression profile of downstream genes by microarray analyses, identifying two or more downstream genes exhibiting a change in expression meeting a predefined threshold of increased or decreased RNA levels, comparing the regulatory sequences of the two or more downstream genes, and identifying conserved sequence motifs that meet a predefined threshold of nucleic acid sequence conservation.

The invention also provides a kit or assay device comprising the oligomeric compound or pharmaceutical composition.

In the context of this invention, "hybridization" means the pairing of complementary strands of oligomeric compounds. In the present invention, the mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases that pair through the formation of hydrogen bonds. Hybridization can occur under varying circumstances.

An oligomeric compound of the invention is specifically hybridizable when binding of the compound to the target nucleic acid interferes with the normal function of the target nucleic acid to cause a loss of activity or disruption of function, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which an oligomeric compound of the invention will hybridize to its target sequence, but to a minimal number of other sequences. Stringent conditions are sequence-dependent and will vary with different circumstances and in the context of this invention; "stringent conditions" under which oligomeric compounds hybridize to a target sequence are determined by the nature and composition of the oligomeric compounds and the assays in which they are being investigated.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, then the position of hydrogen bonding between the oligonucleotide and the target nucleic acid is considered to be a complementary position. The oligomeric compound and the target nucleic acid are complementary to each other when a sufficient number of complementary positions in each molecule are occupied by nucleobases that can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of the oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure).

In some embodiments of the invention, the oligomeric compounds comprise at least about 70%, at least about 75%, at least about 80%, at least about 85%, at least about 90%, at least about 95%, at least about 99%, or 100% sequence complementarity to a target region within the target nucleic acid. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang et al., Genome Res., 1997, 7, 649-656).

In some embodiments of the invention, the oligomeric compounds act as mimics or replacements for target nucleic acids. In this case, the oligomeric compounds of the invention can comprise at least about 70%, at least about 75%, at least about 80%, at least about 85%, at least about 90%, at least about 95%, at least about 99%, or 100% sequence identity to a target nucleic acid or a region thereof.

"Targeting" an oligomeric compound to a particular nucleic acid molecule, in the context of this invention, can be a multistep process. The process usually begins with the identification of a target nucleic acid whose function is to be modulated. This target nucleic acid may be, for example, a mRNA transcribed from a cellular gene whose expression is associated with a particular disorder or disease state, a small untranslated RNA or its precursor, or a nucleic acid molecule from an infectious agent.

The targeting process usually also includes determination of at least one target region, segment, or site within the target nucleic acid for the interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid. The terms region, segment, and site can also be used to describe an oligomeric compound of the invention such as for example a gapped oligomeric compound having three separate segments.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a nucleic acid target, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense oligomeric compounds of the present invention.

The open reading frame (ORF) or "coding region," which is known in the art to refer to the region between the translation initiation codon and the translation termination codon, is also a region which may be targeted effectively. Within the context of the present invention, a suitable region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also suitable to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also target sites. mRNA transcripts produced via the process of splicing of two (or more) mRNAs from different gene sources are known as "fusion transcripts." It is also known that introns can be effectively targeted using oligomeric compounds targeted to, precursor molecules for example, pre-mRNA.

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequences.

Upon excision of one or more exon or intron regions, or portions thereof during splicing, pre-mRNA variants produce smaller "mRNA variants." Consequently, mRNA variants are processed pre-mRNA variants and each unique pre-mRNA variant must always produce a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also target nucleic acids.

Untranslated RNA genes are known to produce functional RNA molecules with important roles in diverse cellular processes; such untranslated RNA targets can include ribosomal RNAs, tRNAs, snRNAs, snoRNAs, tncRNAs, short temporal RNAs (stRNAs), rasiRNAs, siRNAs, miRNAs and smRNAs, and such cellular processes include transcriptional regulation, translational regulation, developmental timing, viral surveillance, immunity, chromosome maintenance, ribosomal structure and function, gene imprinting, subcellular compartmentalization, pre-mRNA splicing, and guidance of RNA modifications. RNA-mediated processes are now also believed to direct heterochromatin formation, genome rearrangements, cellular differentiation and DNA elimination.

A total of 201 different expressed RNA sequences potentially encoding novel small non-messenger species (smRNAs) has been identified from mouse brain cDNA libraries. Based on sequence and structural motifs, several of these have been assigned to the snoRNA class of nucleolar localized molecules known to act as guide RNAs for rRNA modification, whereas others are predicted to direct modification within the U2, U4, or U6 small nuclear RNAs (snRNAs). Some of these newly identified smRNAs remained unclassified and have no identified RNA targets. It was suggested that some of these RNA species may have novel functions previously unknown for snoRNAs, namely the regulation of gene expression by binding to and/or modifying mRNAs or their precursors via their antisense elements (Huttenhofer et al., EMBO J., 2001, 20, 2943-53).

The locations on the target nucleic acid to which suitable compounds and compositions of the invention hybridize are herein below referred to as "suitable target segments." As used herein the term "suitable target segment" is defined as at least an 8-nucleobase portion of a target region to which oligomeric compound is targeted.

Once one or more target regions, segments or sites have been identified, oligomeric compounds are chosen which are sufficiently complementary to the target, i.e., hybridize sufficiently well and with sufficient specificity, to give the desired effect.

In accordance with an embodiment of the invention, a series of single stranded oligomeric compounds of the present invention can be designed for a specific nucleic acid target or targets. These oligomeric compounds can be of a specified length, for example from 8 to 80, 12 to 50 or 15 to 30 nucleotides long, or any range disclosed herein, and have one or more modifications.

In some embodiments, the oligomeric compounds are targeted to a nucleic acid molecule encoding PPAR-γ (SEQ ID NO:4). In other embodiments, the oligomeric compounds are targeted to a nucleic acid molecule encoding human F1120920 (SEQ ID NO:29).

In some embodiments, the oligomeric compounds are targeted to or not targeted to particular regions of SEQ ID NO:4 such as, for example, nucleobases 1-50, 51-100, 101-150, 151-200, 201-250, 251-300, 301-350, 351-400, 401-450, 451-500, 501-550, 551-600, 601-650, 651-700, 701-750, 751-800, 801-850, 851-900, 901-950, 951-1000, 1001-1050, or 1051-1100, or any combination thereof.

In some embodiments, the oligomeric compounds are targeted to or not targeted to particular regions of SEQ ID NO:29 such as, for example, nucleobases 1-50, 51-100, 101-150, 151-200, 201-250, 251-300, 301-350, 351-400, 401-450, 451-500, 501-550, 551-600, 601-650, 651-700, 701-750, 751-800, 801-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, 2001-2050, 2051-2100, 2101-2150, or 2151-2161, or any combination thereof.

In accordance with an embodiment of the invention, a series of nucleic acid duplexes comprising as the antisense strand, the single stranded oligomeric compounds of the present invention and its complement sense strand. These compounds can be designed to modulate the expression or function of specific nucleic acid target or targets. The ends of the strands may be modified by the addition of one or more natural or modified nucleobases to form an overhang. The sense strand of the duplex is designed and synthesized as the complement of the antisense strand and may also contain modifications or additions to either terminus. For example, in one embodiment, both strands of the duplex would be complementary over the central nucleobases, each having overhangs at one or both termini.

For the purposes of describing an embodiment of this invention, the combination of an antisense strand and a sense strand, each of which can be of a specified length, for example from 8 to 80, 12 to 50 or 15 to 30 nucleotides long, is identified as a complementary pair of oligonucleotides. These complementary pair of oligonucleotides can include additional nucleotides on either of their 5' or 3' ends. Further they can include other molecules or molecular structures on their 3' or 5' ends such as a phosphate group on the 5' end. One group of compounds of the invention includes a phosphate group on the 5' end of the antisense strand compound. Other compounds also include a phosphate group on the 5' end of the sense strand compound. Further compounds would include additional nucleotides such as a two base overhang on the 3' end as well as those lacking overhangs.

For example, a complementary pair of oligonucleotides may comprise an antisense strand oligomeric compound having the sequence CGAGAGGCGGACGGGACCG (SEQ ID NO:6), having a two-nucleobase overhang of deoxythymidine(dT) and its complement sense strand. These oligonucleotides would have the following structure:

```
cgagaggcggacgggaccgTT   (SEQ ID NO:7)
|||||||||||||||||||     Antisense Strand
TTgctctccgcctgccctggc   (SEQ ID NO:8)
                        Complement Sense Strand
```

In an additional embodiment of the invention, a single oligomeric compound having both the antisense portion as a first region in the oligonucleotide and the sense portion as a second region in the oligonucleotide is selected. The first and second regions are linked together by either a nucleotide linker (a string of one or more nucleotides that are linked together in a sequence) or by a non-nucleotide linker region or by a combination of both a nucleotide and non-nucleotide structure. In each of these structures, the oligonucleotide, when folded back on itself, would form at least a partially complementary structure at least between a portion of the first region, the antisense portion, and a portion of the second region, the sense portion. Thus, the oligonucleotide would have a palindrome within it structure wherein the first region, in the 5' to 3' direction, is complementary to the second region, in the 3' to 5' direction.

In a further embodiment, the invention includes an oligonucleotide/protein composition. This composition has both an oligonucleotide component and a protein component. The oligonucleotide component comprises at least one oligonucleotide, either the antisense or the sense oligonucleotide but often the antisense oligonucleotide (the oligonucleotide that is antisense to the target nucleic acid). The protein component of the composition comprises at least one protein that forms a portion of the RNA-induced silencing complex, i.e., the RISC complex. The oligonucleotide component can also comprise both antisense and sense strand oligonucleotides.

RNA interference is a process of transcriptional or posttranscriptional gene silencing involving antisense RNA molecules which hybridize to target nucleic acid sequences and cause either degradation of the target nucleic acid or translational inhibition by steric interference, or both. RISC is a ribonucleoprotein complex that contains proteins of the Argonaute family of proteins. While not desiring to be bound by theory, the Argonaute proteins are a class of proteins, some of which have been shown to contain a PAZ and/or a Piwi domain and that have been implicated in processes previously linked to posttranscriptional silencing. The Argonaute family of proteins includes, but depending on species, are not necessary limited to elF2C1 and elF2C2. elF2C1 is also known as human GERp95. While not desiring to be bound by theory, at least the antisense oligonucleotide strand is bound to one of the protein components that form the RISC complex. Additionally, the complex might also include the sense strand oligonucleotide.

Also while not desiring to be bound by theory, it is further believed that the RISC complex interacts with the ribosomes or polyribosome complex which may contain small untranslated RNA molecules amenable to targeting with the compounds of the present invention.

In one embodiment of the invention is included an oligomeric compound that mimics RNA components of the RISC complex.

In yet further embodiments of the invention, the oligonucleotide of the invention can be associated with cellular factors such as transporters or chaperones. These cellular factors can be protein, lipid or carbohydrate based and can have structural or enzymatic functions that may or may not require the complexation of one or more metal ions.

Furthermore, the oligonucleotides of the invention itself can have one or more moieties that are bound to the oligonucleotide which facilitates the active or passive transport, localization, or compartmentalization of the oligonucleotide. Cellular localization includes, but is not limited to, localization to within the nucleus, the nucleolus, or the cytoplasm. Compartmentalization includes, but is not limited to, any directed movement of the oligonucleotides of the invention to a cellular compartment including the nucleus, nucleolus, mitochondrion, or imbedding into a cellular membrane surrounding a compartment or the cell itself.

In yet further embodiments of the invention, the oligomeric compounds of the invention is associated with cellular factors that affect gene expression, more specifically those involved in RNA or DNA modifications. These modifications include, but are not limited to, posttranscriptional or chromosomal modifications such as phosphorylation, methylation, acetylation, pseudouridylation or amination.

Furthermore, the oligonucleotide of the invention itself can have one or more moieties which are bound to the oligonucleotide and facilitate the posttranscriptional modification.

The oligomeric compounds of the invention may be used in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or proteins to effect modification of the target nucleic acid.

One non-limiting example of such a protein is the RISC complex. Use of the RISC complex to effect cleavage of RNA targets thereby greatly enhances the efficiency of oligonucleotide-mediated inhibition of gene expression. Similar roles have been postulated for other ribonucleases such as those in the RNase III and ribonuclease L family of enzymes.

Oligomeric compounds of the invention include a single-stranded oligonucleotide that binds in a RISC complex, a double stranded antisense/sense pair of oligonucleotides or a single strand oligonucleotide that includes both an antisense portion and a sense portion. Each of these compounds or compositions is used to induce potent and specific modulation of gene function through interactions with or mimicry of small untranslated RNAs that are involved in gene modulation.

Such specific modulation of gene function has been shown in many species by the introduction of double-stranded structures, such as double-stranded RNA (dsRNA) molecules and has been shown to induce potent and specific antisense-mediated reduction of the function of a gene or its associated gene products. This phenomenon occurs in both plants and animals and is believed to have an evolutionary connection to viral defense and transposon silencing.

The compounds and compositions of the invention are used to modulate the expression or function of a target nucleic acid. "Modulators" are those oligomeric compounds that either increase (stimulate or up-regulate) or a decrease (inhibit or down-regulate) the amount, levels or activity of a nucleic acid target or that subsequently increase or decrease levels of a downstream target of the target nucleic acid e.g., reduction of mRNA levels of a protein coding nucleic acid that is regulated by a small untranslated RNA that is amenable to targeting with the compounds of the present invention. In the context of the present invention, a "modulator of function" is an oligomeric compound that causes an alteration in the function of the nucleic acid target or an alteration in the function of any cellular component with which the nucleic acid target has an association.

Screening methods for the identification of effective modulators of target nucleic acids are also comprehended by the instant invention and comprise the steps of contacting a target nucleic acid molecule, or portion thereof, with one or more candidate modulators, and selecting for one or more candidate modulators which decrease or increase the expression or alter the function of the target nucleic acid. Once it is shown that the candidate modulator or modulators are capable of modulating (e.g. either decreasing or increasing) the expression or altering the function of the target nucleic acid, the modulator may then be employed in further investigative studies of the target, or for use as a research, diagnostic, or therapeutic agent in accordance with the present invention.

Screening methods for the identification of suitable nucleic acid target mimics are also within the scope of the invention.

Oligomerization of modified and unmodified nucleosides is performed according to literature procedures for DNA like compounds (Protocols for Oligonucleotides and Analogs, Ed. Agrawal (1993), Humana Press) and/or RNA like compounds (Scaringe, Methods, 2001, 23, 206-217; Gait et al., Applications of Chemically synthesized RNA in RNA:Protein Interactions, Ed. Smith (1998), 1-36; and Gallo et al., Tetrahedron, 2001, 57, 5707-5713) synthesis as appropriate. In addition specific protocols for the synthesis of oligomeric compounds of the invention are illustrated in the examples below.

RNA oligomers can be synthesized by methods disclosed herein or purchased from various RNA synthesis companies such as for example Dharmacon Research Inc., (Lafayette, Colo.).

Irrespective of the particular protocol used, the oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

For double stranded compounds of the invention, once synthesized, the complementary strands are annealed. The single strands are aliquoted and diluted to a concentration of 50 µM. Once diluted, 30 µL of each strand is combined with 15 µL of a 5× solution of annealing buffer. The final concentration of the buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA compound is 20 µM. This solution can be stored frozen (−20° C.) and freeze-thawed up to 5 times. Once prepared, the desired synthetic duplexes are evaluated for their ability to modulate target expression or function. When cells reach 80% confluency, they are treated with synthetic duplexes comprising at least one oligomeric compound of the invention. For cells grown in 96-well plates, wells are washed once with 200 µL OPTI-MEM-1 reduced-serum medium (Gibco BRL) and then treated with 130 µL of OPTI-MEM-1 containing 12 µg/mL LIPOFECTIN™ (Invitrogen Corporation, Carlsbad, Calif.) and the desired double stranded compound at a final concentration of 200 nM. After 5 hours of treatment, the medium is replaced with fresh medium. Cells are harvested 16 hours after treatment, at which time RNA is isolated and target reduction measured by RT-PCR.

Specific examples of oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain oligomeric compounds of the invention can also have one or more modified internucleoside linkages. A suitable phosphorus-containing modified internucleoside linkage is the phosphorothioate internucleoside linkage.

Modified oligonucleotide backbones (internucleoside linkages) containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In other embodiments of the invention, oligomeric compounds have one or more phosphorothioate and/or heteroatom internucleoside linkages, such as, for example, —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). The MMI type internucleoside linkages are disclosed in the above referenced U.S. Pat. No. 5,489,677. Further amide internucleoside linkages are disclosed in the above referenced U.S. Pat. No. 5,602,240.

Modified oligonucleotide backbones (internucleoside linkages) that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Another group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA oligomeric compounds include, but are not limited to, U.S. Pat. Nos. 5,539,082; 5,714,331; and 5,719,262. Further teaching of PNA oligomeric compounds can be found in Nielsen et al., Science, 1991, 254, 1497-1500.

PNA has been modified to incorporate numerous modifications since the basic PNA structure was first prepared. The basic structure is shown below:

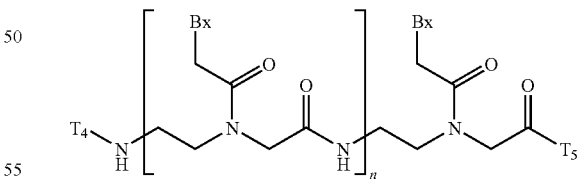

wherein
Bx is a heterocyclic base moiety;
T$_4$ is hydrogen, an amino protecting group, —C(O)R$_5$, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;

each J is O, S or NH;

$R_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A suitable class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Braasch et al., Biochemistry, 2002, 41, 4503-4510). Morpholino-based oligomeric compounds are disclosed in U.S. Pat. No. 5,034,506. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

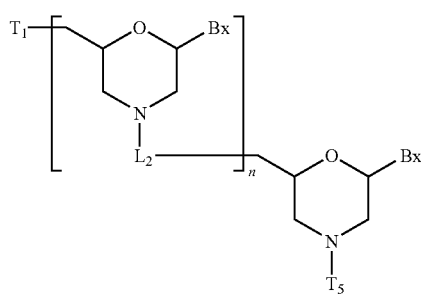

wherein $T_1$ is hydroxyl or a protected hydroxyl;

$T_5$ is hydrogen or a phosphate or phosphate derivative;

$L_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclohexyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. coli* RNase resulting in cleavage of the target RNA strand.

The general formula of CeNA is shown below:

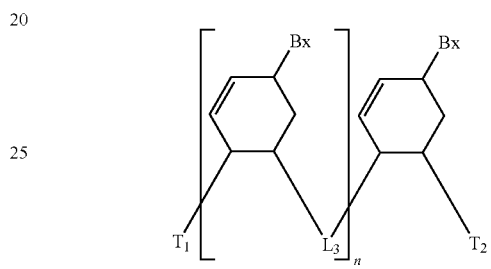

wherein each Bx is a heterocyclic base moiety;

$T_1$ is hydroxyl or a protected hydroxyl; and $T_2$ is hydroxyl or a protected hydroxyl.

Another class of oligonucleotide mimetic (anhydrohexitol nucleic acid) can be prepared from one or more anhydrohexitol nucleosides (see, Wouters et al., Bioorg. Med. Chem. Lett., 1999, 9, 1563-1566) and would have the general formula:

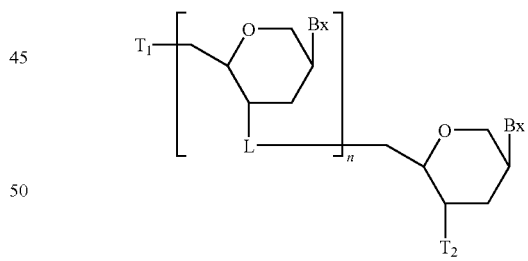

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH$_2$—)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA ($T_m$=+3 to +10° C.), stability towards 3'-exonucleolytic degradation and good solubility properties. The basic structure of LNA showing the bicyclic ring system is shown below:

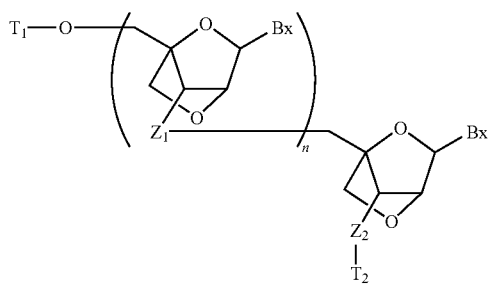

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points ($T_m$=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligonucleotides containing LNAs have been described (Wahlestedt et al., Proc. Natl. Acad. Sci. U.S.A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in E. coli. LIPOFECTIN™-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (PCT International Application WO 98-DK393 19980914). Furthermore, synthesis of T-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNAs have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

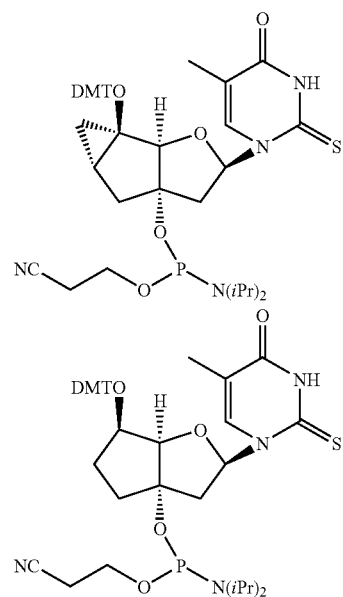

(see Steffens et al., Helv. Chim. Acta, 1997, 80, 2426-2439; Steffens et al., J. Am. Chem. Soc., 1999, 121, 3249-3255; and Renneberg et al., J. Am. Chem. Soc., 2002, 124, 5993-6002). These modified nucleoside analogs have been oligomerized using the phosphoramidite approach and the resulting oligomeric compounds containing tricyclic nucleoside analogs have shown increased thermal stabilities ($T_m$s) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acid and incorporates a phosphorus group in the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346) is shown below.

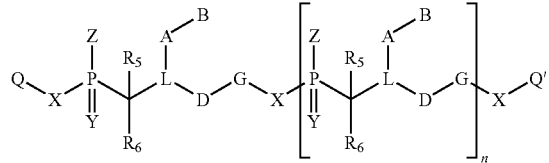

Another oligonucleotide mimetic has been reported wherein the furanosyl ring has been replaced by a cyclobutyl moiety.

Oligomeric compounds of the invention may also contain one or more substituted sugar moieties. These oligomeric compounds comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)OCH_3$, $O(CH_2)_nNH_2$, $O(CH_2)_nCH_3$, $O(CH_2)ONH_2$, and $O(CH_2)_nON((CH_2)_nCH_3)_2$, where n and m are from 1 to about 10. Further oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy(2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. Another modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro(F). 2'-Sugar substituent groups may be in the arabino (up) position or ribo (down) position. One 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920.

Additional representative sugar substituent groups include groups of formula $I_a$ or $II_a$:

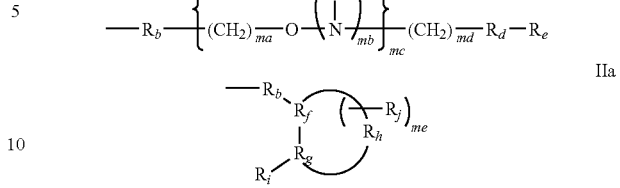

wherein:

Rb is O, S or NH;

Rd is a single bond, O, S or C(=O);

$R_e$ is $C_1$-$C_{10}$ alkyl, $N(R_k)(R_m)$, $N(R_k)(R_n)$, N=$C(R_p)(R_q)$, N=$C(R_p)(R_r)$ or has formula $III_a$;

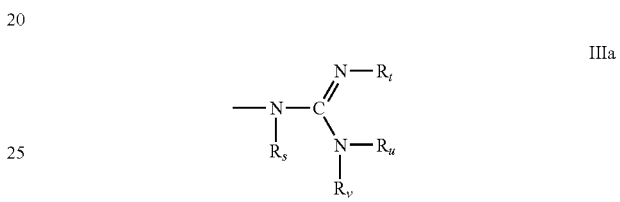

$R_p$ and $R_q$ are each independently hydrogen or $C_1$-$C_{10}$ alkyl;

$R_r$ is —$R_x$—$R_y$;

each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

$R_k$ is hydrogen, a nitrogen protecting group or —$R_x$—$R_y$;

$R_p$ is hydrogen, a nitrogen protecting group or —$R_x$—$R_y$;

$R_x$ is a bond or a linking moiety;

$R_y$ is a chemical functional group, a conjugate group or a solid support medium;

each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_i$ is $OR_z$, $SR_z$, or $N(R_z)_2$;

each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN;

$m_a$ is 1 to about 10;

each mb is, independently, 0 or 1;

mc is 0 or an integer from 1 to 10;

md is an integer from 1 to 10;

me is from 0, 1 or 2; and provided that when mc is 0, md is greater than 1.

Representative substituents groups of Formula I are disclosed in U.S. Pat. No. 6,172,209.

Representative cyclic substituent groups of Formula II are disclosed in U.S. Pat. No. 6,271,358.

Particular sugar substituent groups include $O((CH_2)_nO)_m CH_3$, $O(CH_2)_nOCH_3$, $O(CH_2)_nNH_2$, $O(CH_2)_nCH_3$, $O(CH_2)_n ONH_2$, and $O(CH_2)_nON((CH_2)_aCH_3))_2$, where n and m are from 1 to about 10.

Representative guanidino substituent groups that are shown in formula III and IV are disclosed in U.S. Pat. No. 6,593,466.

Representative acetamido substituent groups are disclosed in U.S. Pat. No. 6,147,200.

Representative dimethylaminoethyloxyethyl substituent groups are disclosed in International Patent Application PCT/US99/17895, entitled "2'-O-Dimethylaminoethyloxy-ethyl-Oligomeric compounds", filed Aug. 6, 1999.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag). Modification of the 2' position to favor the 3'-endo conformation can be achieved while maintaining the 2'-OH as a recognition element (Gallo et al., Tetrahedron, 2001, 57, 5707-5713; Harry-O'kuru et al., J. Org. Chem., 1997, 62, 1754-1759; and Tang et al., J. Org. Chem., 1999, 64, 747-754). Alternatively, preference for the 3'-endo conformation can be achieved by deletion of the 2'-OH as exemplified by 2' deoxy-2'F-nucleosides (Kawasaki et al., J. Med. Chem., 1993, 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters, 1995, 5, 1455-1460 and Owen et al., J. Org. Chem., 1976, 41, 3010-3017), or for example modification to yield methanocarba nucleoside analogs (Jacobson et al., J. Med. Chem. Lett., 2000, 43, 2196-2203 and Lee et al., Bioorganic and Medicinal Chemistry Letters, 2001, 11, 1333-1337) also induce preference for the 3'-endo conformation.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

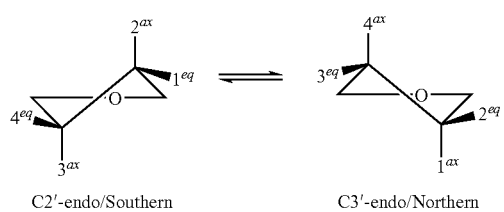

Scheme 1

C2'-endo/Southern    C3'-endo/Northern

Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76). Examples of modified nucleosides amenable to the present invention are shown below in Table 1. These examples are meant to be representative and not exhaustive.

TABLE 1

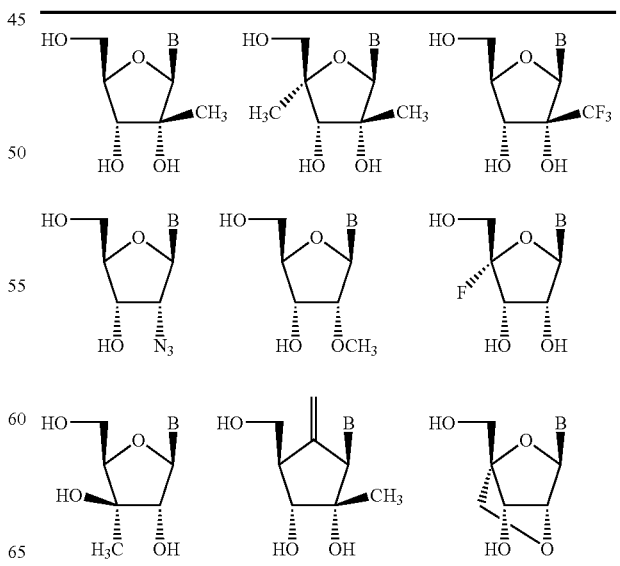

TABLE 1-continued

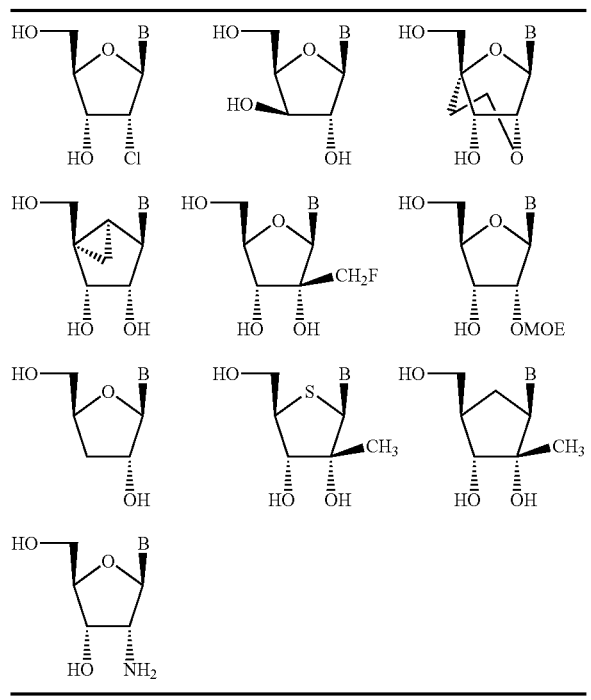

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2 aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S.T. and Lebleu, B., eds., *Antisense Research and Applications*, CRC Press, Boca Raton, 1993, pp. 276-278) and are presently suitable base substitutions, even more particularly when combined with 2'-O-methoxyethyl sugar modifications.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

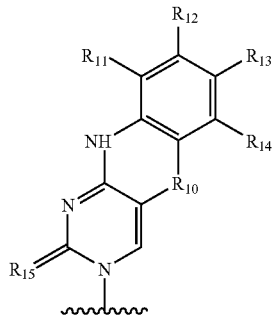

Representative cytosine analogs that make 3 hydrogen bonds with a guanosine in a second strand include 1,3-diazaphenoxazine-2-one ($R_{10}$=O, $R_{11}$-$R_{14}$=H) (Kurchavov et al., Nucleosides and Nucleotides, 1997, 16, 1837-1846), 1,3-diazaphenothiazine-2-one ($R_{10}$=S, $R_{11}$-$R_{14}$=H), (Lin et al., J. Am. Chem. Soc., 1995, 117, 3873-3874) and 6,7,8,9-tetrafluoro-1,3-diazaphenoxazine-2-one ($R_{10}$=O, $R_{11}$-$R_{14}$=F) (Wang et al., Tetrahedron Lett., 1998, 39, 8385-8388). When incorporated into oligonucleotides, these base modifications were shown to hybridize with complementary guanine and the latter was also shown to hybridize with adenine and to enhance helical thermal stability by extended stacking interactions (also see U.S. Patent Application Publication No. 20030207804; and U.S. Patent Application Publication No. 20030175906).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—(CH$_2$)$_2$—NH$_2$, $R_{12-14}$=H) (Lin et al., J. Am. Chem. Soc., 1998, 120, 8531-8532). Binding studies demonstrated that a single incorporation could enhance the binding affinity of a model oligonucleotide to its complementary target DNA or RNA with a ΔT$_m$, of up to 18° relative to 5-methyl cytosine (dC5$^{me}$), which is the highest known affinity enhancement for a single modification. On the other hand, the gain in helical stability does not compromise the specificity of the oligonucleotides. The T$_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. Nos. 6,028,183 and 6,007,992.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity (Lin et al., J. Am. Chem. Soc., 1998, 120, 8531-8532). The activity enhancement was even more pronounced in case of G-clamp, as a single substitution was shown to significantly improve the in vitro potency of a 20 mer 2'-deoxyphosphorothioate oligonucleotides (Flanagan et al., Nat. Biotechnol., 1999, 17, 48-52; Lin et al., J. Am. Chem. Soc., 1998, 120, 8531-8532; Wagner et al., Proc. Natl. Acad. Sci. USA, 1999, 96, 3513-3518). Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclic bases are disclosed in but not limited to, the above noted U.S. Pat. Nos. 3,687,808; 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. Patent Application Publication No. 20030158403.

A further substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, poly-ethylene glycols, polyethers, groups that enhance the pharmacodynamic properties of oligomers, and groups that enhance the pharmacokinetic properties of oligomers. Typical conjugates groups include cholesterols, carbohydrates, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., dihexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730.

Representative U.S. patents that teach the preparation of such oligonucleotide conjugates include, but are not limited to: 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

It is not necessary for all positions in an oligomeric compound to be uniformly modified, and in fact more than one of the aforementioned modifications may be incorporated in a single oligomeric compound or even at a single monomeric subunit such as a nucleoside within a oligomeric compound. The present invention also includes oligomeric compounds which are chimeric oligomeric compounds. "Chimeric" oligomeric compounds or "chimeras," in the context of this invention, are oligomeric compounds that contain two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide mimics, oligonucleotide analogs, oligonucleosides and/or oligonucleotide mimetics as described above. Such oligomeric compounds have also been referred to in the art as hybrids hemimers, gapmers or inverted gapmers. Representative U.S. patents that teach the preparation of such hybrid structures include, but are not limited to: 5,013,830; 5,149,797; 5,220,007; 5,256,775; 5,366,878; 5,403,711; 5,491,133; 5,565,350; 5,623,065; 5,652,355; 5,652,356; and 5,700,922.

The conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligoncleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum Press, and the examples section below.)

In one aspect, the present invention is directed to oligonucleotides that are prepared having enhanced properties compared to native RNA against nucleic acid targets. A target is identified and an oligonucleotide is selected having an effective length and sequence that is sufficiently complementary to a portion of the target sequence. Each nucleoside of the selected sequence is scrutinized for possible enhancing modifications. One modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonulceotide. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention may include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the desired property of the selected sequence for its intended target.

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott et al., Biochem. Biophys. Res. Comm., 1970, 47, 1504.) In general, RNA:RNA duplexes are more stable and have higher melting temperatures ($T_m$s) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., Nucleic Acids Research, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as but not limited to antisense mechanisms including RnaseH-mediated and RNA interference as these mechanisms require the hybridization of a synthetic sequence strand to an RNA target strand. In the case of RNaseH, effective inhibition of the mRNA requires that the antisense sequence achieve at least a threshold of binding affinity with the mRNA. Otherwise the desired interaction between the synthetic oligonucleotide strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependent on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

Unless otherwise defined herein, alkyl means $C_1$-$C_{12}$, $C_1$-$C_8$, or $C_1$-$C_6$, straight or (where possible) branched chain aliphatic hydrocarbyl.

Unless otherwise defined herein, heteroalkyl means $C_1$-$C_{12}$, $C_1$-$C_8$, or $C_1$-$C_6$, straight or (where possible) branched chain aliphatic hydrocarbyl containing at least one, and about 1 to about 3, hetero atoms in the chain, including the terminal portion of the chain. Suitable heteroatoms include N, O and S.

Unless otherwise defined herein, cycloalkyl means $C_3$-$C_{12}$, $C_3$-$C_8$, or $C_3$-$C_6$, aliphatic hydrocarbyl ring.

Unless otherwise defined herein, alkenyl means $C_2$-$C_{12}$, $C_2$-$C_8$, or $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, $C_2$-$C_8$, or $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. In some embodiments, the number of carbon atoms varies from 1 to about 12 or from 1 to about 6, and the total number of ring members varies from three to about 15, or from about 3 to about 8. Suitable ring heteroatoms are N, O and S. Suitable heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Suitable aryl rings have about 6 to about 20 ring carbons. Particular aryl rings include, but are not limited to, phenyl, napthyl, anthracenyl, and phenanthrenyl.

Unless otherwise defined herein, hetaryl means a ring moiety containing at least one fully unsaturated ring, the ring consisting of carbon and non-carbon atoms. In some embodiments, the ring system contains about 1 to about 4 rings. In some embodiments, the number of carbon atoms varies from 1 to about 12, or from 1 to about 6, and the total number of ring members varies from three to about 15, or from about 3 to about 8. Suitable ring heteroatoms are N, O and S. Suitable hetaryl moieties include, but are not limited to, pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Suitable halo (halogen) substituents are Cl, Br, and I.

The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate.

Phosphate protecting groups include those described in U.S. Pat. Nos. 5,760,209; 5,614,621; 6,051,699; 6,020,475; 6,326,478; 6,169,177; 6,121,437; 6,465,628.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see, for example, International PCT Publication No. WO 97/26270). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see International PCT Publication No. WO 97/26270).

Particularly suitable 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage et al., Tatrahedron, 1993, 49, 1925).

For use in screening and target validation, the compounds and compositions of the invention are used to modulate the expression or function of a selected nucleic acid target which may regulate the expression of one or more proteins. "Modulators" are those oligomeric compounds that either increase (stimulation) or a decrease (inhibition) the amount or levels of a nucleic acid target or that subsequently increase or decrease levels of a downstream target of the nucleic acid target e.g., reduction of mRNA levels of a protein coding nucleic acid that is regulated by any small untranslated RNA that is amenable to targeting with the compounds of the present invention. In the context of the present invention, a "modulator of function" is an oligomeric compound that causes an alteration in the function of the nucleic acid target or an alteration in the function of any cellular component with which the nucleic acid target has an association.

Modulators that increase or decrease the levels of nucleic acid targets comprise at least an 8-nucleobase portion which is complementary to a target segment of the small untranslated RNA and are from about 8 to 80, 12 to 50 or 15 to 30, or any other range disclosed herein, nucleobases in length. Modulators that alter the function of nucleic acid targets comprise from about 8 to 80, 12 to 50 or 15 to 30, or any other range disclosed herein, nucleobases and act as mimics of endogenous nucleic acid targets or portions thereof.

The screening method comprises contacting a sample, tissue, cell or organism known or suspected to contain a nucleic acid target or a segment of a nucleic acid target with one or more candidate modulators, and selecting for one or more candidate modulators which decrease or increase the expression of a nucleic acid target or the expression of a downstream target regulated by a nucleic acid target. Once it is shown that the candidate modulator or modulators are capable of modulating (e.g. either decreasing or increasing) the expression of a nucleic acid target or its downstream targets, the modulator may then be employed in further investigative studies of the function of the nucleic acid target, or for use as a research, diagnostic, or therapeutic agent in accordance with the present invention.

In such screening and target validation studies, oligomeric compounds of the invention can be used in combination with their respective complementary strand oligomeric compound to form stabilized double-stranded (duplexed) oligonucleotides. Double stranded oligonucleotide moieties have been shown to modulate target expression and regulate translation as well as RNA processing via an antisense mechanism. Moreover, the double-stranded moieties may be subject to chemical modifications (Fire et al., Nature, 1998, 391, 806-811; Timmons et al., Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev., 2001, 15, 188-200; Nishikura et al., Cell, 2001, 107, 415-416; and Bass et al., Cell, 2000, 101, 235-238). For example, such double-stranded moieties have been shown to inhibit expression by the classical hybridization of the antisense strand of the duplex to the target, thereby triggering enzymatic degradation of the target (Tijsterman et al., Science, 2002, 295, 694-697).

For use in drug discovery, oligomeric compounds of the present invention are used to elucidate relationships that exist between nucleic acid targets, genes or proteins and a disease state, phenotype, or condition. These methods include detecting or modulating a target comprising contacting a sample, tissue, cell, or organism with the oligomeric compounds and compositions of the present invention, measuring the levels of the target and/or the levels of downstream gene products including mRNA or proteins encoded thereby, a related phenotypic or chemical endpoint at some time after treatment, and optionally comparing the measured value to an untreated sample, a positive control or a negative control. These methods can also be performed in parallel or in combination with other experiments to determine the function of unknown genes for the process of target validation or to determine the validity of a particular gene product as a target for treatment or prevention of a disease.

The oligomeric compounds and compositions of the present invention can additionally be utilized for diagnostics, therapeutics, prophylaxis and as research reagents and kits. Such uses allows for those of ordinary skill to elucidate the function of particular untranslated or coding nucleic acids or to distinguish between functions of various members of a biological pathway.

For use in kits and diagnostics, the oligomeric compounds and compositions of the present invention, either alone or in combination with other compounds or therapeutics, can be used as, for example, tools in differential and/or combinatorial analyses to elucidate expression patterns of a portion or the entire complement of untranslated or coding nucleic acids expressed within cells and tissues.

As one non-limiting example, expression patterns within cells or tissues treated with one or more compounds or compositions of the invention are compared to control cells or tissues not treated with the compounds or compositions and the patterns produced are analyzed for differential levels of nucleic acid expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma et al., FEBS Lett., 2000, 480, 17-24; Celis et al., FEBS Lett., 2000, 480, 2-16), SAGE (serial analysis of gene expression) (Madden et al., Drug Discov. Today, 2000, 5, 415-425), READS (restriction enzyme amplification of digested cDNAs)

(Prashar et al., Methods Enzymol., 1999, 303, 258-72), TOGA (total gene expression analysis) (Sutcliffe et al., Proc. Natl. Acad. Sci. U.S.A., 2000, 97, 1976-81), protein arrays and proteomics (Celis et al., FEBS Lett., 2000, 480, 2-16; Jungblut et al., Electrophoresis, 1999, 20, 2100-10), expressed sequence tag (EST) sequencing (Celis et al., FEBS Lett., 2000, 480, 2-16; Larsson et al., J. Biotechnol., 2000, 80, 143-57), subtractive RNA fingerprinting (SuRF) (Fuchs et al., Anal. Biochem., 2000, 286, 91-98; Larson et al., Cytometry, 2000, 41, 203-208), subtractive cloning, differential display (DD) (Jurecic et al., Curr. Opin. Microbiol., 2000, 3, 316-21), comparative genomic hybridization (Carulli et al., J. Cell Biochem. Suppl., 1998, 31, 286-96), FISH (fluorescent in situ hybridization) techniques (Going et al., Eur. J. Cancer, 1999, 35, 1895-904) and mass spectrometry methods (To, Comb. Chem. High Throughput Screen, 2000, 3, 235-41).

The compounds and compositions of the invention are useful for, for example, research and diagnostics, because these compounds and compositions hybridize to nucleic acids or interfere with the normal function of these nucleic acids. Hybridization of the compounds and compositions of the invention with a nucleic acid can be detected by means known in the art. Such means may include conjugation of an enzyme to the compound or composition, radiolabelling or any other suitable detection means. Kits using such detection means for detecting the level of selected proteins in a sample may also be prepared.

The specificity and sensitivity of compounds and compositions can also be harnessed by those of skill in the art for therapeutic uses. Antisense oligomeric compounds have been employed as therapeutic moieties in the treatment of disease states in animals, including humans. Antisense oligonucleotide drugs, including ribozymes, have been safely and effectively administered to humans and numerous clinical trials are presently underway. It is thus established that oligomeric compounds can be useful therapeutic modalities that can be configured to be useful in treatment regimes for the treatment of cells, tissues and animals, especially humans.

For therapeutics, an animal, such as a human, suspected of having a disease or disorder presenting conditions that can be treated, ameliorated, or improved by modulating the expression of a selected target nucleic acid is treated by administering the compounds and compositions. For example, in one non-limiting embodiment, the methods comprise administering to or contacting the animal, optionally in need of treatment, with an effective amount of a modulator or mimic to treat, ameliorate or improve the conditions associated with the disease or disorder. The compounds of the present invention effectively modulate the activity or function of the target nucleic acid or inhibit the expression or levels of the target. In some embodiments, the activity or expression of a protein or mRNA is inhibited by about 10% or more, by about 20% or more, by about 30% or more, by about 40% or more, by about 50% or more, by about 60% or more, by about 70% or more, by about 80% or more, by about 90% or more, or by about 95% or more, or by about 99% or more, or by 100%.

As used herein, the term "about" means±2% of the term being modified. Thus, for example, "about" 80% means 78-82%.

The reduction of target levels may be measured in serum, adipose tissue, liver or any other body fluid, tissue or organ of the animal known to contain the target nucleic acid or its precursor. Further, the cells contained within the fluids, tissues or organs being analyzed contain a nucleic acid molecule of a downstream target regulated or modulated by the target nucleic acid itself.

The compounds and compositions of the invention can be utilized in pharmaceutical compositions by adding an effective amount of the compound or composition to a suitable pharmaceutically acceptable diluent or carrier. Use of the oligomeric compounds and methods of the invention may also be useful prophylactically. In some embodiments, a phenotypic change in the disease or consition is observed, measured, or monitored upon treatment.

The compounds and compositions of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. No. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The compounds and compositions of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the oligomeric compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention can be prepared as SATE ((S-acetyl-2-thioethyl) phosphate) derivatives according to the methods disclosed in WO 93/24510, WO 94/26764, and U.S. Pat. No. 5,770,713. Larger oligomeric compounds that are processed to supply, as cleavage products, compounds capable of modulating the function or expression of small untranslated RNAs or their downstream targets are also considered prodrugs.

The term "pharmaceutically acceptable salts" refers to physiologically and pharmaceutically acceptable salts of the compounds and compositions of the invention: i.e., salts that retain the desired biological activity of the parent compound and do not impart undesired toxicological effects thereto. For oligonucleotides, examples of pharmaceutically acceptable salts and their uses are further described in U.S. Pat. No. 6,287,860, and include potassium and sodium salts.

The present invention also includes pharmaceutical compositions and formulations that include the compounds and compositions of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compounds and compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged nucleic acid molecules to form a stable complex. Liposomes that are pH-sensitive or negatively-charged are believed to entrap nucleic acids rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860.

One of skill in the art will recognize that formulations are routinely designed according to their intended use, i.e. route of administration.

Formulations for topical administration include those in which the oligonucleotides of the invention are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, compounds and compositions of the invention may be encapsulated within liposomes or may form complexes thereto, in particular to cationic liposomes. Alternatively, they may be complexed to lipids, in particular to cationic lipids. Fatty acids and esters, pharmaceutically acceptable salts thereof, and their uses are further described in U.S. Pat. No. 6,287,860. Topical formulations are described in detail in U.S. patent application Ser. No. 09/315,298 filed on May 20, 1999.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligonucleotides of the invention are administered in conjunction with one or more penetration enhancers surfactants and chelators. Surfactants include fatty acids and/or esters or salts thereof, bile acids and/or salts thereof. Bile acids/salts and fatty acids and their uses are further described in U.S. Pat. No. 6,287,860. Also suitable are combinations of penetration enhancers, for example, fatty acids/salts in combination with bile acids/salts. A particularly suitable combination is the sodium salt of lauric acid, capric acid and UDCA. Further penetration enhancers include polyoxyethylene-9-lauryl ether, polyoxyethylene-20-cetyl ether. Compounds and compositions of the invention may be delivered orally, in granular form including sprayed dried particles, or complexed to form micro or nanoparticles. Complexing agents and their uses are further described in U.S. Pat. No. 6,287,860. Certain oral formulations for oligonucleotides and their preparation are described in detail in U.S. Pat. No. 6,887,906, U.S. patent application Ser. No. 09/315,298 (filed May 20, 1999), and U.S. Patent Application Publication No. 20030027780.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more of the compounds and compositions of the invention and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethyl-melamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the oligomeric compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of compounds and compositions of the invention and other drugs are also within the scope of this invention. Two or more combined compounds such as two oligomeric compounds or one oligomeric compound combined with further compounds may be used together or sequentially.

In another related embodiment, compositions of the invention may contain one or more of the compounds and compositions of the invention targeted to a first nucleic acid and one or more additional oligomeric compounds targeted to a second nucleic acid target. Alternatively, compositions of the invention may contain two or more oligomeric compounds and compositions targeted to different regions of the same nucleic acid target. Two or more combined compounds may be used together or sequentially.

The formulation of therapeutic compounds and compositions of the invention and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, from 0.1 μg to 10 g per kg of body weight, from 1.0 μg to 1 g per kg of body weight, from 10.0 μg to 100 mg per kg of body weight, from 100 μg to 10 mg per kg of body weight, or from 1 mg to 5 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

As described in detail in examples below, antisense oligonucleotide-mediated inhibition of PPAR-γ expression blocks the process of adipocyte differentiation in vitro. Also as described in examples below, human gene expression microarrays (Affymetrix, Inc., Santa Clara, Calif.), can be used to identify genes that are down-regulated (at statistically significant levels) when expression of PPAR-γ is knocked down with an antisense oligonucleotide. The promoters of most of these down-regulated genes have been analyzed and classified according to one or more motif identification algorithms, for example, the MAST/MEME algorithm (Bailey et al., J. Comput. Biol., 1998, 5, 211-21). These motif data and antisense knock-down adipocyte phenotypic assay data are then used in a data integration process employing further computer algorithms, ultimately generating new classes of information about gene function and gene regulation (including identification of novel promoter motifs), as well as the discovery of genes involved in PPAR-γ gene regulation pathways and adipogenesis. This novel data integration process may also result in the identification of heretofore undiscovered gene regulatory pathways and the assignment of probable functions to an unknown gene or cluster of genes.

While the present invention has been described with specificity in accordance with certain of its embodiments, the following examples serve only to illustrate the invention and are not intended to limit the same.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, (5'-O-(4,4'-Dimethoxytriphenylmethyl)-2'-deoxy-$N^4$-benzoyl-5-methylcytidine-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, (5'-O-(4,4'-Dimethoxytriphenylmethyl)-2'-O-(2-methoxyethyl)-$N^4$-benzoyl-5-methylcytidine-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-$N^6$-benzoyladenosin-3'-O-yl)-2-cyanoethyl-N,N-diisopropylphosphoramidite (MOE A amdite), (5'-O-(4,4'-Dimethoxytriphenylmethyl)-2'-O-(2-methoxyethyl)-$N^4$-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-(2-formadoximinooxy)ethyl)-5-methyluridine, 5'-O-tert-Butyldiphenylsilyl-2'-O-(N,N dimethylaminooxyethyl)-5-methyluridine, (dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-(2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl) phosphoramidite.

Example 2

Oligonucleotide and Oligonucleoside Synthesis

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270.

Alkyl phosphonate oligonucleotides are prepared as described in U.S. Pat. No. 4,469,863.

3'-Deoxy-3'-methylene phosphonate oligonucleotides are prepared as described in U.S. Pat. No. 5,610,289 or 5,625,050.

Phosphoramidite oligonucleotides are prepared as described in U.S. Pat. No. 5,256,775 or U.S. Pat. No. 5,366,878.

Alkylphosphonothioate oligonucleotides are prepared as described in published PCT applications PCT/US94/00902 and PCT/US93/06976 (published as WO 94/17093 and WO 94/02499, respectively).

3'-Deoxy-3'-amino phosphoramidate oligonucleotides are prepared as described in U.S. Pat. No. 5,476,925.

Phosphotriester oligonucleotides are prepared as described in U.S. Pat. No. 5,023,243.

Borano phosphate oligonucleotides are prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages are prepared as described in U.S. Pat. Nos. 5,378,825, 5,386,023, 5,489,677, 5,602,240 and 5,610,289.

Formacetal and thioformacetal linked oligonucleosides are prepared as described in U.S. Pat. Nos. 5,264,562 and 5,264,564.

Ethylene oxide linked oligonucleosides are prepared as described in U.S. Pat. No. 5,223,618.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, Ph.D. Thesis, University of Colorado, 1996; Scaringe et al., J. Am. Chem. Soc., 1998, 120, 11820-11821; Matteucci et al., J. Am. Chem. Soc., 1981, 103, 3185-3191; Beaucage et al., Tetrahedron Lett., 1981, 22, 1859-1862; Dahl et al., Acta Chem. Scand., 1990, 44, 639-641; Reddy et al., Tetrahedrom Lett., 1994, 25, 4311-4314; Wincott et al., Nucleic Acids Res., 1995, 23, 2677-2684; Griffin et al., Tetrahedron, 1967, 23, 2301-2313; Griffin et al., Tetrahedron, 1967, 23, 2315-2331).

The present invention is also useful for the preparation of oligomeric compounds incorporating at least one 2'-O-protected nucleoside. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound. All 2'-O-protecting groups amenable to the synthesis of oligomeric compounds are included in the present invention.

In general a protected nucleoside is attached to a solid support by for example a succinate linker. Then the oligonucleotide is elongated by repeated cycles of deprotecting the 5'-terminal hydroxyl group, coupling of a further nucleoside unit, capping and oxidation (alternatively sulfurization). In a more frequently used method of synthesis the completed oligonucleotide is cleaved from the solid support with the removal of phosphate protecting groups and exocyclic amino protecting groups by treatment with an ammonia solution. Then a further deprotection step is normally required for the more specialized protecting groups used for the protection of 2'-hydroxyl groups which will give the fully deprotected oligonucleotide.

A large number of 2'-O-protecting groups have been used for the synthesis of oligoribonucleotides but over the years more effective groups have been discovered. One key to an effective 2'-O-protecting group is that it is capable of selectively being introduced at the 2'-O-position and that it can be removed easily after synthesis without the formation of unwanted side products. The protecting group also needs to be inert to the normal deprotecting, coupling, and capping steps required for oligoribonucleotide synthesis. Some of the protecting groups used initially for oligoribonucleotide synthesis included tetrahydropyran-1-yl and 4-methoxytetrahydropyran-4-yl. These two groups are not compatible with all 5'-O-protecting groups so modified versions were used with 5'-DMT groups such as 1-(2-fluorophenyl)-4-methoxypiperidin-4-yl (Fpmp). Reese has identified a number of piperidine derivatives (like Fpmp) that are useful in the synthesis of oligoribonucleotides including 1-((chloro-4-methyl)phenyl)-4'-methoxypiperidin-4-yl (Reese et al., Tetrahedron Lett., 1986, 27, 2291). Another approach was to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group initially used for the synthesis of oligoribonucleotides was the t-butyldimethylsilyl group (Ogilvie et al., Tetrahedron Lett., 1974, 2861; Hakimelahi et al., Tetrahedron Lett., 1981, 22, 2543; and Jones et al., J. Chem. Soc. Perkin I., 2762). The 2'-O-protecting groups can require special reagents for their removal such as for example the t-butyldimethylsilyl group is normally removed after all other cleaving/deprotecting steps by treatment of the oligomeric compound with tetrabutylammonium fluoride (TBAF).

One group of researchers examined a number of 2'-O-protecting groups (Pitsch, Chimia, 2001, 55, 320-324). The group examined fluoride labile and photolabile protecting groups that are removed using moderate conditions. One photolabile group that was examined was the (2-(nitrobenzyl)oxy)methyl (nbm) protecting group (Schwartz et al., Bioorg. Med. Chem. Lett., 1992, 2, 1019). Other groups examined included a number structurally related formaldehyde acetal-derived, 2'-O-protecting groups. Also prepared were a number of related protecting groups for preparing 2'-O-alkylated nucleoside phosphoramidites including 2'-O-((triisopropylsilyl)oxy)methyl (2'-O—$CH_2$—O—$Si(iPr)_3$, TOM). One 2'-O-protecting group that was prepared to be used orthogonally to the TOM group was 2'-O-(R)-1-(2-nitrophenyl)ethyloxy)methyl) ((R)-mnbm).

Another strategy using a fluoride labile 5'-O-protecting group (non-acid labile) and an acid labile 2'-O-protecting group has been reported (Scaringe, Methods, 2001, 23, 06-217). A number of possible silyl ethers were examined for 5'-O-protection and a number of acetals and orthoesters were examined for 2'-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

Although a lot of research has focused on the synthesis of oligoribonucleotides the main RNA synthesis strategies that are presently being used commercially include 5'-O-DMT-2'-O-t-butyldimethylsilyl (TBDMS), 5'-O-DMT-2'-O-(1(2- fluorophenyl)-4-methoxypiperidin-4-yl) (FPMP), 2'-O-((triisopropylsilyl)oxy)methyl (2'-O—CH$_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable to the present invention.

The structures corresponding to these protecting groups are shown below.

TBDMS=5'-O-DMT-2'-O-t-butyldimethylsilyl;

TOM=2'-O-((triisopropylsilyl)oxy)methyl;

DOD/ACE=(5'-O-bis(trimethylsiloxy)cyclododecyloxysilyl ether-2'-O-bis(2-acetoxyethoxy)methyl FPMP=5'-O-DMT-2'-O-(1(2-fluorophenyl)-4-methoxypiperidin-4-yl)

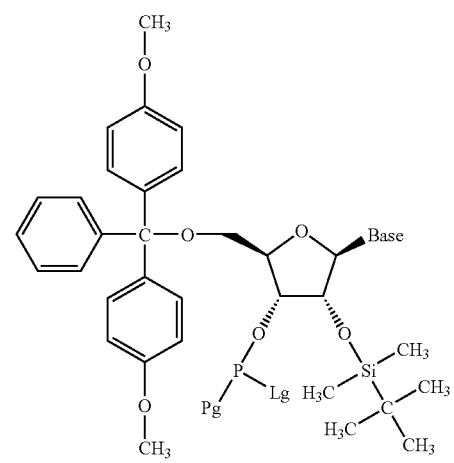

DMT/TBDMS

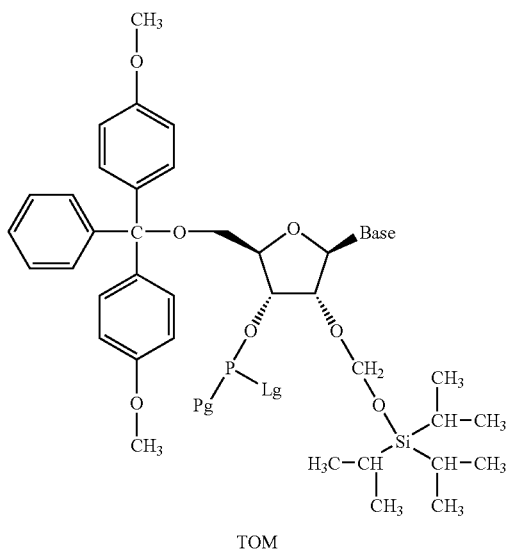

TOM

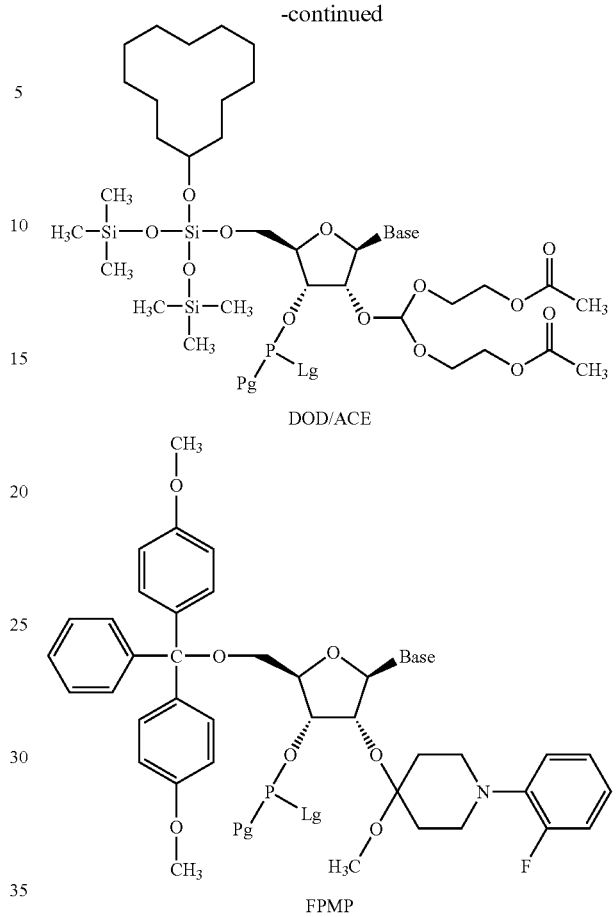

DOD/ACE

FPMP

All of the aforementioned RNA synthesis strategies are amenable to the present invention. Strategies that would be a hybrid of the above e.g. using a 5'-protecting group from one strategy with a 2'-O-protecting from another strategy is also amenable to the present invention.

The preparation of ribonucleotides and oligomeric compounds having at least one ribonucleoside incorporated and all the possible configurations falling in between these two extremes are encompassed by the present invention. The corresponding oligomeric compounds can be hybridized to further oligomeric compounds including oligoribonucleotides having regions of complementarity to form double-stranded (duplexed) oligomeric compounds.

The methods of preparing oligomeric compounds of the present invention can also be applied in the areas of drug discovery and target validation.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers."

(2'-O-Me)-(2'-deoxy)-(2'-O-Me) Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

(2'-O-(2-Methoxyethyl))-(2'-deoxy)-(2'-O-(Methoxyethyl)) Chimeric Phosphorothioate Oligonucleotides (2'-O-(2-methoxyethyl))-(2'-deoxy)-(−2'-O-(methoxyethyl)) chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

(2'-O-(2-Methoxyethyl)Phosphodiester)-(2'-deoxy Phosphorothioate)-(2'-O-(2-Methoxyethyl)Phosphodiester) Chimeric Oligonucleotides (2'-O-(2-methoxyethyl phosphodiester)-(2'-deoxy phosphorothioate)-(2'-O-(methoxyethyl)phosphodiester) chimeric oligonucleotides are prepared as per the above procedure for the 2'-O-methyl chimeric oligonucleotide with the substitution of 2'-O (methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap. Other chimeric oligonucleotides, chimeric oligonucleosides and mixed chimeric oligonucleotides/oligonucleosides are synthesized according to U.S. Pat. No. 5,623,065.

Example 5

Design and Screening of Duplexed Oligomeric Compounds Targeting a Target

In accordance with the present invention, a series of nucleic acid duplexes comprising the oligomeric compounds of the present invention and their complements can be designed to target a nucleic acid target. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO:6) and having a two-nucleobase overhang of deoxythymidine(dT) would have the following structure:

```
cgagaggcggacgggaccgTT   (SEQ ID NO:7)
|||||||||||||||||||     Antisense Strand
TTgctctccgcctgccctggc   (SEQ ID NO:8) Complement
```

In another embodiment, a duplex comprising an antisense strand having the same sequence CGAGAGGCGGACGG-GACCG (SEQ ID NO:6) may be prepared with blunt ends (no single stranded overhang) as shown:

```
cgagaggcggacgggaccg   (SEQ ID NO:6)
|||||||||||||||||||   Antisense Strand
gctctccgcctgccctggc   (SEQ ID NO:9) Complement
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 µM. Once diluted, 30 µL of each strand is combined with 15 µL of a 5× solution of annealing buffer. The final concentration of said buffer is 100 mM potassium acetate, 30 mM HEPES-KOH pH 7.4, and 2 mM magnesium acetate. The final volume is 75 µL This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM. This solution can be stored frozen (−20° C.) and freeze-thawed up to 5 times.

Once prepared, the duplexed oligomeric compounds are evaluated for their ability to modulate a target expression or function.

When cells reached 80% confluency, they are treated with duplexed antisense oligomeric compounds of the invention. For cells grown in 96-well plates, wells are washed once with 200 µL OPTI-MEM-1 reduced-serum medium (Gibco BRL) and then treated with 130 µL of OPTI-MEM-1 containing 12 µg/mL LIPOFECTIN™ (Invitrogen Corporation, Carlsbad, Calif.) and the desired duplex antisense oligomeric compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., J. Biol. Chem. 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the oligomeric compounds utilizing electrospray-mass spectroscopy. All assay test plates were diluted from the master plate using single and multi-channel robotic pipettors. Plates were judged to be acceptable if at least 85% of the oligomeric compounds on the plate were at least 85% full length.

Example 9

Cell Culture and Oligonucleotide Treatment

The effect of oligomeric compounds on target nucleic acid expression or function can be tested in any of a variety of cell types provided that the target nucleic acid is present at measurable levels. This can be readily determined by methods routine in the art, for example Northern blot analysis, ribonuclease protection assays, or RT-PCR. The following cell types are provided for illustrative purposes, but other cell types can be routinely used, provided that the target is present in the cell type chosen.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 μg/mL (Invitrogen Corporation, Carlsbad, Calif.). Cells were routinely passaged by trypsinization and dilution when they reached 90% confluence. For Northern blotting or other analyses, cells harvested when they reached 90% confluence. Cells were seeded into 96-well plates (Falcon-Primaria #353872) at a density of 7000 cells/well for use in RT-PCR analysis.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 μg/mL (Invitrogen Corporation, Carlsbad, Calif.). Cells were routinely passaged by trypsinization and dilution when they reached 90% confluence.

HepG2 Cells:

The human hepatoblastoma cell line HepG2 was obtained from the American Type Culture Collection (ATCC) (Manassas, Va.). HepG2 cells are routinely cultured in Eagle's Minimum Essential Medium (MEM) supplemented with 10% fetal bovine serum, 0.1 mM non-essential amino acids, 1 mM sodium pyruvate, 100 Units/ml Penicillin and 100 μg/ml Streptomycin (Invitrogen Corporation, Carlsbad, Calif.). Cells were routinely passaged by trypsinization and dilution when they reached 90% confluence. Cells were seeded into collagen coated 96-well plates (BIOCOAT cellware, Collagen type I, B-D #354407/356407, Becton Dickinson, Bedford, Mass.) at a density of 7500 cells/well for oligonucleotide transfection and subsequent real-time PCR analysis or for caspase activity assay.

Preadipocytes:

Human preadipocytes were obtained from Zen-Bio, Inc. (Research Triangle Park, N.C.). Preadipocytes were routinely maintained in Preadipocyte Medium (ZenBio, Inc., Research Triangle Park, N.C.) supplemented with antibiotics as recommended by the supplier. Cells were routinely passaged by trypsinization and dilution when they reached 90% confluence. Cells were routinely maintained for up to 5 passages as recommended by the supplier. To induce differentiation of preadipocytes, cells are then incubated with differentiation media consisting of Preadipocyte Medium further supplemented with 2% more fetal bovine serum (final total of 12%), amino acids, 100 nM insulin, 0.5 mM IBMX, 1 μM dexamethasone and 1 μM BRL49653. Cells are left in differentiation media for 3-5 days and then re-fed with adipocyte media consisting of Preadipocyte Medium supplemented with 33 μM biotin, 17 μM pantothenate, 100 nM insulin and 1 μM dexamethasone. Cells differentiate within one week. At this point cells are ready for treatment with the oligomeric compounds of the invention.

Differentiated Adipocytes:

Human adipocytes were obtained from Zen-Bio, Inc. (Research Triangle Park, N.C.). Adipocytes were routinely maintained in Adipocyte Medium (ZenBio, Inc., Research Triangle Park, N.C.) supplemented with antibiotics as recommended by the supplier. Cells were routinely passaged by trypsinization and dilution when they reached 90% confluence. Cells were routinely maintained for up to 5 passages as recommended by the supplier.

For Northern blotting or other analysis, cells may be seeded onto 100 mm or other standard tissue culture plates and treated similarly, using appropriate volumes of medium and oligonucleotide.

Treatment with Antisense Oligomeric Compounds:

When cells reached 65-75% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™ containing 3.75 μg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from ISIS 13920 (TCCGTCATCGCTCCT-CAGGG, SEQ ID NO:1) which is targeted to human H-ras, or ISIS 18078, (GTGCGCGCGAGCCCGAAATC, SEQ ID NO:2) which is targeted to human Jun-N-terminal kinase-2 (JNK2) or another suitable positive control. Controls are 2'-O-methoxyethyl gapmers (2'-O-methoxyethyls shown in bold) with a phosphorothioate backbone or having chemical modifications similar to the oligonucleotides being tested. For mouse or rat cells the positive control oligonucleotide is ISIS 15770 (ATGCATTCTGCCCCCAAGGA, SEQ ID NO:3), a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) or other suitable control target mRNA is then utilized as the screening concentration for new oligonucleotides in subsequent experiments for that cell line. If 80% inhibition is not achieved, the lowest concentration of positive control oligonucleotide that results in 60% inhibition of target expression or function is then utilized as the oligonucleotide screening concentration in subsequent experiments for that cell line. The concentrations of oligonucleotides used herein are from 10 nM to 300 nM.

Example 10

Analysis of Oligonucleotide Inhibition of a Target Expression

Modulation of a target expression can be assayed in a variety of ways known in the art. For example, target nucleic acid levels can be quantitated by, e.g., Northern blot analysis, competitive polymerase chain reaction (PCR), or real-time PCR(RT-PCR). Real-time quantitative PCR is presently suitable. RNA analysis can be performed on total cellular RNA or poly(A)+ mRNA. Methods of RNA isolation are well known in the art. Northern blot analysis is also routine in the art. Real-time quantitative (PCR) can be conveniently accomplished using the commercially available ABI PRISMT™ 7600, 7700, or 7900 Sequence Detection System, available from PE-Applied Biosystems, Foster City, Calif. and used according to manufacturer's instructions.

Protein levels of a downstream target modulated or regulated by a target nucleic acid can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

In Vitro and In Vivo Assays

Phenotypic Assays

Once target inhibitors have been identified by the methods disclosed herein, the oligomeric compounds are further investigated in one or more phenotypic assays, each having measurable endpoints predictive or suggestive of efficacy in the treatment, amelioration or improvement of physiologic conditions associated with a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints. Phenotypic endpoints include changes in cell morphology over time or treatment dose as well as changes in levels of cellular components such as mRNAs, proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the presence or expression of one or more of the genes of the cell) after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Mouse Model of Tumorigenesis:

Animal models of tumorigenesis are used in some embodiments of the present invention. In this model, tumorigenic cells are injected into immunocompromised mice (i.e. nude mice), and subsequent growth of a tumor is measured.

Serially transplanted MDA-MB-231 (a human breast carcinoma cell line, American Type Culture Collection, Manassus, Va.) tumors are established subcutaneously in nude mice. Beginning two weeks later, one or more of the oligomeric compounds of the invention are administered intravenously daily for 14 days at dosages of 15 mg/kg or 30 mg/kg. Control compounds are also administered at these doses, and a saline control is also given. Tumor growth rates are monitored for the two-week period of oligonucleotide administration. Activity of the oligomeric compounds of the invention is measured by a reduction in tumor growth. Activity is measured by reduced tumor volume compared to saline or control compound. Following death or sacrifice of mice, tumor tissue is fixed in 4% formalin, embedded in paraffin, sectioned and stained with hematoxylin and eosin. Tumor tissue sections are evaluated for tumor morphology and size.

Human A549 lung tumor cells are also injected into nude mouse to produce tumors. 200 μl of A549 cells ($5 \times 10^6$ cells) are implanted subcutaneously in the inner thigh of nude mice. Oligomeric compounds of the invention are administered twice weekly for four weeks, beginning one week following tumor cell inoculation. Oligonucleotides are formulated with cationic lipids (LIPOFECTIN™, Invitrogen Corporation, Carlsbad, Calif.) and given subcutaneously in the vicinity of the tumor. Oligonucleotide dosage is 5 mg/kg with 60 mg/kg cationic lipid. Tumor size is recorded weekly. Activity of the oligomeric compounds of the invention is measured by reduction in tumor size compared to controls.

Xenograft studies are also performed using the U-87 human glioblastoma cell line (American Type Culture Collection, Manassus, Va.). Nude mice are injected subcutaneously with $2 \times 10^7$ U-87 cells. Mice are injected intraperitoneally with one or more of the oligomeric compounds of the invention or a control compound at dosages of either 15 mg/kg or 30 mg/kg for 21 consecutive days beginning 7 days after xenografts are implanted. Saline-injected animals serve as a control. Tumor volumes are measured on days 14, 21, 24, 31 and 35. Activity is measured by reduced tumor volume compared to saline or control compound. Following death or sacrifice of mice, tumor tissue is fixed in 4% formalin, embedded in paraffin, sectioned and stained with hematoxylin and eosin. Tumor tissue sections are evaluated for tumor morphology and size.

Alternatively, intracerebral U-87 xenografts are generated by implanting U-87 glioblastoma cells into the brains of nude mice. Mice are treated via continuous intraperitoneal administration with one or more of the oligomeric compounds of the invention at 20 mg/kg, control compound at 20 mg/kg or saline beginning on day 7 after xenograft implantation. Activity of the oligomeric compounds of the invention is measured by an increase in survival time compared to controls. Following death or sacrifice, brain tissue is fixed in 4% formalin, embedded in paraffin, sectioned and stained with hematoxylin and eosin. Brain tissue sections are evaluated for tumor growth.

Leptin-Deficient Mice (a Model of Obesity and Diabetes (ob/ob Mice)):

Leptin is a hormone produced by fat cells that regulates appetite. Deficiencies in this hormone in both humans and non-human animals leads to obesity. ob/ob mice have a mutation in the leptin gene which results in obesity and hyperglycemia. As such, these mice are a useful model for the investigation of obesity and diabetes and treatments designed to treat these conditions. ob/ob mice have higher circulating levels of insulin and are less hyperglycemic than db/db mice, which harbor a mutation in the leptin receptor. In accordance with the present invention, the oligomeric compounds of the invention are tested in the ob/ob model of obesity and diabetes.

Seven-week old male C57B1/6J-Lep ob/ob mice (Jackson Laboratory, Bar Harbor, Me.) are fed a diet with a fat content of 10-15% and are subcutaneously injected with the oligomeric compounds of the invention or a control compound at a dose of 25 mg/kg two times per week for 4 weeks. Saline-injected animals, leptin wildtype littermates (i.e. lean littermates) and ob/ob mice fed a standard rodent diet serve as controls. After the treatment period, mice are sacrificed and target levels are evaluated in liver, brown adipose tissue (BAT) and white adipose tissue (WAT). RNA isolation and target RNA expression level quantitation are performed as described by other examples herein.

To assess the physiological effects resulting from inhibition of target, the ob/ob mice are evaluated at the end of the treatment period for serum lipids, serum free fatty acids, serum cholesterol (CHOL), liver triglycerides, fat tissue triglycerides and liver enzyme levels. Hepatic steatosis, or clearing of lipids from the liver, is assessed by measuring the liver triglyceride content. Hepatic steatosis is assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of target inhibition on glucose and insulin metabolism are evaluated in the ob/ob mice treated with the oligomeric compounds of the invention. Plasma glucose is measured at the start of the treatment and after 2 weeks and 4 weeks of treatment. Plasma insulin is similarly measured at the beginning of the treatment, and following at 2 weeks and at 4 weeks of treatment. Glucose and insulin tolerance tests are also administered in fed and fasted mice. Mice receive intraperitoneal injections of either glucose or insulin, and the blood glucose and insulin levels are measured before the insulin or glucose challenge and at 15, 20 or 30 minute intervals for up to 3 hours.

To assess the metabolic rate of ob/ob mice treated with the oligomeric compounds of the invention, the respiratory quotient and oxygen consumption of the mice are also measured.

The ob/ob mice that received treatment are evaluated at the end of the treatment period for the effects of target inhibition on the expression of genes that participate in lipid metabolism, cholesterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-6-phosphatase and phosphoenolpyruvate carboxykinase 1, lipoprotein lipase and hormone sensitive lipase. mRNA levels in liver and white and brown adipose tissue are quantitated by real-time PCR as described in other examples herein, employing primer/probe sets that are generated using published sequences of each gene of interest.

Leptin Receptor-Deficient Mice (a Model of Obesity and Diabetes (db/db Mice)):

db/db mice have a mutation in the leptin receptor gene which results in obesity and hyperglycemia. As such, these mice are a useful model for the investigation of obesity and diabetes and treatments designed to treat these conditions.

db/db mice, which have lower circulating levels of insulin and are more hyperglycemic than ob/ob mice which harbor a mutation in the leptin gene, are often used as a rodent model of type 2 diabetes. In accordance with the present invention, oligomeric compounds of the present invention are tested in the db/db model of obesity and diabetes.

Seven-week old male C57B1/6J-Lepr db/db mice (Jackson Laboratory, Bar Harbor, Me.) are fed a diet with a fat content of 15-20% and are subcutaneously injected with one or more of the oligomeric compounds of the invention or a control compound at a dose of 25 mg/kg two times per week for 4 weeks. Saline-injected animals, leptin receptor wildtype littermates (i.e. lean littermates) and db/db mice fed a standard rodent diet serve as controls. After the treatment period, mice are sacrificed and target levels are evaluated in liver, BAT and WAT as described supra.

To assess the physiological effects resulting from inhibition of target, the db/db mice that receive treatment are evaluated at the end of the treatment period for serum lipids, serum free fatty acids, serum cholesterol (CHOL), liver triglycerides, fat tissue triglycerides and liver enzyme levels. Hepatic steatosis is assessed by measuring the liver triglyceride content and oil red O staining, as described supra.

The effects of target inhibition on glucose and insulin metabolism are also evaluated in the db/db mice treated with the oligomeric compounds of the invention. Plasma glucose is measured at the start of the treatment and after 2 weeks and 4 weeks of treatment. Plasma insulin is similarly measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose levels are measured before the insulin or glucose challenge and 15, 30, 60, 90 and 120 minutes following the injection.

To assess the metabolic rate of db/db mice treated with the oligomeric compounds of the invention, the respiratory quotient and oxygen consumption of the mice is also measured.

The db/db mice that receive treatment are evaluated at the end of the treatment period for the effects of target inhibition on the expression of genes that participate in lipid metabolism, cholesterol biosynthesis, fatty acid oxidation, fatty acid storage, gluconeogenesis and glucose metabolism, as described supra.

Lean Mice on a Standard Rodent Diet:

C57B1/6 mice are maintained on a standard rodent diet and are used as control (lean) animals. In one embodiment of the present invention, the oligomeric compounds of the invention are tested in normal, lean animals.

Seven-week old male C57B1/6 mice are fed a diet with a fat content of 4% and are subcutaneously injected with one or more of the oligomeric compounds of the invention or control compounds at a dose of 25 mg/kg two times per week for 4 weeks. Saline-injected animals serve as a control. After the treatment period, mice are sacrificed and target levels are evaluated in liver, BAT and WAT as described supra.

To assess the physiological effects resulting from inhibition of target, the lean mice that receive treatment are evaluated at the end of the treatment period for serum lipids, serum free fatty acids, serum cholesterol (CHOL), liver triglycerides, fat tissue triglycerides and liver enzyme levels. Hepatic steatosis is assessed by measuring the liver triglyceride content and oil red O staining, as described supra.

The effects of target inhibition on glucose and insulin metabolism are also evaluated in the lean mice treated with the oligomeric compounds of the invention. Plasma glucose is measured at the start of the treatment and after 2 weeks and 4 weeks of treatment. Plasma insulin is similarly measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose levels are measured before the insulin or glucose challenge and 15, 30, 60, 90 and 120 minutes following the injection.

To assess the metabolic rate of lean mice treated with the oligomeric compounds of the invention, the respiratory quotient and oxygen consumption of the mice is also measured.

The lean mice that received treatment are evaluated at the end of the treatment period for the effects of target inhibition on the expression of genes that participate in lipid metabolism, cholesterol biosynthesis, fatty acid oxidation, fatty acid storage, gluconeogenesis and glucose metabolism, as described supra.

Levin Model of Diet-Induced Obesity in Rats:

The Levin Model is a polygenic model of rats selectively bred to develop diet-induced obesity (DIO) associated with impaired glucose tolerance, dyslipidemia and insulin resistance when fed a high-fat diet (Levin et al., Am. J. Physiol, 1997, 273, R725-30). The advantage of this model is that it displays traits more similar to human obesity and glucose intolerance than in animals that are obese/hyperinsulinemic due to genetic defects e.g. defects in leptin signaling. This model is useful in investigating the oligomeric compounds of the present invention for their ability to affect obesity and related complications, such as impaired glucose tolerance, dyslipidemia and insulin resistance. In accordance with the present invention, the oligomeric compounds of the invention are tested in the Levin model of diet-induced obesity.

Eight-week old male Levin rats (Charles River Laboratories, Wilmington, Mass.), weighing ~500 g, are fed a diet with a fat content of 60% for eight weeks, after which they are subcutaneously injected with one or more of the oligomeric compounds of the invention at a dose of 25 mg/kg X 2 per week for 8 weeks. Control groups consist of animals injected with saline or a control compound and lean littermates fed a standard rodent diet. The control compound is injected at the same dose as the target-specific compound.

Throughout the treatment period, the rats are evaluated for food consumption, weight gain, as well as serum levels of glucose, insulin, cholesterol, free fatty acids, triglycerides and liver enzymes.

The effects of target inhibition on glucose and insulin metabolism are also evaluated in the Levin rats treated with the oligomeric compounds of the invention. Plasma glucose and insulin are monitored throughout the treatment by analyzing blood samples. Glucose and tolerance are assessed in fed or fasted rats. After blood is collected for baseline glucose and insulin levels, a glucose challenge is administered, after which blood glucose and insulin levels are measured at 15, 20 or 30 minute intervals for up to 3 hours. Insulin tolerance is similarly analyzed, beginning with blood collection for baseline glucose and insulin levels, followed by an insulin challenge, after which blood glucose levels are measured at 15, 20 or 30 minute intervals for up to 3 hours. Plasma insulin and glucose are also measured at study termination.

At the end of the treatment period, the rats are sacrificed. Organs are removed and weighed, including liver, white adipose tissue, brown adipose tissue and spleen. Target RNA expression levels are measured in all tissues that are isolated, using quantitative real-time PCR. Target protein levels are also evaluated by immunoblot analysis using antibodies that specifically recognize the target protein.

Also evaluated at the end of the treatment period are serum lipids, serum free fatty acids, serum cholesterol (CHOL), liver triglycerides, fat tissue triglycerides and liver enzyme levels. Hepatic steatosis is assessed by measuring the liver triglyceride content and oil red 0 staining, as described supra.

The Levin rats that receive treatment are evaluated at the end of the treatment period for the effects of target inhibition on the expression of genes that participate in lipid metabolism, cholesterol biosynthesis, fatty acid oxidation, fatty acid storage, gluconeogenesis and glucose metabolism, as described supra.

C57BL/6 on a High-Fat Diet (a Model of Diet-Induced Obesity (DIO)):

The C57BL/6 mouse strain is reported to be susceptible to hyperlipidemia-induced atherosclerotic plaque formation. Consequently, when these mice are fed a high-fat diet, they develop diet-induced obesity. Accordingly these mice are a useful model for the investigation of obesity and treatments designed to treat these conditions. In one embodiment of the present invention, the oligomeric compounds of the invention are tested in a model of diet-induced obesity.

Male C57BL/6 mice (7-weeks old) receive a 60% fat diet for 8 weeks, after which mice are subcutaneously injected with one or more of the oligomeric compounds of the invention at a dose of 25 mg/kg two times per week for 4 weeks. Saline-injected or control compound-injected animals serve as a control. After the treatment period, mice are sacrificed and target levels are evaluated in liver, BAT and WAT as described supra.

To assess the physiological effects resulting from inhibition of target, the diet-induced obese mice that receive treatment are evaluated at the end of the treatment period for serum lipids, serum free fatty acids, serum cholesterol (CHOL), liver triglycerides, fat tissue triglycerides and liver enzyme levels. Hepatic steatosis is assessed by measuring the liver triglyceride content and oil red O staining, as described supra.

The effects of target inhibition on glucose and insulin metabolism are also evaluated in the diet-induced obese mice treated with the oligomeric compounds of the invention. Plasma glucose is measured at the start of treatment and after 2 weeks and 4 weeks of treatment. Plasma insulin is similarly measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose and insulin levels are measured before the insulin or glucose challenge and at 15, 20 or 30 minute intervals for up to 3 hours.

To assess the metabolic rate of diet-induced obese mice treated with the oligomeric compounds of the invention, the respiratory quotient and oxygen consumption of the mice is also measured.

The diet-induced obese mice that receive treatment are evaluated at the end of the treatment period for the effects of target inhibition on the expression of genes that participate in lipid metabolism, cholesterol biosynthesis, fatty acid oxidation, fatty acid storage, gluconeogenesis and glucose metabolism, as described supra.

P-407 Mouse Model of Hyperlipidemia:

Poloxamer 407 (P-407), an inert block copolymer comprising a hydrophobic core flanked by hydrophilic polyoxyethylene units has been shown to induce hyperlipidemia in rodents. In the mouse, one injection, intraperitoneally, of P-407 (0.5 g/kg) produced hypercholesterolemia that peaked at 24 hours and returned to control levels by 96 hours following treatment (Palmer et al., Atherosclerosis, 1998, 136, 115-123). Consequently, these mice are a useful model for the investigation of compounds that modulate hyperlipidemia. In accordance with the present invention, the oligomeric compounds of the invention are tested in the P-407 model of hyperlipidemia.

Seven-week old male C57B1/6 mice are divided into two groups; (1) control and (2) P-407 injected animals (0.5 g/kg every 3 days, following an overnight fast). Animals in each group receive either a saline injection or injection with one or more of the oligomeric compounds of the invention or control compounds at 25 mg/kg three times per week or 50 mg/kg two times per week. All injections are administered intraperitoneally.

After the treatment period, mice are sacrificed and target levels are evaluated in liver, BAT and WAT as described supra.

To assess the physiological effects resulting from inhibition of target, the P-407 injected animals that receive treatment are evaluated at the end of the treatment period for serum lipids, serum free fatty acids, serum cholesterol (CHOL), liver triglycerides, fat tissue triglycerides and liver enzyme levels. Hepatic steatosis is assessed by measuring the liver triglyceride content and oil red O staining, as described supra.

The effects of target inhibition on glucose and insulin metabolism are evaluated in the P-407 injected animals treated with the oligomeric compounds of the invention. Plasma glucose is measured at the start of the treatment and after 2 weeks and 4 weeks of treatment. Plasma insulin is similarly measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose and insulin levels are measured before the insulin or glucose challenge and at 15, 20 or 30 minute intervals for up to 3 hours.

To assess the metabolic rate of P-407 injected animals treated with the oligomeric compounds of the invention, the respiratory quotient and oxygen consumption of the mice is measured.

The P-407 injected animals that receive treatment are evaluated at the end of the treatment period for the effects of target inhibition on the expression of genes that participate in lipid metabolism, cholesterol biosynthesis, fatty acid oxidation, fatty acid storage, gluconeogenesis and glucose metabolism, as described supra.

ApoE Knockout Mice (a Model of Dyslipidemia and Obesity):

B6.129P-ApoE$^{tm1Unc}$ knockout mice (herein referred to as ApoE knockout mice) obtained from The Jackson Laboratory (Bar Harbor, Me.), are homozygous for the Apoe$^{tm1Unc}$ mutation and show a marked increase in total plasma cholesterol levels that are unaffected by age or sex. These animals present with fatty streaks in the proximal aorta at 3 months of age. These lesions increase with age and progress to lesions with less lipid but more elongated cells, typical of a more advanced stage of pre-atherosclerotic lesion.

The mutation in these mice resides in the apolipoprotein E (ApoE) gene. The primary role of the ApoE protein is to transport cholesterol and triglycerides throughout the body. It stabilizes lipoprotein structure, binds to the low density lipoprotein receptor (LDLR) and related proteins, and is present in a subclass of HDLs, providing them the ability to bind to LDLR. ApoE is expressed most abundantly in the liver and brain. In one embodiment of the present invention, female B6.129P-Apoetm1Unc knockout mice (ApoE knockout mice) are used in the following studies to evaluate the oligomeric compounds of the invention as potential lipid lowering compounds.

Female ApoE knockout mice range in age from 5 to 7 weeks and are placed on a normal diet for 2 weeks before study initiation. ApoE knockout mice are then fed ad libitum a 60% fat diet, with 0.15% added cholesterol to induce dyslipidemia and obesity. Control animals include ApoE knockout mice and ApoE wildtype mice (i.e. lean littermates) maintained on a high-fat diet with no added cholesterol. After overnight fasting, mice from each group are dosed intraperitoneally every three days with saline, 50 mg/kg of a control compound or 5, 25 or 50 mg/kg of one or more of the oligomeric compounds of the invention.

After the treatment period, mice are sacrificed and target levels are evaluated in liver, BAT and WAT as described supra.

To assess the physiological effects resulting from inhibition of target, the ApoE knockout mice that receive treatment are evaluated at the end of the treatment period for serum lipids, serum free fatty acids, serum cholesterol (CHOL), liver triglycerides, fat tissue triglycerides and liver enzyme levels. Hepatic steatosis is assessed by measuring the liver triglyceride content and oil red O staining, as described supra.

The effects of target inhibition on glucose and insulin metabolism are also evaluated in the ApoE knockout mice treated with the oligomeric compounds of the invention. Plasma glucose is measured at the start of the treatment and after 2 weeks and 4 weeks of treatment. Plasma insulin is similarly measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose and insulin levels are measured before the insulin or glucose challenge and at 15, 20 or 30 minute intervals for up to 3 hours.

To assess the metabolic rate of ApoE knockout mice treated with the oligomeric compounds of the invention, the respiratory quotient and oxygen consumption of the mice are measured.

The ApoE knockout mice that receive treatment are evaluated at the end of the treatment period for the effects of target inhibition on the expression of genes that participate in lipid metabolism, cholesterol biosynthesis, fatty acid oxidation, fatty acid storage, gluconeogenesis and glucose metabolism, as described supra.

Example 12

RNA Isolation

Poly(A)+ mRNA Isolation

Poly(A)+ mRNA was isolated according to Miura et al., (Clin. Chem., 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Target RNA Levels

Quantitation of a target RNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of RNA from untreated control samples generates a standard curve that is used to quantitate the percent inhibition after oligonucleotide treatment of test samples.

Prior to quantitative PCR analysis, primer/probe sets specific to the target gene (or RNA) being measured are evaluated for their ability to be "multiplexed" with a GAPDH amplification reaction. In multiplexing, both the target gene (or RNA) and the internal standard gene GAPDH are amplified concurrently in a single sample. In this analysis, RNA isolated from untreated cells is serially diluted. Each dilution is amplified in the presence of primer/probe sets specific for GAPDH only, target gene (or RNA) only ("single-plexing"), or both (multiplexing). Following PCR amplification, standard curves of GAPDH and target RNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer/probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene (or RNA) target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers are designed to hybridize to the target sequence.

In other embodiments, once prepared as described in previous examples, duplexed oligomeric compounds were evaluated in HeLa cells (American Type Culture Collection, Manassas Va.). Culture methods used for HeLa cells are available from the ATCC and may be found, for example, at www(dot)atcc(dot)org. For cells grown in 96-well plates, wells were washed once with 200 µL OPTI-MEM-1 reduced-serum medium (Gibco BRL) and then treated with 130 µL of OPTI-MEM-1 containing 12 µg/mL LIPOFECTIN™ (Gibco BRL) and the dsRNA at the desired concentration. After 5 hours of treatment, the medium was replaced with fresh medium. Cells were harvested 16 hours after dsRNA treatment, at which time RNA was isolated and target reduction measured by RT-PCR as described in previous examples.

Example 14

Northern Blot Analysis of Target RNA Levels

Eighteen hours after treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBONDT™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect a target, a target specific primer/probe set is prepared for analysis by PCR. To normalize for variations in loading and transfer efficiency, membranes are stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Oligomeric Compounds Targeting Nucleic Acids

In accordance with the present invention, a series of oligomeric compounds are designed to target different regions of target nucleic acids. The oligomeric compounds can be investigated for their effect on nucleic acid target levels by quantitative real-time PCR as described in other examples herein. The target regions to which these sequences are complementary are herein referred to as "suitable target regions."

According to the present invention, oligomeric compounds include antisense oligomeric compounds, antisense oligonucleotides, ribozymes, siRNAs, external guide sequence (EGS) oligonucleotides, alternate splicers, primers, probes, and other short oligomeric compounds that hybridize to at least a portion of the target nucleic acid.

Example 16

Oligomeric Compounds that Mimic or Replace Nucleic Acid Targets

In accordance with the present invention, a series of oligomeric compounds are designed to mimic the structure or function of a nucleic acid target. These mimics may include isolated single-, double-, or multiple-stranded compounds, any of which may include regions of intrastrand nucleobase complementarity, said regions capable of folding and forming a molecule with fully or partially double-stranded or multiple-stranded character based on regions of perfect or imperfect complementarity. The oligomeric compound mimics can then be investigated for their effects on a cell, tissue or organism system lacking endogenous small untranslated RNAs or systems with aberrant expression of nucleic acid targets by screening methods disclosed herein or those commonly used in the art. Changes in expression levels of the nucleic acid target or its downstream target levels can be analyzed by quantitative real-time PCR as described in other examples herein.

Example 17

Western Blot Analysis of Protein Levels

When target nucleic acids have effects on the expression of downstream genes or proteins encoded by genes, it is advantageous to measure the protein levels of those gene products. To do this, Western blot analysis is employed.

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gradient gels (4-20%) may also be used for the separation of proteins, as is well known in the art. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 18

Nucleic Acids Targeted by Compounds of the Present Invention

In accordance with the present invention, a series of oligonucleotides were designed to target different regions of the human peroxisome proliferator-activated receptor gamma RNA, using published sequences (GenBank accession number AB005520, SEQ ID NO:4). The target sequence represents an mRNA encoded by the PPAR-γ gene.

Example 19

Uniform 2'-MOE Phosphorothioate (PS) Oligomeric Compounds Targeting Nucleic Acid Targets In accordance with the present invention, a series of oligomeric compounds were designed and synthesized to target nucleic acid targets. All compounds are composed of 2'-O-methoxyethyl (2'-MOE) nucleotides throughout and the internucleoside (backbone) linkages are phosphorothioate (P=S) throughout. All cytidine residues are 5-methylcytidines. The compounds can be analyzed for their effect on target nucleic acid or precursor levels by quantitative real-time PCR as described in other examples herein or they can be used in other assays to investigate the role of nucleic acid targets or the function of targets downstream of the targets.

Example 20

Chimeric Phosphorothioate Compounds Having 2'-MOE Wings and a Deoxy Gap Targeted to Nucleic Acid Targets In accordance with the present invention, a series of oligomeric compounds was designed and synthesized to target different regions of target nucleic acids. In some embodiments, chimeric oligonucleotides ("gapmers") are nucleotides in length, composed of a central "gap" region consisting of ten 2'-deoxynucleotides, which is flanked on both sides (5' and 3' directions) by five-nucleotide "wings." The wings are composed of 2'-methoxyethoxy (2'-MOE) nucleotides. The internucleoside (backbone) linkages are phosphorothioate (P=S) throughout the oligonucleotide. All cytidine residues are 5-methylcytidines. The compounds can be analyzed for their effect on nucleic acid targets or precursor levels by quantitative real-time PCR as described in other examples herein or they can be used in other assays to investigate the role of nucleic acid targets or their downstream targets. For example, a series of 78 different oligomeric compounds was evaluated for their ability to reduce expression levels of the PPAR-γ mRNA. As a control a 20-mer oligonucleotide random-mer, ISIS-29848 (NNNNNNNNNNNNNNNNNNNN; where N is A, T, C or G; SEQ ID NO:10) was used. A 2'-MOE 5-10-5 chimeric gapmer oligomeric compound targeting the PPAR-γ mRNA is ISIS Number 105990 (AGCAAAAGATCAATCCGTTA; SEQ ID NO:11)), with an extinction coefficient of 211.52 and molecular weight of 7220.279 Da, was identified, using standard screening protocols, to be active and effectively reduce target expression. It is understood that a person having ordinary skill in the art would be able to convert the sequence of the targets to their RNA form by simply replacing the thymidine (T) with uracil (U) in the sequence.

Example 21

Adipocyte Assay of Oligomeric Compounds

The effect of several oligomeric compounds of the present invention targeting nucleic acids on the expression of markers of cellular differentiation was examined in preadipocytes.

One of the hallmarks of cellular differentiation is the upregulation of gene expression. Several changes are known to occur in human pre-adipocytes undergoing the cellular differentiation process. These changes include the accumulation of triglycerides as lipid droplets, the secretion of several hormones and autocrine factors (e.g., leptin and TNF-alpha), and characteristic changes in gene expression. During adipocyte differentiation, the gene expression patterns in adipocytes change considerably. An excessive recruitment and differentiation of preadipocytes into mature adipocytes is a characteristic of human obesity, which is a strong risk factor for type II diabetes, hypertension, atherosclerosis, cardiovascular disease, and certain cancers. Some genes known to be upregulated during adipocyte differentiation include hormone-sensitive lipase (HSL), adipocyte lipid binding protein (aP2), glucose transporter 4 (Glut4), and PPAR-γ. These genes play important roles in the uptake of glucose and the metabolism and utilization of fats. For example, HSL is involved in the mobilization of fatty acids from adipose tissue into the bloodstream; studies suggest that increased free fatty acid levels are one of the causative factors in type II diabetes. aP2 is believed to play a role in atherosclerosis. Glut4 is important in insulin signaling. PPAR-γ is believed to be involved in adipocyte differentiation, insulin sensitivity, and colonic tumor development.

Leptin is also a marker for differentiated adipocytes. In the adipocyte assay, leptin secretion into the media above the differentiated adipocytes was measured by protein ELISA. Cell growth, transfection and differentiation procedures were carried out as described for the Triglyceride accumulation assay (see below). On day nine post-transfection, 96-well plates were coated with a monoclonal antibody to human leptin (R&D Systems, Minneapolis, Minn.) and left at 4° C. overnight. The plates were blocked with bovine serum albumin (BSA), and a dilution of the media was incubated in the plate at RT for 2 hours. After washing to remove unbound components, a second monoclonal antibody to human leptin (conjugated with biotin) was added. The plate was then incubated with strepavidin-conjugated HRP and enzyme levels are determined by incubation with 3, 3', 5, 5'-Tetramethlybenzidine, which turns blue when cleaved by HRP. The $OD_{450}$ was read for each well, where the dye absorbance is proportional to the leptin concentration in the cell lysate. Results are expressed as a percent±standard deviation relative to transfectant-only controls.

An increase in triglyceride content is another well-established marker for adipocyte differentiation. The triglyceride accumulation assay measures the synthesis of triglyceride by adipocytes. Triglyceride Accumulation was measured using the Infinity™ Triglyceride reagent kit (Sigma-Aldrich, St. Louis, Mo.). Primary human preadipocytes (Zen-Bio Inc., Research Triangle Park, N.C.) were used for an in vitro model of adipocyte differentiation. Using methods known in the art, differentiation was induced by a combination of insulin, dexamethasone, a PPAR-γ agonist, and a compound that increases intracellular levels of cyclic AMP. Under these conditions, a time-dependent increase in triglyceride accumulation and an increase in leptin secretion was observed. Furthermore, expression levels of several genes known to be induced during differentiation, including the transcription factors c/EBP alpha, aP2, Glut4, and HSL were all increased.

Effects of inhibiting nucleic acid target expression on hallmark gene expression during adipocyte differentiation:

Using the in vitro model of adipocyte differentiation (described supra), the oligomeric compound ISIS 105990 (SEQ ID NO:11), known to reduce expression levels of PPAR-γ mRNA, was tested for its effects on the expression of hallmark genes during adipocyte differentiation. Human preadipocytes were cultured up to 80% confluence in preadipocyte media (Zen-Bio Inc.). One day before transfection, 96-well plates were seeded with 3000 cells/well. Cells were transfected according to standard published procedures with 250 nM oligonucleotide in 10 µl/ml LIPOFECTIN™ (Invitrogen Corporation, Carlsbad, Calif.) in serum free medium for 4 hours at 37° C. (Monia et al., *J. Biol. Chem.* 1993 268, 14514-22). Antisense oligonucleotides were tested in triplicate on each 96-well plate, and the effects of TNF-alpha, a positive control drug known to inhibit adipocyte differentiation, were also measured in triplicate. Negative antisense and transfectant-only controls may be measured up to six times per plate. After the cells have reached confluence (approximately three days), they were exposed to differentiation media (DM) (Zen-Bio, Inc.) containing a PPAR-γ agonist, IBMX, dexamethasone, and insulin for three days. Cells were then fed adipocyte media (Zen-Bio, Inc.), which was replaced at 2 to 3 day intervals. On day nine post-transfection, cells were washed and lysed at room temperature, and the triglyceride assay reagent was added. Triglyceride accumulation was measured based on the amount of glycerol liberated from triglycerides by the enzyme lipoprotein lipase. Liberated glycerol is phosphorylated by glycerol kinase, and hydrogen peroxide is generated during the oxidation of glycerol-1-phosphate to dihydroxyacetone phosphate by glycerol phosphate oxidase. Horseradish peroxidase (HRP) uses $H_2O_2$ to oxidize 4-aminoantipyrine and 3,5 dichloro-2-hydroxybenzene sulfonate to produce a red-colored dye. Dye absorbance, which is proportional to the concentration of glycerol, was measured at 515 nm using an UV spectrophotometer. Glycerol concentration was calculated from a standard curve for each assay, and data were normalized to total cellular protein as determined by a Bradford assay (Bio-Rad Laboratories, Hercules, Calif.). Results are expressed as a percent±standard deviation relative to transfectant-only control.

Firstly, we confirmed a dose-dependant ASO mediated reduction in PPAR-γ mRNA expression. For assaying adipocyte differentiation, expression of the four hallmark genes, HSL, aP2, Glut4, and PPAR-γ, as well as triglyceride (TG) accumulation and leptin secretion are measured in adipocytes transfected with the 2'-MOE chimeric phosphorothioate (PS) oligomeric compound previously described. Cells are lysed on day nine post-transfection, in a guanadinium-containing buffer and total RNA is harvested. The amount of total RNA in each sample is determined using a Ribogreen Assay (Molecular Probes, Eugene, Oreg.). Real-time RT-PCR is performed on the total RNA using primer/probe sets for the adipocyte differentiation hallmark genes Glut4, HSL, aP2, and PPAR-γ. Leptin protein and triglyceride levels as well as mRNA levels for each of the four adipocyte differentiation hallmark genes are expressed as a percentage of control levels (control=treatment with ISIS-29848 (SEQ ID NO:10)).

It was observed that treatment of preadipocytes with ISIS Number 105990 inhibited PPAR-γ mRNA expression in a dose-dependent manner. At a concentration of 200 nM of ISIS 105990, PPAR-γ mRNA levels dropped below 40% relative to untreated controls, while preadipocytes transfected with 200 nM of the negative control, ISIS 29848, expressed >90% PPAR-γ mRNA relative to the untreated control. Furthermore, it was observed that the expression of the aP2 and HSL hallmark genes were reduced to 55% and 32%, respectively, relative to untreated control levels. Therefore, the oligomeric compound ISIS Number 105990 was used in further studies to assess the global gene expression using Affymetrix GeneChip microarrays.

Example 22

Identification of PPAR-γ Responsive Genes

As described supra, ISIS Number 105990 (SEQ ID NO:11) is an chimeric oligomeric compound that effectively reduces the expression of PPAR-γ and is thus able to block the in vitro differentiation of human white preadipocytes into adipocytes. ISIS 105990 was transfected into preadipocytes and agents added to induce differentiation. After differentiation, Total RNA was harvested from the cells treated with oligomeric compound, as well as from untreated cells and cells treated with ISIS 29848, a negative control oligomeric compound using the RNEASY 96™ kit (Qiagen Inc., Valencia, Calif.). Samples were prepared for hybridization according to the Affymetrix Expression Analysis Technical Manual, and global gene expression was then determined using Affymetrix U133A GeneChip microarrays and Affymetrix Microarray Suite version 5.

The study included RNA isolated from the following 5 treatment groups: (1) preadipocytes before differentiation, (2) differentiated adipocytes, (3) mock-transfected preadipocytes differentiated into adipocytes, (4) ISIS 29848 (negative control)-transfected preadipocytes differentiated into adipocytes, and (5) ISIS 105990 (targeted to PPAR-γ)-transfected preadipocytes differentiated into adipocytes. Experiments were performed in triplicate for each treatment group.

Using Affymetrix Microarray Suite version 5, one-way analysis of variance was conducted followed by pre-planned pairwise comparisons as post-hoc analysis. Two-tailed two-sample t-test was conducted and the resulting p-values were adjusted using the Benjamini-Hochberg procedure in order to control false discovery rate (FDR), which is the expected proportion of erroneous significance calls among all the significance calls. A cut-off of FDR≦0.2 was used to generate 278 significantly down-regulated genes and 292 significantly up-regulated genes after PPAR-γ knock-down. Principal component analysis and hierarchical cluster analysis were utilized as global data quality check and exploratory analysis tools.

A sequence was then extracted from the GenBank record of up to 10,000 bases upstream of the first CDS coordinates. The sequences were then run through a parallel set of analyses designed to detect any motif similarities such as common transcription factor binding sites. The putative promoter regions of the 182 statistically significant down-regulated genes were extracted and analysed with a perl script written in-house called 'probe2promoter' which uses BLAST to find hits of the Affymetrix probe sequences and matching them to their appropriate genome locations.

Given a FASTA file of probe sequences (typically Affymetrix probe sequences), this program extracts promoter sequences for the genes they touch in a specified genome.

The following 6 steps summarize the promoter extraction process:

1. The probe sequence is BLASTed against the genome's chromosome contigs to locate the contig on which its gene resides. The location of the of the probe sequence is taken to be the range of the first HSP of the highest ranking hit found by BLAST.

2. The annotation in the GenBank flat file for the hit contig is searched for a gene whose range overlaps the range of the probe sequence. If probe sequence range overlaps more than one gene feature, the first one found is used.

3. The annotation is searched for the CDS feature belonging to the hit gene. This is assumed to be the first CDS feature found with the same gene name as the hit gene feature. The gene name is taken to be the value of the/gene qualifier. Note that the gene-to-coding sequence (CDS) lookup is done solely on the basis of the gene name. If the gene name is missing in either feature or is not unique on the contig, then the lookup may fail.

4. The promoter region is taken to be the N nucleotides 5' of the CDS start, where the default for N is 10000. This can be changed via the--promoter_length option.

5. The FASTA record containing the contig sequence is fetched, and the subsequence representing the promoter region is extracted using the coordinates calculated in step 4.

6. The promoter sequence is written to standard output as a FASTA record. The first analysis was a simple search for PPAR-γ binding sites using perl regular expressions. PPAR-γ binding element (PPRE) in the promoter region of the Lipoprotein Lipase gene (LPL) and Malic Enzyme 1 was previously characterized in literature (Schoonjans ET AL., Embo J., 1996, 15, 5336-48. As expected, a number of genes were found to contain this consensus PPRE elements in their promoter regions. One of these was hypothetical protein FLJ20920; hypothetical protein FLJ20920 is the closest human ortholog of a gene previously reported as a key weight control genes in *C. elegans* (Ashrafi et al, Nature, 2003, 421, 268-72).

The final analysis involves the use of MEME to predict common sequence motifs in the sequences. MEME is a tool for discovering motifs in a group of related DNA or protein sequences. MEME represents motifs as position-dependent letter-probability matrices which describe the probability of each possible letter at each position in the pattern. Common sequence motifs are aligned and clustered using a modified Smith-Waterman algorithm in which each motif is treated as a single residue, so that a series of linearly conserved motifs can be aligned with other similarly arranged motifs (Waterman et al., J. Mol. Biol., 1987, 197, 723-8; and Karchin et al., Bioinformatics, 1998 14, 772-82). The result is a visual alignment and cluster of sequences with similar motif patterns. Using this analysis, 30 genes were identified in three different clusters that show highly conserved sequence motifs. Each cluster was refined using Hidden Markov Models software (HMMER) and several other sequences were mined out which show similarity to this motif pattern. FIG. 1 of the drawings shows an example of a MEME cluster defined using the MAST/MEME algorithm.

Using this data integration method, the following data resulted. Analysis of this global gene expression data using allowed the identification of a total of 278 genes which were statistically significantly downregulated, and 292 genes which were significantly upregulated in the cells treated with the oligomeric compound targeted to the PPAR-γ mRNA target as compared to cells treated with the negative control oligo. Of these, the 278 significantly (FDR≦1.2) down-regulated genes were probed by MAPPFinder (Doniger et al., Genome Biol., 2003, 4, R7), a functional annotation tool based on Gene Ontology (GO) (Ashburner et al., Nat. Genet., 2000, 25, 25-9) database. Interesting GO terms were ranked by z-score. Positive z scores indicate GO terms with a greater number of genes meeting a given criterion than is expected by chance. For example, a) adipocyte differentiation b) lipid metabolism and c) fatty acid metabolism came with z-scores of 5.9, 4.2, and 3.0, respectively. This suggests that the number of genes falling into these GO categories among the down-expressed genes is more than expected by just random chance. The three GO terms with high z-scores in MAPPFinder were further examined by GenMAPP (Dahlquist et al., Nat. Genet., 2002, 31, 19-20). The GenMAPP GO pathways identified Lipin 1 for adipocyte differentiation, ACAD8, AKR1C3, ALDH3A2, and ALDH3B1 for lipid metabolism and CD36, HADHA, and AKR1C3 as for fatty acid metabolism genes.

The same method was applied for the PPAR-γ up-regulated genes. Two hundred and ninety-one statistically significant (FDR≦0.2) up-regulated genes were used for this analysis. MAPPFinder searches of the 291 up-regulated genes show that insulin-like growth factor binding and proteoglycan are two of the most significant GO categories. The GenMAPP GO Pathway of insulin-like growth factor binding identified CTGF and CYR61. For proteoglycan, CSPG2 and PRG1 were identified.

Additionally, literature and genomic database searches were used to identify and compile a set of genes that are predicted to be involved in adipocyte differentiation. The results are summarized below in Table 2. Genes containing a PPRE motif are indicated in boldface while the genes identified in MEME cluster#1 are shown in italics.

TABLE 2

| Gene | Fold Change | P-value | Affymetrix ID | GenBank ID |
| --- | --- | --- | --- | --- |
| TRIP15 thyroid receptor interacting protein 15 | −1.1866 | <0.0001 | 202467_s_at | NM_004236.1 |
| PFKFB3 6-phosphofructo-2-kinase/fructose-2,6-biphosphatase 3 | −1.5328 | 0.0001 | 202464_s_at | NM_004566.1 |
| PLIN perilipin | −1.3468 | 0.0001 | 205913_at | NM_002666.1 |
| HADHA hydroxyacyl-Coenzyme A dehydrogenase/3-ketoacyl-Coenzyme A thiolase/enoyl-Coenzyme A hydratase (trifunctional protein), alpha subunit | −1.2517 | 0.0001 | 208631_s_at | U04627.1 |
| LIPE lipase, hormone-sensitive | −1.4068 | 0.0002 | 213855_s_at | AI500366 |
| ALDH9Al aldehyde dehydrogenase 9 family, member Al | −1.1489 | 0.0003 | 201612_at | NM_000696.1 |
| FLJ20920 hypothetical protein FLJ20920 | −1.2777 | 0.0003 | 218844_at | NM_025149.1 |
| INSIG1 insulin induced gene 1 | −1.2155 | 0.0006 | 201625_s_at | BE300521 |
| HADHB hydroxyacyl-Coenzyme A | −1.2598 | 0.0007 | 201007_at | NM_000183.1 |
| ACAA2 acetyl-Coenzyme A acyltransferase 2 | −1.3096 | 0.0007 | 202003_s_at | NM_006111.1 |
| CAV2 caveolin 2 | −1.2795 | 0.0007 | 203323_at | BF197655 |
| LPL lipoprotein lipase | −1.2435 | 0.0007 | 203549_s_at | NM_000237.1 |
| MDH1 malate dehydrogenase 1, NAD (soluble) | −1.2253 | 0.0008 | 200978_at | NM_005917.1 |
| EGFL5 EGF-like-domain, multiple 5 | −1.3928 | 0.0014 | 212830_at | BF110421 |
| ALDH3A2 aldehyde dehydrogenase 3 family, member A2 | −1.1953 | 0.0017 | 202053_s_at | L47162.1 |
| UQCRFSI ubiquinol-cytochrome c reductase, Rieske iron-sulfur polypeptide 1 | −1.202 | 0.0017 | 208909_at | BC000649.1 |
| CEBPA CCAAT/enhancer binding protein (C/EBP) alpha | −1.4737 | 0.0022 | 204039_at | NM_004364.1 |
| UCP2 uncoupling protein 2 (mitochondria], proton carrier) | −1.4688 | 0.0024 | 208998_at | U94592.1 |
| ALDH3B1 aldehyde dehydrogenase 3 family, member B1 | −1.9524 | 0.0025 | 211004_s_at | BC002553.1 |
| MYLK myosin, light polypeptide kinase | −1.3622 | 0.0028 | 202555_s_at | NM_005965.1 |
| FHLl four and a half LIM domains 1 | −1.2233 | 0.003 | 210298_x_at | AF098518.1 |
| FACL1 fatty-acid-Coenzyme A ligase, long-chain 1 | −1.2156 | 0.0031 | 207275_s_at | NM_001995.1 |
| ACAD8 acyl-Coenzyme A dehydrogenase family, | −1.2044 | 0.0033 | 221669_s_at | BC001964.1 |
| PYGL phosphorylase, glycogen; liver (Hers disease, glycogen storage disease | −1.139 | 0.0037 | 202990_at | NM_002863.1 |
| ME1 malic enzyme 1, NADP(+)-dependent, cytosolic | −1.1488 | 0.0039 | 204059_s_at | NM_002395.2 |
| MAPK1O mitogen-activated protein kinase 10 | −1.3834 | 0.0043 | 204813_at | NM_002753.1 |
| CASP7 caspase 7, apoptosis-related cysteine protease | −1.3295 | 0.0044 | 207181_s_at | NM_001227.1 |
| PDHA1 pyruvate dehydrogenase (lipoamide) alpha 1 | −1.1803 | 0.0048 | 200980_s_at | NM_000284.1 |
| ACLY ATP citrate lyase | −1.2334 | 0.0049 | 210337_s_at | U18197.1 |
| EBP emopamil binding protein (sterol isomerase) | −1.3361 | 0.0051 | 213787_s_at | AV702405 |
| MKNK1 MAP kinase-Interacting serine/threonine kinase | −1.2113 | 0.0053 | 209467_s_at | BC002755.1 |
| FLJ10079 hypothetical protein FLJI0079 | −1.4118 | 0.0055 | 220236_at | NM_017990.2 |
| COX1O COX1O homolog, cytochrome c oxidase assembly protein, heme A: farnesyltrdnsferase (yeast) | −1.2962 | 0.0056 | 203858_s_at | NM_001303.1 |
| GHITM growth hormone Inducible transmembrane protein | −1.1205 | 0.0059 | 209249_s_at | AF131820.1 |
| ALDH4A1 aldehyde dehydrogenase 4 family, member Al | −1.3525 | 0.0059 | 211552_s_at | U24267.1 |
| CD36 CD36 antigen (collagen type I receptor, thrombospondin receptor) | −1.1907 | 0.0069 | 206488_s_at | NM_000072.1 |
| Bifunctional protein (enoyl-CoA hydratase) | −1.2598 | 0.0007 | 201007_at | NM_000183 |
| HMG-CoA synthetase | −1.3982 | 0.0018 | 205822_s_at | NM_002130 |
| Apolipoprotein E | −1.286 | 0.014 | 203381_s_at | NM_000041 |
| Notch homolog 3 (*Drosophila*) | −1.4289 | 0.0025 | 203238_s_at | NM_000435 |
| glycerol-3-phosphate dehydrogenase 1 (soluble) | −1.3135 | 0.0067 | 204997_at | NM_005276 |
| very low density lipoprotein receptor | −1.2574 | 0.002 | 209822_s_at | NM_003383 |

Because adipogenesis is believed to be controlled and regulated by the binding of PPAR-γ to the promoter DNA sequence, the identification of common cis-regulatory sequences in the downstream targets of PPAR-γ in human primary adipocytes was a primary goal. The putative promoter regions of the 182 statistically significant down-expressed genes were extracted using a PERL script written in-house called 'probe2promoter' (described supra). This script uses BLAST to find hits of the Affymetrix probe sequences to their appropriate genome locations. The GenBank records of each hit contig are then searched for a corresponding mRNA, gene, or CDS that lies in the probe location. A sequence is then extracted from the GenBank record of up to 10,000 bases upstream of the first CDS coordinates. The sequences were then run through a series of separate analyses designed to detect any motif similarities such as common transcription factor binding sites.

PPAR-γ Response Element (PPRE):

A simple search of PPAR-γ binding sites in the upstream sequences using PERL regular expressions was performed.

Previously documented PPRE elements were found in the promoters of 6 genes. PPRE elements in ME1 and LPL have been earlier characterized. The remaining four genes containing PPRE elements in their promoters are as follows:

Probe 210298_x_at, Gene FHL1: four and a half LIM domains 1, Genomic Coordinates NT_011786.11: 10846850.10856849

Perfect match to the consensus PPRE element "TGACCT-nTGACCT" (SEQ ID NO:5).

5'AAAGTTTCAGAGCAGGAATGAAAG-TAAAGTACATTTAGAAGATGACCAAGCA GGCTACT-TGAGAGATTCAAAAAGTGCATGGTT TGACCTTTGACCTGGGCTTTTAT ATGTTGGC 3' (SEQ ID NO:12)

Probe 209249_s_at, Gene GHITM:PTD010 protein, Genomic Coordinates NT_033890.3:4331794.4341793.

PPRE is identical to what is identified in the promoter of Acyl-CoA Oxidase (ACO) gene "TGACCTTGTCCT" (SEQ ID NO:13).

5'TTGGTTTCCTCTTGGAAGACTGACCA-GAAAGCATGACACTAGTCTCAATTTTCT GCCAATATCTGTCCCTCCACAGATAC-TACCCCACTAATGACCTTGTCCTTTGGCCC ACTTA-CAGCA 3' (SEQ ID NO:14).

Probe 218844_at, Gene FLJ20920: hypothetical protein FLJ20920, Genomic Coordinates NT_010783.11: 2918469.2928468.

PPRE is identical to what is found in the promoter of L-fatty acid binding protein (1-FABP), "TGACCTTG-GCCT" (SEQ ID NO:15).

5'TTTCTTCTTTCTTTGGAGGCAGAAAT-TGGGCATAAGACAATATGAGGGGTGGTC TCCTC-CCTTATCGCCATGTTGACCAAGCTG-GTCTCAAACTCCTGACCTTGGCCTCC CAAAT 3' (SEQ ID NO:16).

Probe 220236_at, Gene FLJ10079: hypothetical protein FLJ10079, Genomic Coordinates NT_037896.1: 418879.428878.

PPRE is identical to what is found in the promoter of Acyl-CoA Oxidase (ACO) "TGACCTTGTCCT" (SEQ ID NO:17).

5'GCTGTTTCTTGTAGGGTATTCTAAATCA-GAAACCTACACTTAGTCTGCAAATAG AAGCCTGTG TGACCTTGTCCTTCCTCCACACTGGGTTGATGGGT-GCTATCCTGGTC AGGA 3' (SEQ ID NO:18).

Transcription Factor Binding Sites:

It was further determined if there were any other transcription factor binding sites common to a significant number of sequences. The algorithm TFBIND was used to search each sequence for putative transcription factor binding sites. At the same time, TFBIND was used to calculate putative transcription factor binding sites to the entire Eukaryotic Promoter Database (EPD). The results of the 182 putative promoter regions were then compared with those derived from the EPD. It was observed that several transcription factor binding sites were much more likely to occur in the sequences identified by the compositions and methods of the present invention than in the sequences derived from the EPD—namely, binding sites were found for ectopic viral integration site Evi-1 factors, myogenic MADS MEF-2 factors, and hepatocyte nuclear and Oct-1 factors. How these binding sites might relate to each other positionally is the subject of ongoing work.

MAST/MEME Motifs:

A MEME analysis was then performed to predict common sequence motifs in the upstream promoter regions. Using the relatively short PPAR-γ recognition sequence (PPRE) as an example, it was believed that common functional regulatory regions in the DNA upstream of the promoter would more likely consist of small, highly-conserved motifs rather than long, divergent motifs. Thus, the MEME input parameters reflected this hypothesis. The 20 best motifs were chosen as output, with each not exceeding 20 basepairs in length. Because 20 motifs distributed over more than one hundred sequences can be difficult to interpret visually, the motif distribution was aligned and clustered using a modified Smith-Waterman algorithm so that a series of linearly conserved motifs can be aligned with other similarly arranged motifs. The result was a visual alignment and cluster of sequences with similar motif patterns (FIG. 1). Using this analysis, 30 genes in three different clusters that show highly conserved sequence motifs were identified. The largest cluster contains 19 genes, and of these, the ALDH9A1, COX10, PLIN, FACL1, Notch3, SLC7A6 and EBP genes have been reported to be involved in fatty acid metabolism. Also notable was the discovery of the *Drosophila* serpent (SRP) gene homolog SRP72 in the second major MEME cluster. It has been documented that serpent gene is critical for fat body formation in *Drosophila*.

Each cluster was further refined using Hidden Markov Models (HMMER) and several other sequences that show similarity to each motif pattern were also identified. Laboratory experiments using cell culture will further validate the function of these motifs. Once a motif is found, it is necessary to be able to identify it as a known transcription factor binding site (TFBS) or sites. In general, the motifs found by MEME are larger than typical transcription factor binding sites. Therefore, each sequence in each MEME motif is searched using TFBIND to mine out any known transcription factor binding sites. However, even after searching through the sets of known transcription factor binding sites that TFBIND provides, some high information-content motif regions remain unassociated with any transcription factor binding sites. Thus, it may be possible that the motifs found by MEME are, in fact, regulatory in nature but have not yet been categorized and therefore are not present in the TRANSFAC database.

Phylogenetic Footprints:

Comparison of orthologous gene sequences has emerged as a powerful tool in genome analysis. Phylogenetic footprinting provides complementary data to computational predictions, as sequence conservation over evolution highlights segments in genes likely to mediate biological functions (Rennert et al., BMC Evol. Biol., 2003, 3, 4). An additional approach was to look for phylogenetic footprints (syntenic regions) in the promoter regions of the 182 down-expressed human genes and their corresponding mouse homologues to search for conserved transcription factor binding sites. Evolutionarily conserved upstream promoter sequences of human and mouse genes are believed to share common regulatory motifs. These cross-species conserved motifs are most likely to be the targets for important regulatory factors. Three genes (ALDH9A1, EBP and PLIN) identified in the primary MEME cluster by the GemomeVista program have been carefully analyzed by phylogenetic footprinting. Eleven kilobases of upstream sequence of the first exon of both mouse and human genes was aligned using GenomeVista. In the ALDHA1 promoter, two highly conserved regions were detected at the positions at −8750 by and −10400 bp. Both conserved regions show a high affinity to signal transducers and activators of transcription (STAT) and CCAAT Enhancer Binding Protein (CEBP) transcription factors. Similarly, the upstream sequence of PLIN contains a large conserved region (500 bp) in the position around −5500 bp where there appears to be many STAT and GATA recognition sites and also, a region of high conservation (>75%) between human and mouse upstream of the EBP gene shows a high affinity to transcription factor STAT.

It is known that the constitutive GATA expression suppresses adipocyte differentiation and keeps cells at the preadipocyte stage. This effect is mediated through the direct suppression of PPARγ (Tong et al., Science, 2000, 290, 134-8). Phylogentic footprinting studies reveal that the PLIN promoter contains several perfect GATA binding motifs in its phylogenetic footprint located −5500 by upstream of the first exon.

Recent data demonstrated that perilipin (encoded by the gene PLIN) results in leanness and reverses obesity in mice (Martinez-Botas et al., Nat. Genet., 2000, 26, 474-9). PLIN was identified as one of the adipogenesis related genes in the primary MEME cluster. Results discussed by Martinez-Botas J and others (Martinez-Botas et al., Nat. Genet., 2000, 26, 474-9) demonstrate that agents that could inactivate perilipin may prove useful as anti-obesity medications. Thus, from these data integration strategies, gene regulatory sequences and gene families have been predicted, and it can be further determined whether PPAR-γ or another transcription factor binds to these motifs, by ChIP/chip array, gel shifts assays and biotin pull-down experiments (described in examples below).

Example 23

ChIP/Chip Assay

As is known in the art, Chromatin immunoprecipitation (ChIP) is a procedure used to investigate interactions between proteins and DNA. Recently, methods that combine well-established protocols for chromatin immunoprecipitations (Boyd et al., Proc. Natl. Acad. Sci. U.S.A., 1998, 95, 13887-92; Wells et al., Mol. Cell. Biol., 2000, 20, 5797-807; Albert et al., J. Biol. Chem., 2001, 276, 20482-90; Maser et al., Mol. Cell. Biol., 2001, 21, 6006-16; Weinmann et al., Genes Dev., 2002, 16, 235-44; Wells et al., Methods, 2002, 26, 48-56; Wells et al., Proc. Natl. Acad. Sci. U.S.A., 2002, 99, 3890-5; Wells et al., Oncogene, 2003, 22, 1445-60) with the surveying power of DNA microarrays have allowed researchers to create high-resolution, genomewide maps of the interaction between DNA-associated proteins and DNA. Many variations of the method have been used but all contain the same basic steps: growth of cells, fixation, extract preparation, immunoprecipitation, fixation reversal, DNA purification, DNA amplification, microarray hybridization, and data analysis.

PPAR-γ is first crosslinked at its sites of interaction with DNA. This is accomplished quickly and efficiently by adding formaldehyde directly to the living cells (preadipocytes and adipocytes) in the culture. Crude extract from these fixed cells are then prepared, sonicated to shear chromatin to an average size of approximately 1 kb, and then used in immunoprecipitation reactions with antibodies raised against PPAR-γ DNA fragments enriched in immunoprecipitation are then purified, amplified with a degenerate-primer PCR-based method, fluorescently labeled and hybridized to DNA promoter microarray.

In particular, preadipocytes and differentiated adipocytes were prepared as described above, and the cells were crosslinked with a 1% formaldehyde solution for 10 min at 37° C. After being washed two times with cold PBS containing protease inhibitor cocktails (Roche), the cells were processed following the ChIP assay kit protocol (Upstate Biotechnology). For immunoprecipitation, protein extracts were incubated with 10 µg of polyclonal antibodies for PPARγ (SC-7196; Santa Cruz Biotechnology) or normal rabbit IgG for 40 h at 4° C., followed by 2 h incubation with salmon sperm DNA/Protein A agarose slurry on the rocker. After extensive washing, the immune/DNA complex was eluted in 500 µl of buffer (1% SDS, 0.1 M NaHCO$_3$), reverse-crosslinked at 65° C. for 4 h, and subjected to proteinase K (Ambion) digestion at 45° C. for 1 h. Samples were extracted with phenol-chloroform-isoamylalcohol, ethanol-precipitated overnight at −80° C., and the DNA was resuspended in water. Samples were analyzed by PCR using Accuprime II (Invitrogen) Tag polymerase in the presence of $^{32}$P-dCTP. The PCR products were separated on 6% Tris-borate-EDTA (TBE)-PAGE, dried, and exposed to X-ray film at −80° C. The primers used for PCR are as follows: acetyl-CoA oxidase (ACOX) CTCAGCAAATTTAGCTCTTCATC (forward; SEQ ID NO:19), CCTTCAACAGCAGAGAGGGTGTC (reverse; SEQ ID NO:20); GHITM, GCTACTACAATTTCTGAGT-GTTGG (forward; SEQ ID NO:21), GGCCTTGAAAAT-GACATCGATGGCAG (forward; SEQ ID NO:22); FLJ10079, CAGATATCAGTAACTACGCTG (forward; SEQ ID NO:23), GAATGAAATGTAACATCAAGACC (reverse; SEQ ID NO:24); FLJ20920, GGAGGCAGAAAT-TGGGCATAAGAC (forward; SEQ ID NO:25), GTCTTA-CAGTTCTGGAGGCCAG (reverse; SEQ ID NO:26); FLJ20920-control, CAGGACTAGATGCAAACCTCCAG (forward; SEQ ID NO:27), CATTGAGTAACTACTTGCT-GAC (reverse; SEQ ID NO:28).

Example 24

Gel Mobility Shift Assay

Nuclear extracts from human Adipocyte cells are prepared. It can then be determined whether the novel motifs are functional binding sites for particular transcription factors (PPAR-γ or other transcription factors). DNA fragments from digested PCR product (putative regulatory motifs, about 200-500 bp) can be labeled and subjected to the DNA mobility shift assays, using protocols well known in the art, alongside competitive binding assays with various oligonucleotides corresponding to the consensus sequences found on the predicted promoter region to observe a reversal of the mobility shifted complexes and demonstrate that the binding is specific. Although multiple complexes may formed, if the complexes are observed to be competed out by certain oligonucleotides, such a result indicates these motifs or regions is are the major protein binding sites. Binding constants can also be determined using methods known in the art.

Nuclear extracts can be prepared as follows: Cells are incubated in serum-free media for 24 hrs, and washed with cold phosphate-buffered saline twice and scraped into 1 ml of cold phosphate-buffered saline. Cells are pelleted by microcentrifugation for 10 seconds and incubated in 2 packed-cell volumes of buffer A (10 mM HEPES, pH 8.0, 0.5% Nonidet P-40, 1.5 mM MgCl$_2$, 10 mM KCl, 0.5 mM DTT, and 200 mM sucrose) for 5 minutes at 4° C., occasionally flicking the tube. The crude nuclei will be collected by microcentrifugation for 15 seconds; these pellets are rinsed with buffer A, resuspend in 1 packed-cell volume of buffer B (20 mM HEPES, pH 7.9, 1.5 mM MgCl$_2$, 420 mM NaCl, 0.2 mM EDTA, and 1.0 mM DTT), and incubated on a rocking platform for 30 min at 4° C. Nuclei can be clarified by microcentrifugation for 5 minutes, and the supernatants are diluted 1:1 with buffer C (20 mM HEPES, pH 7.9, 100 mM KCl, 0.2 mM EDTA, 20% glycerol, 1 mM DTT). Protease inhibitors (1 mM phenylmethylsulfonyl fluoride, 50 mg of both aprotinin and leupeptin/ml) and phosphatase inhibitors (10 mM NaF, 10 mM b-glycerophosphate, 0.1 mM sodium orthovanadate, and 1 mM EGTA) are added to each type of buffer. Nuclear extracts are frozen in liquid nitrogen and kept at −70° C. until use.

Example 25

Biotin Pull-Down Assay

To identify whether PPAR-γ or another transcription factor binds to novel promotor motifs, the proteins can be biotin-labeled at the N-terminus (IDT), and used in biotin pull-down assays. The biotin-labeled motifs are incubated with the human adipocyte extracts in gel shift buffer (30 mM Tris-HCl, pH 8.0, 12% glycerol, 70 mM KCl, 1.3 mM dithiothreitol, 0.01% Nonidet P-40, 5.5 mM MgCl$_2$) at 4° C. for 2 hours. Streptavidin beads (Roche Molecular Biochemicals) are then added to the mixture and incubated for 2 hours at 4° C. Beads are washed twice with TNE300_0.1% Nonidet P-40 buffer. The bound proteins are separated on a 4-20% SDS-PAGE and then transferred to a membrane and subjected to Western blotting using an antibody against PPAR-γ or other predicted transcription factors. Alternatively, the bound proteins can be separated on a 4-20% SDS-PAGE followed by silver staining (Silver Stain Plus, Bio-Rad). Negative control can be employed in competition assays in which unlabeled oligonucleotides (40-fold excess of either wild type or mutated oligonucleotide sequences) are added along with biotin probe, for 1 hour before the pull-down assay. The specific bands which only appear in the experimental panel but not in the control panel are concluded to be confirmed transcription factors.

Example 26

Cloning Novel Motifs into Minimum Promoter-Reporter Constructs

Novel motifs and promoters identified as being regulated by PPAR-γ through data integration processes such as ChIP/chip and array methods can be cloned into minimum promoter-reporter constructs using methods standard in the art, to reveal their association in transcriptional regulation during the adipogenesis process.

PCR Amplification, Cloning and Vector Preparation:

Primers can be designed to amplify approximately 200-500 by putative regulatory regions (motifs) in promoters of interest. Two restriction sites can be included at the 5' ends of the forward and reverse primers in order to maintain the motif orientation while cloning into expression reporter vectors. PCR products can be digested with restriction enzymes and then ligated to the pGL-3 basic vector (Promega) and then transformed into human preadipocyte cells.

Example 27

Identification of Function of a Hypothetical Gene

A novel gene FLJ20920, (GenBank NM_025149.1; SEQ ID NO:29) identified during proof of concept studies, appears to block the adipocyte differentiation in human primary adipocytes. A homolog of this gene has been reported to have the same effect in *C. elegans*. Using the data integration strategy, a function can now be attributed to a gene encoding a hypothetical protein, heretofore unassociated with any phenotype or functional attributes. This gene can be further characterized in order to understand its regulation and function in adipocyte differentiation process.

Figure 2:
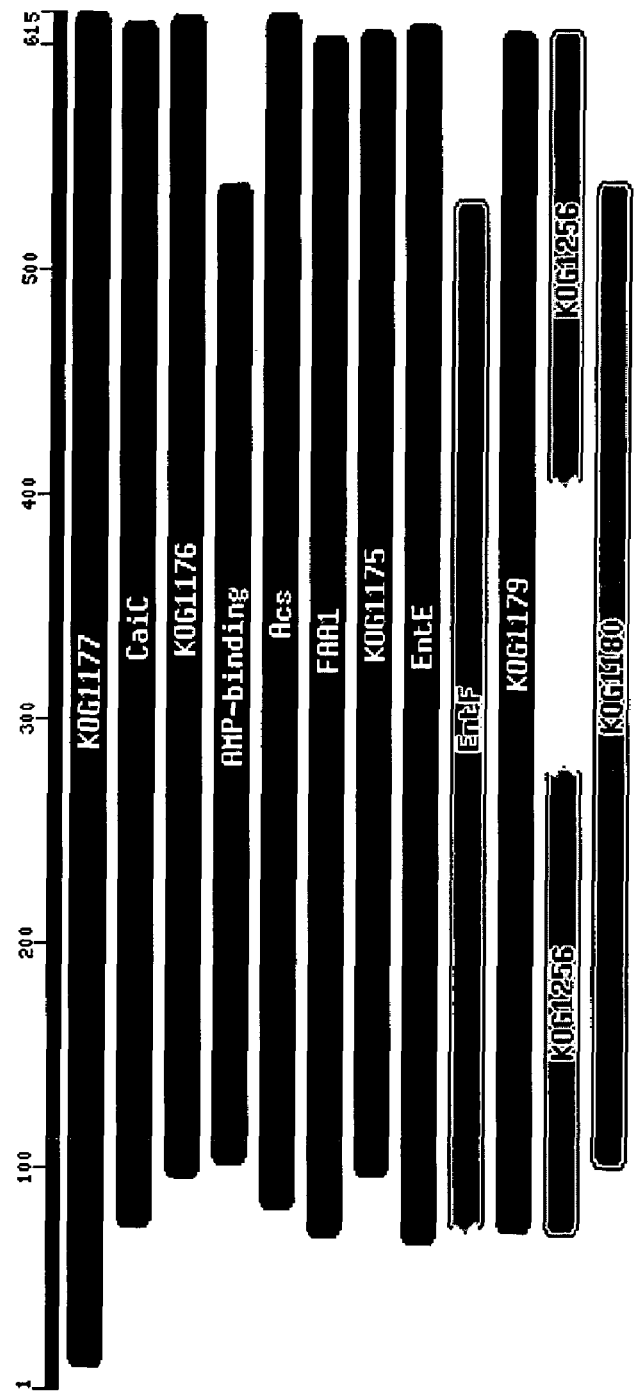
FIG. 2 shows a graphic alignment of the FLJ20920 protein with other proteins displaying high levels of homology. FLJ20920 has high homology to several KOG proteins, as well as Long chain fatty acid acyl-CoA ligase and Acyl-CoA synthetase. (KOG=eukaryotic orthologous groups).

The FLJ20920 hypothetical protein is predicted to be 615 amino acids in length. Using the Conserved Domain Database alignment program (available on the internet at www(dot)ncbi(dot)nlm(dot)nih(dot)gov/entrez/query(dot)fcgi?db=cdd) (Marchler-Bauer et al., Nucleic Acids Res., 2003, 31, 383-387), the FLJ20920 hypothetical protein was found to bear significant homologies to several proteins with sharing the common characteristic of being involved in fatty acid or Acyl CoA synthesis. These include a 596-amino acid residue domain homologous to long chain fatty acid acyl Co-A ligase, and a 534-amino acid residue domain homologous to Acyl-CoA synthetase (AMP-forming) amino acid ligase. These domains in other proteins homologous to the FLJ20920 hypothetical protein are: KOG1177 (Long chain fatty acid acyl-CoA ligase (Lipid transport and metabolism)); CaiC(COG0318, an Acyl-CoA synthetase (AMP-forming)/AMP-acid ligases II (Lipid metabolism/Secondary metabolites biosynthesis, transport, and catabolism)); KOG1176 (an Acyl CoA Synthase); AMP-binding (pfam00501, AMP-binding, AMP-binding enzyme); Acs (Acyl-coenzyme A synthetases/AMP-(fatty) acid ligases (Lipid metabolism)); FAA1 (Long-chain acyl-CoA synthetases (AMP-forming) (Lipid metabolism)); KOG1175 (KOG1175, Acyl-CoA synthetase (Lipid transport and metabolism)); EntE (Peptide arylation enzymes (Secondary metabolites biosynthesis, transport, and catabolism)); EntF(Non-ribosomal peptide synthetase modules and related proteins (Secondary metabolites biosynthesis, transport, and catabolism)); KOG1179 (KOG1179, Very long-chain acyl-CoA synthetase/fatty acid transporter (Lipid transport and metabolism)); KOG1256 (KOG1256, Long-chain acyl-CoA synthetases (AMP-forming) (Lipid transport and metabolism)); and KOG1180 (KOG1180, Acyl-CoA synthetase (Lipid transport and metabolism)). A graphic representation of the domains is shown in FIG. 2.

Example 28

Effects of Oligomeric Compounds on Adipocyte Differentiation Hallmark Genes in Differentiated Adipocytes The effect of the oligomeric compounds and nucleic acid sequences of predicted nuclear receptor/transcription factor-regulated sequences of the present invention on the expression of markers of cellular differentiation can be examined in differentiated adipocytes.

The effects of the oligomeric compounds and nucleic acid sequences of predicted nuclear receptor/transcription factor-regulated sequences of the present invention on the hallmark genes known to be upregulated during adipocyte differentiation can be assayed in undifferentiated, differentiating, or differentiated adipoctyes. As previously described, the HSL, aP2, Glut4, and PPAR-γ genes play important rolls in the uptake of glucose and the metabolism and utilization of fats.

Also as previously described, an increase in triglyceride content is another well-established marker for adipocyte differentiation. Human white preadipocytes (Zen-Bio Inc., Research Triangle Park, N.C.) can be grown in preadipocyte media (ZenBio Inc.). After the cells reach confluence (approximately three days), they are exposed to differentiation media (Zen-Bio, Inc.) containing a PPAR-γ agonist, IBMX, dexamethasone, and insulin for three days. Cells are then fed Adipocyte Medium (Zen-Bio, Inc.), which was replaced at 2 to 3 day intervals. One day before transfection, 96-well plates are seeded with 3000 cells/well. Cells are then transfected on day nine post-differentiation, according to standard published procedures with 250 nM oligonucleotide in LIPO-FECTINT™ (Invitrogen Corporation, Carlsbad, Calif.) (Monia et al., J. Biol. Chem., 1993, 268, 14514-22). Antisense oligonucleotides can be tested in triplicate on each 96-well plate, and the effects of TNF-α, a positive drug control that inhibits adipocyte differentiation, can also be measured in triplicate. Antisense and transfectant-only negative controls may be measured up to six times per plate. On day twelve post-differentiation, cells are washed and lysed at room temperature, and the expression of the four hallmark genes, HSL, aP2, Glut4, and PPAR-γ, as well as triglyceride (TG) accumulation are measured in adipocytes transfected with 2'-MOE uniform or chimeric phosphorothioate (PS) oligomeric compounds. On day twelve post-differentiation, cells are lysed in a guanadinium-containing buffer and total RNA is harvested. The amount of total RNA in each sample is determined using a Ribogreen Assay (Molecular Probes, Eugene, Oreg.). Real-time PCR is performed on the total RNA using primer/probe sets for the adipocyte differentiation hallmark genes Glut4, HSL, aP2, and PPAR-γ. Triglyceride levels as well as mRNA levels for each of the four adipocyte differentiation hallmark genes are expressed as a percentage of control levels (control=treatment with ISIS-29848 (SEQ ID NO:10)). Results are expressed as a percent±standard deviation relative to transfectant-only control.

From these data, it can be observed whether compounds targeting the regulatory regions predicted from these data integrative strategies result in a reduction in the hallmark marker genes before, during or after adipocyte differentiation.

Example 29

Reporter Systems for Assaying Activity of Oligomeric Compounds Targeting or Mimicking microRNAs Reporter systems have been developed to assess the ability of microRNA mimics to provoke a gene silencing response and to assess whether antisense oligomeric compounds targeting microRNAs can inhibit gene silencing activity. In one embodiment, the T-REx™-HeLa cell line (Invitrogen Corp., Carlsbad, Calif.) can be used for transient transfections with plasmids constitutively expressing microRNAs and, in some cases, antisense oligomeric compounds targeting the expressed microRNA are also transfected into the cells. It is understood that other mammalian cells lines can also be used in this reporter system. T-REx™-HeLa Cells are routinely cultured in DMEM, high glucose (Invitrogen Corporation, Carlsbad, Calif.), supplemented with 10% fetal bovine serum (Invitrogen Corporation). Cells are routinely passaged by trypsinization and dilution when they reached 90% confluence. Cells are harvested when they reached 90% confluence, and on the day before transfection with expression or reporter plasmids (described in detail below), the T-REx™-HeLa cells are seeded onto 24-well plates at 50,000 cells/well. The following day, cells are transfected according to standard published procedures with various combinations of plasmids using 2 µg Lipofectamine™ 2000 Reagent (Invitrogen) per µg of plasmid DNA. When transfecting oligomeric compounds, 1-3 µg of Lipofectamine™ 2000 Reagent is used per 100 nM oligonucleotide.

Examples of plasmids that can be used are as follows: The pcDNA3.1©/NT-GFP (Invitrogen) plasmid, containing a CMV promoter controlling expression of a GFP reporter sequence at the N-terminus of the transcription start site was used as a control plasmid. The pcDNA3.1©/NT-promoter sensor plasmid can contain (in addition to the elements above) predicted gene regulatory nucleotide sites, downstream of the GFP coding sequence and upstream of the polyadenylation signal. Additionally, in order to test the effect of an antisense oligomeric compound targeting a microRNA, the T-REx™-HeLa cells can also be transfected with ISIS Number 155990 (SEQ ID NO:11, targeted to PPAR-γ as previously described.

Twenty-four hours post-transfection, cells are trypsinized and GFP fluorescence can be analyzed by flow cytometry. It can thus be determined whether the predicted transcription factor promoter element acts as a true binding site for PPAR-γ.

In one embodiment, an expression system based on the pGL3-Control (Promega Corp., Madison Wis.) vector containing a CMV promoter controlling expression of a luciferase reporter sequence may be used in transient transfections of HeLa cells with plasmids expressing predicted regulatory sites. The unmodified pGL3-Control luciferase reporter vector can be used as a control. To control for transfection efficiency, 100 ng each of an experimental luciferase plasmid with 8 ng of the *Renilla*-containing pRL-TK control plasmid (Promega) can be cotransfect into preadipocyte cells, using the FuGene6 Lipofectamine Reagent (Roche). After 24 hrs, lysates are prepared from each transfection, and luciferase activity assayed in a luminometer. Preadipocytes can also be allowed to differentiate into adipocytes and lysates prepared after 3, 5 and 7 days to assay the luciferase and renilla activity.

HeLa Cells are routinely cultured and passaged as described, supra, and on the day before transfection with expression or reporter plasmids, the HeLa cells are seeded onto 24-well plates 50,000 cells/well. Cells are transfected according to standard published procedures with various combinations of plasmids using 2 µg Lipofectamine™ 2000 Reagent (Invitrogen) per µg of plasmid DNA, or, when transfecting oligomeric compounds, 1.25 µg of Lipofectamine™ 2000 Reagent per 100 nM oligonucleotide or double-stranded RNA. The luciferase signal in each well can be normalized to the *Renilla* luciferase (RL) activity produced from a co-transfected plasmid, pRL-CMV, which is transfected at 0.5 µg per well. Cells are treated at various dosages (4 nM, 20 nM, and 100 nM). A luciferase assay is performed 48-hours after transfection. Briefly, cells are lysed in passive lysis buffer (PLB; Promega), and 20 ul of the lysate is then assayed for RL activity using a Dual Luciferase Assay kit (Promega) according to the manufacturer's protocol.

Thus, predicted nuclear receptor/transcription factor regulatory elements can be tested for their ability to be bound and regulated by transcription factors.

Example 30

Antisense Inhibition of Human FLJ20920 Expression by Chimeric Phosphorothioate Oligonucleotides Having 2'-MOE Wings and a Deoxy Gap In accordance with the present invention, a series of antisense compounds was designed to target different regions of the human FLJ20920 RNA, using published sequences (GenBank accession number NM_025149.1; SEQ ID NO:29).

The compounds are shown in Table 3. "Target site" indicates the first (5'-most) nucleotide number on the particular target sequence to which the compound binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human FLJ20920 mRNA levels by quantitative real-time PCR as described in other examples herein. Data are averages from three experiments in which A549 cells were treated with the antisense oligonucleotides of the present invention. The positive control for each datapoint is identified in the table by sequence ID number. If present, "N.D." indicates "no data."

TABLE 3

Inhibition of human FLJ20920 mRNA levels by chimeric phosphorothioate oligonucleotides having 2'-MOE wings and a deoxy gap

| Isis Number | Sequence | Target Site | Percent Control | SEQ ID NO |
|---|---|---|---|---|
| 331519 | TAGACAGCCATGGCTCGCTT | 3 | N.D. | 30 |
| 331520 | GGAACTGAGGAAGCGGACAC | 124 | 24 | 31 |
| 331521 | AGCTGAGGCCTCCGATGGGC | 170 | N.D. | 32 |
| 331522 | ACAGTCTTGCTGTTAAGATG | 213 | 20 | 33 |
| 331523 | TCTGGGACCCTCTGTGCTGT | 252 | 11 | 34 |
| 331524 | TTGTCCACCTCCTCCTTGAG | 324 | N.D. | 35 |
| 331525 | GCAGCTTTGTCCACCTCCTC | 330 | N.D. | 36 |
| 331526 | CAGAAGCAGCTTTGTCCACC | 335 | N.D. | 37 |
| 331527 | AGAGGCCAATGCTCAGGAGG | 356 | 9 | 38 |
| 331528 | CATGCCCAGCCGGTCACCTT | 379 | 21 | 39 |
| 331529 | ATGCATAGGAGTTAGGTCCC | 401 | 13 | 40 |
| 331530 | CAGAATGATGCCCGCCTGGG | 445 | 22 | 41 |
| 331531 | GCTGGGTTCACAGACACCAG | 462 | 24 | 42 |
| 331532 | GGTAGGCTGGGTTCACAGAC | 467 | 5 | 43 |
| 331533 | TCTTGAGGACATACTCCAGT | 497 | 24 | 44 |
| 331534 | TGGACAGATCTGCTTCAGGA | 577 | 5 | 45 |
| 331535 | CCACTTCTGGACAGATCTGC | 584 | 27 | 46 |
| 331536 | TGGCTGGGCATTCTCCACTT | 598 | 15 | 47 |
| 331537 | GGCCCCTGGCTGGGCATTCT | 604 | 29 | 48 |
| 331538 | CTCTTCAAGGCCCCTGGCTG | 612 | N.D. | 49 |
| 331539 | TGTGGTCAGATCTGGGAGCC | 637 | 11 | 50 |
| 331540 | CAGGAGCAGGGTCCCCGGCA | 679 | N.D. | 51 |
| 331541 | TCATCCAGGAGCAGGGTCCC | 684 | N.D. | 52 |
| 331542 | TCCAGATGCTGCCGTGTGCT | 720 | 4 | 53 |
| 331543 | GGCAGGACAGGAACTGCTGG | 755 | 6 | 54 |
| 331544 | GTGAACTGGATGTTGATGGG | 780 | N.D. | 55 |
| 331545 | CCGAGGTGAACTGGATGTTG | 785 | N.D. | 56 |
| 331546 | TGTCCCCGAGGTGAACTGGA | 790 | N.D. | 57 |
| 331547 | GCCTGTTGTCCCCGAGGTGA | 796 | 20 | 58 |
| 331548 | GTTGACAATGTTGTAGTGGG | 838 | 40 | 59 |
| 331549 | TCCTAAAATGTTGGAGTTGT | 856 | 25 | 60 |
| 331550 | GCTCTGGTGTCTTCTCATGC | 890 | 21 | 61 |
| 331551 | AGGATCATCCGCAACTGCTC | 906 | 8 | 62 |
| 331552 | TGCCTGCCACGGAACCCAGG | 947 | 11 | 63 |
| 331553 | GTACATCAGACACATCATTG | 967 | 16 | 64 |
| 331554 | AAGATGGGAGAGGCCAGGAT | 999 | 30 | 65 |
| 331555 | GAAGGTGCCTCTCTCTCTGC | 1048 | 19 | 66 |
| 331556 | GGGTACCATACAGGAAGGTG | 1061 | 23 | 67 |
| 331557 | TAACTGGAGAAGTCTGGCTG | 1107 | N.D. | 68 |
| 331558 | CGGATCAACTCTGGAGGTGC | 1170 | 23 | 69 |
| 331559 | ATCTTGTTGATGATGGCTCG | 1188 | N.D. | 70 |
| 331560 | TTCATGATCCGGGCCTCCGT | 1329 | 33 | 71 |
| 331561 | GTGTTCAGCTTTGCCAGCGT | 1362 | 12 | 72 |
| 331562 | TACCCTCGGATGCACAGCTC | 1389 | 29 | 73 |
| 331563 | ATGACGCAGTACCCTCGGAT | 1398 | N.D. | 74 |
| 331564 | CTTCTGAGGCTCACCCCAGT | 1426 | 28 | 75 |
| 331565 | GTCCTGATCCACTGCTTCCT | 1450 | 33 | 76 |
| 331566 | ACGATCTTGCAGAAGCCCTG | 1509 | N.D. | 77 |
| 331567 | GGTGTGTGTGAAAGAAGTCC | 1589 | 38 | 78 |
| 331568 | ACCTTCGGGTGTGTGTGAAA | 1596 | 44 | 79 |
| 331569 | AAATCTCTTCCCCCATCCGA | 1649 | 81 | 80 |
| 331570 | TCCCCGTCCTTCAGCCGAAT | 1677 | 42 | 81 |
| 331571 | TTCCCTTTGCAGAAAGCTTT | 1719 | N.D. | 82 |
| 331572 | TTTGTGACAAACACGATGTA | 1764 | 32 | 83 |
| 331573 | AATTTCTGGATCTTTTCCTGA | 1800 | N.D. | 84 |
| 331574 | ACAGAAAGCTCTTTATGCCA | 2116 | 34 | 85 |

These sequences are shown to contain thymine (T) but one of skill in the art will appreciate that thymine (T) is generally replaced by uracil (U) in RNA sequences.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers and sequences, and the like) cited in the present application is incorporated herein by reference in its entirety. In addition, the term "(dot)" refers to a "." within a web site link.

What is claimed is:

1. A method of decreasing triglyceride accumulation in a preadipocyte or adipocyte cell comprising contacting a preadipocyte or adipocyte cell with an effective amount of a compound comprising an oligonucleotide consisting of 12 to 50 linked nucleosides, wherein said oligonucleotide has a nucleobase sequence that is at least 90% complementary to SEQ ID NO:29 as measured over the entirety of said oligonucleotide, wherein the oligonucleotide comprises at least one modified nucleobase, modified sugar, or modified internucleoside linkage, wherein said triglyceride accumulation is decreased, and wherein the compounds is single-stranded.

2. The method of claim 1 wherein the modified sugar is a 2'-O-methoxyethyl sugar moiety, wherein the modified oligonucleoside linkage is a phosphorothioate internucleoside linkage, and wherein the modified nucleobase is a 5-methylcytosine.

3. The method of claim 1 wherein the preadipocyte or adipocyte cell is in an animal that has a metabolic disease.

4. The method of claim 3 wherein the metabolic disease is obesity or diabetes.

5. The method of claim 1, wherein each internucleoside linkage of said oligonucleotide is a phosphorothioate internucleoside linkage.

6. The method of claim 1 wherein the modified sugar is a bicyclic sugar.

7. The method of claim 1 wherein the modified sugar is a 2'-O-methoxyethyl sugar or a 4'-$(CH_2)_n$-O-2' bridge, wherein n is 1 or 2.

8. The method of claim 1, wherein the modified nucleobase is a 5-methylcytosine.

9. The method of claim 1, wherein the oligonucleotide comprises:
   a gap segment consisting of linked 2'-deoxynucleosides;
   a 5' wing segment consisting of linked nucleosides;
   a 3' wing segment consisting of linked nucleosides;
   wherein the gap segment is positioned between the 5' wing segment and the 3' wing segment, each nucleoside of each wing segment comprises a modified sugar, and each internucleoside linkage is a phosphorothioate internucleoside linkage.

10. The method of claim 1, wherein the oligonucleotide comprises:
    a gap segment consisting of ten linked 2'-deoxynucleosides;
    a 5' wing segment consisting of five linked nucleosides;
    a 3' wing segment consisting of five linked nucleosides;
    wherein the gap segment is positioned between the 5' wing segment and the 3' wing segment, wherein each nucleoside of each wing segment comprises a 2'-O-methoxyethyl sugar; and wherein each internucleoside linkage of said oligonucleotide is a phosphorothioate linkage.

11. The method of claim 10, wherein the oligonucleotide comprises at least one modified cytosine, wherein the modified cytosine is a 5-methylcytosine.

12. The method of claim 11, wherein each cytosine is a 5-methylcytosine.

13. The method of claim 12, wherein the oligonucleotide has a nucleobase sequence comprising at least 15 contiguous nucleobases of a nucleobase sequence selected from among the nucleobase sequences recited in SEQ ID NOs 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, and 85.

14. The method of claim 13, wherein the oligonucleotide has a nucleobase sequence that is 100% complementary to SEQ ID NO: 29.

15. The method of claim 12, wherein the oligonucleotide has a nucleobase sequence consisting of a nucleobase sequence selected from among the nucleobase sequences recited in SEQ ID NOs 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, and 85.

16. The method of claim 1, wherein the oligonucleotide has a nucleobase sequence that is 100% complementary to SEQ ID NO: 29.

17. The method of claim 1, wherein the oligonucleotide consists of 20 linked nucleosides.

18. The method of claim 1, wherein the oligonucleotide has a nucleobase sequence comprising at least 15 contiguous nucleobases of a nucleobase sequence selected from among the nucleobase sequences recited in SEQ ID NOs 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, and 85.

19. The method of claim 1, wherein the oligonucleotide has a nucleobase sequence consisting of a nucleobase sequence selected from among the nucleobase sequences recited in SEQ ID NOs 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, and 85.

20. The method of claim 1 further comprising inhibiting adipocyte differentiation in said preadipocyte cell.

21. The method of claim 1, wherein said oligonucleotide consists of 15 to 30 linked nucleosides.

22. The method of claim 1, wherein said nucleobase sequence is at least 95% complementary to SEQ ID NO: 29 as measured over the entirety of said oligonucleotide.

23. The method of claim 10, wherein said oligonucleotide consists of 20 linked nucleosides.

\* \* \* \* \*

SEQUENCE LISTING

<160> NUMBER OF SEQ ID NOS: 85

<210> SEQ ID NO 1
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 1
tccgtcatcg ctcctcaggg                                                    20

<210> SEQ ID NO 2
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 2
gtgcgcgcga gcccgaaatc                                                    20

<210> SEQ ID NO 3
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 3
atgcattctg cccccaagga                                                    20

<210> SEQ ID NO 4
<211> LENGTH: 1100
<212> TYPE: DNA
<213> ORGANISM: H. sapiens

<400> SEQUENCE: 4
catagagaac tccattgttt cgtgatgact acacttatcg tttaaacatc aattgatgtt         60
caaacatcag ctggtgtaac attgctgcag ttgctattga tggataagct gaagttttta        120
agaaagcaaa cccgatgtat aaaattgaaa ccatatcaaa cccttcttca ttctctcagc        180
tatttaattt tacagaattt agatagcagt cagtatcatt ttgggcttca caaatcagta        240
gagtaagtac cttaggaata taacatttca gtagcatgct gataccaacg tttaaactat        300
ggatacatat ttgaattcca aattttcctt caaataatgt gattagagat tcaaccagga        360
atagacaccg aaagaaaact tgcccaaat aagctttctg gtatttcata agcaagagat        420
ttaagttttc catttaagaa gcaattgtga attttacaac aataaaaaat gcaagtggat        480
attgaacagt ctctgctctg ataattctaa atacagtaca gttcacgccc ctcacaagac        540
actgaacatg tgggtcaccg gcgagacagt gtggcaatat tttccctgta atgtaccaag        600
tcttgccaaa gcagtgaaca ttatgacaca acttttgtc acagctggct cctaatagga        660
cagtgccagc caattcaagc ccagtccttt ctgtgtttat tcccatctct cccaaatatt        720
tggaaactga tgtcttgact catgggtgta ttcacaaatt ctgttacttc aagtcttttt        780
cttttaacgg attgatcttt tgctagatag agacaaaata tcagtgtgaa ttacagcaaa        840
cccctattcc atgctgttat gggtgaaact ctggagatt ctcctattga cccagaaagc        900
gattccttca ctgatacact gtctgcaaac atatcacaag gtaaagttcc ttccagatac        960
ggctattggg gacgtggggg catttatgta agggtaaaat tgctcttgta gtttgtcttc       1020
caggttgtgt ttgttttaat actatcatgt gtacactcca gtattttaat gcttagctcg       1080
ttgctatcgc gttcattaac                                                   1100

<210> SEQ ID NO 5
<211> LENGTH: 13
<212> TYPE: DNA
<213> ORGANISM: Artificial Sequence

```
<220> FEATURE:
<221> NAME/KEY: misc_feature
<222> LOCATION: (1)...(13)
<223> OTHER INFORMATION: DNA regulatory element
<220> FEATURE:
<221> NAME/KEY: misc_feature
<222> LOCATION: 7
<223> OTHER INFORMATION: n = A,T,C or G

<400> SEQUENCE: 5
tgacctntga cct                                                          13

<210> SEQ ID NO 6
<211> LENGTH: 19
<212> TYPE: RNA
<213> ORGANISM: Artificial Sequence
<220> FEATURE:
<223> OTHER INFORMATION: Artificially synthesized oligonucleotide

<400> SEQUENCE: 6
cgagaggcgg acgggaccg                                                    19

<210> SEQ ID NO 7
<211> LENGTH: 21
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (1)...(19)
<223> OTHER INFORMATION: bases at these positions are RNA

<400> SEQUENCE: 7
cgagaggcgg acgggaccgt t                                                 21

<210> SEQ ID NO 8
<211> LENGTH: 21
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (3)...(21)
<223> OTHER INFORMATION: bases at these positions are RNA

<400> SEQUENCE: 8
ttgcucuccg ccugcccugg c                                                 21

<210> SEQ ID NO 9
<211> LENGTH: 19
<212> TYPE: RNA
<213> ORGANISM: Artificial Sequence
<220> FEATURE:
<223> OTHER INFORMATION: Artificially synthesized oligonucleotide

<400> SEQUENCE: 9
gcucuccgcc ugcccuggc                                                    19

<210> SEQ ID NO 10
<211> LENGTH: 20
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (1)...(20)
```

<223> OTHER INFORMATION: n = A,T,C or G

<400> SEQUENCE: 10
nnnnnnnnnn nnnnnnnnnn                                              20

<210> SEQ ID NO 11
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 11
agcaaaagat caatccgtta                                              20

<210> SEQ ID NO 12
<211> LENGTH: 115
<212> TYPE: DNA
<213> ORGANISM: H. sapiens

<400> SEQUENCE: 12
aaagtttcag agcaggaatg aaagtaaagt acatttagaa gatgaccaag caggctactt   60
gagagattca aaaagtgcat ggtttgacct ttgacctggg cttttatatg ttggc       115

<210> SEQ ID NO 13
<211> LENGTH: 12
<212> TYPE: DNA
<213> ORGANISM: Artificial Sequence
<220> FEATURE:
<221> NAME/KEY: misc_feature
<222> LOCATION: (1)...(12)
<223> OTHER INFORMATION: DNA regulatory element

<400> SEQUENCE: 13
tgaccttgtc ct                                                      12

<210> SEQ ID NO 14
<211> LENGTH: 120
<212> TYPE: DNA
<213> ORGANISM: H. sapiens

<400> SEQUENCE: 14
ttggtttcct cttggaagac tgaccagaaa gcatgacact agtctcaatt ttctgccaat   60
atctgtccct ccacagatac taccccacta atgaccttgt cctttggccc acttacagca  120

<210> SEQ ID NO 15
<211> LENGTH: 12
<212> TYPE: DNA
<213> ORGANISM: Artificial Sequence
<220> FEATURE:
<221> NAME/KEY: misc_feature
<222> LOCATION: (1)...(12)
<223> OTHER INFORMATION: DNA regulatory element

<400> SEQUENCE: 15
tgaccttggc ct                                                      12

<210> SEQ ID NO 16
<211> LENGTH: 115
<212> TYPE: DNA
<213> ORGANISM: H. sapiens

<400> SEQUENCE: 16
tttcttcttt ctttggaggc agaaattggg cataagacaa tatgaggggt ggtctcctcc   60

```
cttatcgcca tgttgaccaa gctggtctca aactcctgac cttggcctcc caaat       115
```

<210> SEQ ID NO 17
<211> LENGTH: 12
<212> TYPE: DNA
<213> ORGANISM: Artificial Sequence
<220> FEATURE:
<221> NAME/KEY: misc_feature
<222> LOCATION: (1)...(12)
<223> OTHER INFORMATION: DNA regulatory element

<400> SEQUENCE: 17

```
tgaccttgtc ct                                                       12
```

<210> SEQ ID NO 18
<211> LENGTH: 114
<212> TYPE: DNA
<213> ORGANISM: H. sapiens

<400> SEQUENCE: 18

```
gctgtttctt gtagggtatt ctaaatcaga aacctacact tagtctgcaa atagaagcct   60
gtgtgacctt gtccttcctc cacactgggt tgatgggtgc tatcctggtc agga         114
```

<210> SEQ ID NO 19
<211> LENGTH: 23
<212> TYPE: DNA
<213> ORGANISM: Artificial Sequence
<220> FEATURE:
<223> OTHER INFORMATION: PCR primer

<400> SEQUENCE: 19

```
ctcagcaaat ttagctcttc atc                                           23
```

<210> SEQ ID NO 20
<211> LENGTH: 23
<212> TYPE: DNA
<213> ORGANISM: Artificial Sequence
<220> FEATURE:
<223> OTHER INFORMATION: PCR primer

<400> SEQUENCE: 20

```
ccttcaacag cagagaggt gtc                                            23
```

<210> SEQ ID NO 21
<211> LENGTH: 24
<212> TYPE: DNA
<213> ORGANISM: Artificial Sequence
<220> FEATURE:
<223> OTHER INFORMATION: PCR primer

<400> SEQUENCE: 21

```
gctactacaa tttctgagtg ttgg                                          24
```

<210> SEQ ID NO 22
<211> LENGTH: 26
<212> TYPE: DNA
<213> ORGANISM: Artificial Sequence
<220> FEATURE:
<223> OTHER INFORMATION: PCR primer

<400> SEQUENCE: 22

```
ggccttgaaa atgacatcga tggcag                                        26
```

<210> SEQ ID NO 23

```
<211> LENGTH: 21
<212> TYPE: DNA
<213> ORGANISM: Artificial Sequence
<220> FEATURE:
<223> OTHER INFORMATION: PCR primer

<400> SEQUENCE: 23
cagatatcag taactacgct g                                             21

<210> SEQ ID NO 24
<211> LENGTH: 23
<212> TYPE: DNA
<213> ORGANISM: Artificial Sequence
<220> FEATURE:
<223> OTHER INFORMATION: PCR primer

<400> SEQUENCE: 24
gaatgaaatg taacatcaag acc                                           23

<210> SEQ ID NO 25
<211> LENGTH: 24
<212> TYPE: DNA
<213> ORGANISM: Artificial Sequence
<220> FEATURE:
<223> OTHER INFORMATION: PCR primer

<400> SEQUENCE: 25
ggaggcagaa attgggcata agac                                          24

<210> SEQ ID NO 26
<211> LENGTH: 22
<212> TYPE: DNA
<213> ORGANISM: Artificial Sequence
<220> FEATURE:
<223> OTHER INFORMATION: PCR primer

<400> SEQUENCE: 26
gtcttacagt tctggaggcc ag                                            22

<210> SEQ ID NO 27
<211> LENGTH: 23
<212> TYPE: DNA
<213> ORGANISM: Artificial Sequence
<220> FEATURE:
<223> OTHER INFORMATION: PCR primer

<400> SEQUENCE: 27
caggactaga tgcaaacctc cag                                           23

<210> SEQ ID NO 28
<211> LENGTH: 22
<212> TYPE: DNA
<213> ORGANISM: Artificial Sequence
<220> FEATURE:
<223> OTHER INFORMATION: PCR primer

<400> SEQUENCE: 28
cattgagtaa ctacttgctg ac                                            22

<210> SEQ ID NO 29
<211> LENGTH: 2161
<212> TYPE: DNA
<213> ORGANISM: H. sapiens

<400> SEQUENCE: 29
aaaagcgagc catggctgtc tacgtcggga tgctgcgcct ggggaggctg tgcgccggga   60
```

```
gctcgggggt gctgggggcc cgggccgccc tctctcggag ttggcaggaa gccaggttgc      120
agggtgtccg cttcctcagt tccagagagg tggatcgcat ggtctccacg cccatcggag      180
gcctcagcta cgttcagggg tgcaccaaaa agcatcttaa cagcaagact gtgggccagt      240
gcctggagac cacagcacag agggtcccag aacgagaggc cttggtcgtc ctccatgaag      300
acgtcaggtt gaccttttgcc caactcaagg aggaggtgga caaagctgct tctggcctcc      360
tgagcattgg cctctgcaaa ggtgaccggc tgggcatgtg gggacctaac tcctatgcat      420
gggtgctcat gcagttggcc accgccccag cgggcatcat tctggtgtct gtgaacccag      480
cctaccaggc tatggaactg gagtatgtcc tcaagaaggt gggctgcaag gcccttgtgt      540
tccccaagca attcaagacc cagcaatact acaacgtcct gaagcagatc tgtccagaag      600
tggagaatgc ccagccaggg gccttgaaga gtcagaggct cccagatctg accacagtca      660
tctcggtgga tgcccctttg ccggggaccc tgctcctgga tgaagtggtg gcggctggca      720
gcacacggca gcatctggac cagctccaat acaaccagca gttcctgtcc tgccatgacc      780
ccatcaacat ccagttcacc tcggggacaa caggcagccc caaggggggcc accctctccc      840
actacaacat tgtcaacaac tccaacattt taggagagcg cctgaaactg catgagaaga      900
caccagagca gttgcggatg atcctgccca ccccctgta ccattgcctg ggttccgtgg      960
caggcacaat gatgtgtctg atgtacggtg ccaccctcat cctggcctct cccatcttca     1020
atggcaagaa ggcactggag gccatcagca gagagagagg caccttcctg tatggtaccc     1080
ccacgatgtt cgtggacatt ctgaaccagc cagacttctc cagttatgac atctcgacca     1140
tgtgtggagg tgtcattgct gggtcccctg cacctccaga gttgatccga gccatcatca     1200
acaagataaa tatgaaggac ctggtggttg cttatgaaac cacagagaac agtcccgtga     1260
cattcgcgca cttccctgag gacactgtgg agcagaaggc agaaagcgtg gcagaattat     1320
gcctcacac ggaggcccgg atcatgaaca tggaggcagg gacgctggca aagctgaaca     1380
cgcccgggga gctgtgcatc cgagggtact gcgtcatgct gggctactgg ggtgagcctc     1440
agaagacaga ggaagcagtg gatcaggaca agtggtattg acaggagat gtcgccacaa     1500
tgaatgagca gggcttctgc aagatcgtgg gccgctctaa ggatatgatc atccggggtg     1560
gtgagaacat ctaccccgca gagctcgagg acttctttca cacacacccg aaggtgcagg     1620
aagtgcaggt ggtgggagtg aaggacgatc ggatggggga agagatttgt gcctgcattc     1680
ggctgaagga cggggaggag accacggtgg aggagataaa agctttctgc aaagggaaga     1740
tctctcactt caagattccg aagtacatcg tgtttgtcac aaactacccc ctcaccattt     1800
caggaaagat ccagaaattc aaacttcgag agcagatgga acgacatcta aatctgtgaa     1860
taaagcagca ggcctgtcct ggccggttgg cttgactctc tcctgtcaga atgcaacctg     1920
gctttatgca cctagatgtc cccagcaccc agttctgagc caggcacatc aaatgtcaag     1980
gaattgactg aacgaactaa gagctcctgg atgggtccgg aactcgcct gggcacaagg     2040
tgccaaaagg caggcagcct gcccaggccc tccctcctgt ccatccccca cattcccctg     2100
tctgtccttg tgatttggca taaagagctt tctgttttcg aaaaaaaaaa aaaaaaaaa     2160
a                                                                     2161
```

<210> SEQ ID NO 30
<211> LENGTH: 20
<212> TYPE: DNA
<213> ORGANISM: Artificial Sequence
<220> FEATURE:

<223> OTHER INFORMATION: Artificially synthesized oligonucleotide

<400> SEQUENCE: 30
tagacagcca tggctcgctt                                               20

<210> SEQ ID NO 31
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 31
ggaactgagg aagcggacac                                               20

<210> SEQ ID NO 32
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 32
agctgaggcc tccgatgggc                                               20

<210> SEQ ID NO 33
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 33
acagtcttgc tgttaagatg                                               20

<210> SEQ ID NO 34
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 34
tctgggaccc tctgtgctgt                                               20

<210> SEQ ID NO 35
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 35
ttgtccacct cctccttgag                                               20

<210> SEQ ID NO 36
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 36
gcagctttgt ccacctcctc                                               20

<210> SEQ ID NO 37
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 37
cagaagcagc tttgtccacc                          20

<210> SEQ ID NO 38
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 38
agaggccaat gctcaggagg                          20

<210> SEQ ID NO 39
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 39
catgcccagc cggtcacctt                          20

<210> SEQ ID NO 40
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 40
atgcatagga gttaggtccc                          20

<210> SEQ ID NO 41
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 41
cagaatgatg cccgcctggg                          20

<210> SEQ ID NO 42
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 42
gctgggttca cagacaccag                          20

<210> SEQ ID NO 43
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 43
ggtaggctgg gttcacagac                                          20

<210> SEQ ID NO 44
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 44
tcttgaggac atactccagt                                          20

<210> SEQ ID NO 45
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 45
tggacagatc tgcttcagga                                          20

<210> SEQ ID NO 46
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 46
ccacttctgg acagatctgc                                          20

<210> SEQ ID NO 47
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 47
tggctgggca ttctccactt                                          20

<210> SEQ ID NO 48
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 48
ggcccctggc tgggcattct                                          20

<210> SEQ ID NO 49
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 49
ctcttcaagg cccctggctg                                          20

<210> SEQ ID NO 50
<211> LENGTH: 20

-continued

```
<212> TYPE: DNA
<213> ORGANISM: Artificial Sequence
<220> FEATURE:
<223> OTHER INFORMATION: Artificially synthesized oligonucleotide

<400> SEQUENCE: 50
tgtggtcaga tctgggagcc                                            20

<210> SEQ ID NO 51
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 51
caggagcagg gtccccggca                                            20

<210> SEQ ID NO 52
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 52
tcatccagga gcagggtccc                                            20

<210> SEQ ID NO 53
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 53
tccagatgct gccgtgtgct                                            20

<210> SEQ ID NO 54
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 54
ggcaggacag gaactgctgg                                            20

<210> SEQ ID NO 55
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 55
gtgaactgga tgttgatggg                                            20

<210> SEQ ID NO 56
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 56
```
ccgaggtgaa ctggatgttg 20

<210> SEQ ID NO 57
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 57
tgtccccgag gtgaactgga 20

<210> SEQ ID NO 58
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 58
gcctgttgtc cccgaggtga 20

<210> SEQ ID NO 59
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 59
gttgacaatg ttgtagtggg 20

<210> SEQ ID NO 60
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 60
tcctaaaatg ttggagttgt 20

<210> SEQ ID NO 61
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 61
gctctggtgt cttctcatgc 20

<210> SEQ ID NO 62
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 62
aggatcatcc gcaactgctc 20

<210> SEQ ID NO 63
<211> LENGTH: 20
<212> TYPE: DNA
<213> ORGANISM: Artificial Sequence

```
<220> FEATURE:
<223> OTHER INFORMATION: Artificially synthesized oligonucleotide

<400> SEQUENCE: 63
tgcctgccac ggaacccagg                                                 20

<210> SEQ ID NO 64
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 64
gtacatcaga cacatcattg                                                 20

<210> SEQ ID NO 65
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 65
aagatgggag aggccaggat                                                 20

<210> SEQ ID NO 66
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 66
gaaggtgcct ctctctctgc                                                 20

<210> SEQ ID NO 67
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 67
gggtaccata caggaaggtg                                                 20

<210> SEQ ID NO 68
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 68
taactggaga agtctggctg                                                 20

<210> SEQ ID NO 69
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 69
cggatcaact ctggaggtgc                                                 20
```

```
<210> SEQ ID NO 70
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 70
atcttgttga tgatggctcg                                              20

<210> SEQ ID NO 71
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 71
ttcatgatcc gggcctccgt                                              20

<210> SEQ ID NO 72
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 72
gtgttcagct ttgccagcgt                                              20

<210> SEQ ID NO 73
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 73
taccctcgga tgcacagctc                                              20

<210> SEQ ID NO 74
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 74
atgacgcagt accctcggat                                              20

<210> SEQ ID NO 75
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 75
cttctgaggc tcaccccagt                                              20

<210> SEQ ID NO 76
<211> LENGTH: 20
<212> TYPE: DNA
<213> ORGANISM: Artificial Sequence
<220> FEATURE:
<223> OTHER INFORMATION: Artificially synthesized oligonucleotide
```

```
<400> SEQUENCE: 76
gtcctgatcc actgcttcct                                                    20

<210> SEQ ID NO 77
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 77
acgatcttgc agaagccctg                                                    20

<210> SEQ ID NO 78
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 78
ggtgtgtgtg aaagaagtcc                                                    20

<210> SEQ ID NO 79
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 79
accttcgggt gtgtgtgaaa                                                    20

<210> SEQ ID NO 80
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 80
aaatctcttc ccccatccga                                                    20

<210> SEQ ID NO 81
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 81
tccccgtcct tcagccgaat                                                    20

<210> SEQ ID NO 82
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 82
ttccctttgc agaaagcttt                                                    20

<210> SEQ ID NO 83
```

```
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 83
tttgtgacaa acacgatgta                                               20

<210> SEQ ID NO 84
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 84
aatttctgga tctttcctga                                               20

<210> SEQ ID NO 85
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 85
acagaaagct ctttatgcca                                               20
```